United States Patent [19]

Springer et al.

[11] Patent Number: 5,284,931
[45] Date of Patent: Feb. 8, 1994

[54] INTERCELLULAR ADHESION MOLECULES, AND THEIR BINDING LIGANDS

[75] Inventors: Timothy A. Springer, Newton, Mass.; Robert Rothlein; Steven D. Marlin, both of Danbury, Conn.; Michael L. Dustin, University City, Mo.

[73] Assignee: Dana Farber Cancer Institute, Boston, Mass.

[21] Appl. No.: 515,478

[22] Filed: Apr. 27, 1990

Related U.S. Application Data

[63] Continuation-in-part of Ser. No. 456,647, Dec. 22, 1989, which is a continuation-in-part of Ser. No. 45,963, May 4, 1987, which is a continuation-in-part of Ser. No. 115,798, Nov. 2, 1987, which is a continuation-in-part of Ser. No. 155,943, Feb. 16, 1988, which is a continuation-in-part of Ser. No. 189,815, May 3, 1988, which is a continuation-in-part of Ser. No. 250,446, Sep. 28, 1988, which is a continuation-in-part of Ser. No. 324,481, Mar. 16, 1989, which is a continuation-in-part of Ser. No. 373,882, Jun. 30, 1989, which is a continuation-in-part of Ser. No. 456,647, Dec. 22, 1989.

[51] Int. Cl.$^5$ ............................................. A61K 39/395
[52] U.S. Cl. ............................. 424/85.8; 530/388.22; 530/395; 530/808; 530/868; 514/8
[58] Field of Search ................. 424/85.8, 85.91; 530/387, 389, 808, 388.22

[56] References Cited

PUBLICATIONS

Cunningham C; et al., TIBTECH 10, Apr., 1992. "Antibody engineering—how to be human."
Dantel, J., et al., Curr. Opin. Immunol. 3:740–747 (1991), "Use of Monoclonal antibodies in human transplantation,"
Flavin, T., et al., Transpl. Proc. 23(1):533–534 (Feb. 1991) "Monoclonal antibodies against intercellular adhesion molecule 1 prglong caroige allograft survival in CY momolgus monkeys."
Gibbs, W. W., Scientific American (Jul. 1993), "Try, try again," pp. 101–103.
Hams, W. J., et al. Tibtech 11 (Feb. 1993), pp. 42–44. "Therapeutic antibodies—the comming of age."
Haug, C. E., et al., Transplantation 55:766–773, (Apr. 1993), "A Phase I trial of immunosuppression with anti-, cam-12 (CD54) m Ab in renal allograft recipients."
Ortho Multicenter Transplant Study Group, New Engl. J. Med. 313:337–341 (Aug. 8, 1985).
Physician's Desk Reference (1993), pp. 1702–1703. "Ortheclone OKT3".
Marlin, S. D. et al. 1987. Cell 51: 813–819. "Purified Intercellular Adhesion Molecule—1 ... "
Rothlein, R. et al. 1986. J. Immunol. 137:1270–1274. "A Human Intercullar Adhesion Molecule (1CAM-1) ... "
Dustin, M. L. et al. 1986. J. Immunol. 137(1):245 "Induction by 1L1 and Interferan—8: ... "
Cosimi et al., J. Immunol. 144(12):4604–4612 (1990).
Flavin et al., Transplant. Proc. 23(1):553–534 (1991).
Tolkoff-Rubin et al., J. Amer. Soc. Nephrology 2(3):820 No. 2P (1991).
Kavanaugh et al., 56th Meeting of Amer. College of Rheumatology, Oct. 13–15, Atlanta, Ga. (1992).
Boyd et al., Proc. Natl. Acad. Sci. USA 85:3095–3099 (1988).

(List continued on next page.)

Primary Examiner—Christine M. Nucker
Assistant Examiner—Thomas Cunningham
Attorney, Agent, or Firm—Sterne, Kessler, Goldstein & Fox

[57] ABSTRACT

Pharmaceutical compositions comprising antibodies to intercellular adhesion molecule-1 (ICAM-1 or CD54) are useful in methods of decreasing the severity of inflammation associated with the adhesion of leukocytes to cells bearing ICAM-1. Treatment with anti-ICAM-1 antibodies reduced the severity of inflammation associated with acute organ or tissue rejection and prolonged allograft survival time. Such compositions may optionally contain other immunsuppressive agents.

11 Claims, 25 Drawing Sheets

OTHER PUBLICATIONS

Tötterman et al., *Transplantation* 47(5):817–823 (1989).
Cooper et al., *Immunologic Diseases of the Skin*, Appleton & Lange, Chapter 51, pp. 611–619 (1991).
Meurer et al., *Immunologic Diseases of the Skin*, Appleton & Lange, chapter 32, pp. 389–397 (1991).
Alexander et al., *Immunologic Diseases of the Skin*, Appleton & Lange, Chapter 33, pp. 401–408 (1991).
Theofilopoulos, *Basic and Clinical Immunology*, Appleton & Lange, Chapter 11, pp. 128–132, (1987).
Hoffman et al., *Basic and Clinical Immunology*, Appleton & Lange, Chapter 32, pp. 598–602, (1987).
Jonker et al., *J. Autoimmun.* 1(5):399–414 (1988).
Byers et al., *Blood* 75(7):1426–1432 (1990).
Order et al., *NCI Monogr.* 3:37–41 (1987).
Order et al., *J. Clin. Oncol.* 3(12):1573–1582 (1985).
Bashir et al., *J. Neuro-Oncol.* 12:103–110 (1992).
Tolosa et al., *J. Autoimmunity* 5:107–118 (1992).
Kageshita et al., *Cancer Res.* 51:1726–1732 (1991).
Natali et al., *Cancer Res.* 50:1271–1278 (1990).
Anderson, D. C., et al., *Ann. Rev. Med.* 38:175–194 (1987).
Anderson, D. C., et al., *Fed. Proc.* 44:2671–2677 (1985).
Colonno, R. J. et al., *J. Virol.* 57:7–12 (1986).
Davignon, D. et al., *PNAS* 78:4535–4539 (1981).
Dustin, M. L., et al., J. Immunol 137:245–254, (1986).
Dustin, M. L. et al., *Immunol. Today* 9:213–215 (1988).
Dustin, M., et al., *J. Exper. Med.* 165:677–692 (1987).
Dustin, M. et al., *J. Cell Biol.* 107:321–331 (1988).
Dustin, M. et al., *J. Exp. Med.* 167:1323–1340 (1988).
Dustin, M. et al., *Nature* 341:619–624 (1989).
Fischer, A., et al., *J. Immunol.* 136:3198–3203 (1986).
Hamann et al., *J. Immunol.* 140(3):693–699 (1988).
Hildreth et al., *Science* 344:1075 1078 (1989).
Harlan, J. M., *Blood* 65(3):513–525 (1985).

```
5' GCGCCCCAGTGAGCTGAGCTCCTCTGCTACTCAGAGTGCAACCTCAGCCTCGCT                                                    57

ATG GCT CCC AGC AGC CCC CGG CCC GCA CTC CCG GCT CTG CTC GTC CTG CTC GGG GCT CTC TTC CCA GGA CCT GGC AAT GCC CAG ACA TCT    147
 M   A   P   S   S   P   R   P   A   L   P   A   L   L   V   L   L   G   A   L   F   P   G   P   G   N   A   Q   T   S     3

GTC TCC CCC TCA AAA GTC ATC CTG CCC CGG GGA GGC AGC GTG CTG GTG ACA TGC AGC ACC TCC TGT GAC CCC CAG CCC AAG TTG TTG GGC ATA    237
 V   S   P   S   K   V   I   L   P   R   G   G   S   V   L   V   T   C   S   T   S   C   D   P   Q   P   K   L   L   G   I    33

GAG ACC CCG TTG CCT AAA AAG GAG TTG CTC CTG CCT GGG AAC AAC AGG AAG GTG TAT GAA CTG AGC AAT GTG CAA GAA GAT AGC CAA CCA    327
 E   T   P   L   P   K   K   E   L   L   L   P   G   N   N   R   K   V   Y   E   L   S   N   V   Q   E   D   S   Q   P    63

ATG TGC TAT TCA AAC TGC CCT GAT GGG CAG TCA ACA GCT AAA ACC TTC CTC ACC GTG TAC TGG ACT CCA GAA CGG GTG GAA CTG GCA CCC    417
 M   C   Y   S   N   C   P   D   G   Q   S   T   A   K   T   F   L   T   V   Y   W   T   P   E   R   V   E   L   A   P    93

CTC CCC TCT TGG CAG CCA GTG GGC AAG AAC CTT ACC CTA CGC TGC CAG GTG GAG GGT GGA GCA CCC CGG GCA AAC CTC ACC GTG GTC CTG    507
 L   P   S   W   Q   P   V   G   K   N  [L   T] L   R   C   Q   V   E   G   G   A   P   R   A   N  [L   T] V   V   L   123

CTC CGT GGG GAG GAG AAG GAG CTC AAA CGG GAG CCT GCA GTC GGC GAG CCC GCC GAG GTC ACC ACC ACC GTG CTG GTG AGA GAT CAC CAT    597
 L   R   G   E   E   K   E   L   K   R   E   P   A   V   G   E   P   A   E   V   T   T   T   V   L   V   R   R   D   H   H   153

GGA GCC AAT TTC TCC TGC CGC ACT GAA CTG GAC CTG CGG CCC CAA GGG CTG GAG CTG TTT GAG AAC ACC TCG GCC CCC TAC CAG CTG CAG    687
 G   A  [N   F   S] C   R   T   E   L   D   L   R   P   Q   G   L   E   L   F   E   N  [T   S] A   P   Y   Q   L   Q    183

ACC TTT GTC CTG CCA GCG ACT CCC CAA CTT GTC CCA CCG CAG CTC GTG GAC ACG CAG CGG ACC GTG GTC TGT TCC CTG GAC    777
 T   F   V   L   P   A   T   P   P   Q   L   V   P   P   Q   L   V   D   T   Q   G   T   V   V   C   S   L   D   213
```

```
                    4                 13
       ICAM-2  E V H V R P N K L A V S Q R - S L E V N C S T
    mo ICAM-1  Q V S I H P R E A F L P Q G G S V Q V N C S S
    hu ICAM-1  Q T S V S P S K V I L P R G G S V L V T C S T
               K A                    E A
                 A G L                E

INTERCELLULAR ADHESION MOLECULES, AND THEIR BINDING LIGANDS

This invention was made in part with Government support. The Government has certain rights in this invention.

CROSS-REFERENCE TO RELATED APPLICATIONS

This Application is a continuation-in-part of U.S. patent application Ser. Nos. 07/045,963 (filed on May 4, 1987), 07/115,798 (filed on Nov. 2, 1987), 07/155,943 (filed on Feb. 16, 1988), 07/189,815 (filed on May 3, 1988), 07/250,446 (filed on Sep. 28, 1988), 07/324,481 (filed on Mar. 16, 1989), 07/373,882 (filed on Jun. 30, 1989), and 07/456,647 (filed on Dec. 22, 1989) all of which applications are incorporated herein by reference.

BACKGROUND OF THE INVENTION

1. Field of the Invention

The present invention relates to intercellular adhesion molecules such as ICAM-1 which are involved in the process through which populations of lymphocytes recognize and adhere to cellular substrates so that they may migrate to sites of inflammation and interact with cells during inflammatory reactions. The present invention additionally relates to ligand molecules capable of binding to such intercellular adhesion molecules, to a screening assay for these ligands, and to uses for the intercellular adhesion molecule, the ligand molecules, and the screening assay.

2. Description of the Related Art

Leukocytes must be able to attach to cellular substrates in order to properly defend the host against foreign invaders such as bacteria or viruses. An excellent review of the defense system is provided by Eisen, H. W., (In: *Microbiology*, 3rd Ed., Harper & Row, Philadelphia, Pa. (1980), pp. 290-295 and 381-418). They must be able to attach to endothelial cells so that they can migrate from circulation to sites of ongoing inflammation. Furthermore, they must attach to antigen-presenting cells so that a normal specific immune response can occur, and finally, they must attach to appropriate target cells so that lysis of virally-infected or tumor cells can occur.

Recently, leukocyte surface molecules involved in mediating such attachments were identified using hybridoma technology. Briefly, monoclonal antibodies directed against human T-cells (Davignon, D. et al., *Proc. Natl. Acad. Sci. USA* 78:4535-4539 (1981)) and mouse spleen cells (Springer, T. et al. *Eur. J. Immunol.* 9:301-306 (1979)) were identified which bound to leukocyte surfaces and inhibited the attachment related functions described above (Springer, T. et al., *Fed. Proc.* 44:2660-2663 (1985) The molecules identified by those antibodies were called Mac-1 and Lymphocyte Function-associated Antigen-1 (LFA-1). Mac-1 is a heterodimer found on macrophages, granulocytes and large granular lymphocytes. LFA-1 is a heterodimer found on most lymphocytes (Springer, T. A., et al. *Immunol. Rev.* 68:111-135 (1982)). These two molecules, plus a third molecule, p150, (which has a tissue distribution similar to Mac-1) play a role in cellular adhesion (Keizer, G. et al., *Eur. J. Immunol.* 15:1142-1147 (1985)).

The above-described leukocyte molecules were found to be members of a related family of glycoproteins (Sanchez-Madrid, F. et al., *J. Exper. Med.* 158:1785-1803 (1983); Keizer, G. D. et al., *Eur. J. Immunol.* 15:1142-1147 (1985)). This glycoprotein family is composed of hetero-dimers having one alpha chain and one beta chain. Although the alpha chain of each of the antigens differed from one another, the beta chain was found to be highly conserved (Sanchez-Madrid, F. et al., *J. Exper. Med.* 158:1785-1803 (1983)). The beta chain of the glycoprotein family (sometimes referred to as "CD18") was found to have a molecular weight of 95 kd whereas the alpha chains were found to vary from 150 kd to 180 kd (Springer, T., ed. *Fed. Proc.* 44:2660-2663 (1985)). Although the alpha subunits of the membrane proteins do not share the extensive homology shared by the beta subunits, close analysis of the alpha subunits of the glycoproteins has revealed that there are substantial similarities between them. Reviews of the similarities between the alpha and beta subunits of the LFA-1 related glycoproteins are provided by Sanchez-Madrid, F. et al., (*J. Exper. Med.* 158:586-602 (1983); *J. Exper. Med.* 158:1785-1803 (1983)).

A group of individuals has been identified who are unable to express normal amounts of any member of this adhesion protein family on their leukocyte cell surface (Anderson, D. C., et al., *Fed. Proc.* 44:2671-2677 (1985); Anderson, D. C., et al., *J. Infect. Dis.* 152:668-689 (1985)). Lymphocytes from these patients displayed in vitro defects similar to normal counterparts whose LFA-1 family of molecules had been antagonized by antibodies. Furthermore, these individuals were unable to mount a normal immune response due to an inability of their cells to adhere to cellular substrates (Anderson, D. C., et al., *Fed. Proc.* 44:2671-2677 (1985); Anderson, D. C., et al., *J. Infect. Dis.* 152:668-689 (1985)). These data show that immune reactions are mitigated when lymphocytes are unable to adhere in a normal fashion due to the lack of functional adhesion molecules of the LFA-1 family.

Thus, in summary, the ability of lymphocytes to maintain the health and viability of an animal requires that they be capable of adhering to other cells (such as endothelial cells). This adherence has been found to require cell-cell contacts which involve specific receptor molecules present on the cell surface of the lymphocytes. These receptors enable a lymphocyte to adhere to other lymphocytes or to endothelial, and other non-vascular cells. The cell surface receptor molecules have been found to be highly related to one another. Humans whose lymphocytes lack these cell surface receptor molecules exhibit chronic and recurring infections, as well as other clinical symptoms including defective antibody responses.

Since lymphocyte adhesion is involved in the process through which foreign tissue is identified and rejected, an understanding of this process is of significant value in the fields of organ transplantation, tissue grafting, allergy and oncology.

SUMMARY OF THE INVENTION

The present invention relates to Intercellular Adhesion Molecule-1 (ICAM-1) as well as to its functional derivatives. The invention additionally pertains to antibodies and fragments of antibodies capable of inhibiting the function of ICAM-1, and to other inhibitors of ICAM-1 function; and to assays capable of identifying such inhibitors. The invention additionally includes diagnostic and therapeutic uses for all of the above-described molecules.

In detail, the invention includes the intercellular adhesion molecule ICAM-1 or its functional derivatives, which are substantially free of natural contaminants. The invention further pertains to such molecules which are additionally capable of binding to a molecule present on the surface of a lymphocyte.

The invention further pertains to the intercellular adhesion molecule ICAM-1, and its derivatives which are detectably labeled.

The invention additionally includes a recombinant DNA molecule capable of expressing ICAM-1 or a functional derivative thereof.

The invention also includes a method for recovering ICAM-1 in substantially pure form which comprises the steps:

(a) solubilizing ICAM-1 from the membranes of cells expressing ICAM-1, to form a solubilized ICAM-1 preparation, (b) introducing the solubilized ICAM-1 preparation to an affinity matrix, the matrix containing antibody capable of binding to ICAM-1, (c) permitting the ICAM-1 to bind to the antibody of the affinity matrix, (d) removing from the matrix any compound incapable of binding to the antibody and (e) recovering the ICAM-1 in substantially pure form by eluting the ICAM-1 from the matrix.

The invention additionally includes an antibody capable of binding to a molecule selected from the group consisting of ICAM-1 and a functional derivative of ICAM-1. The invention also includes a hybridoma cell capable of producing such an antibody.

The invention further includes a hybridoma cell capable of producing the monoclonal antibody R6-5-D6.

The invention further includes a method for producing a desired hybridoma cell that produces an antibody which is capable of binding to ICAM-1, which comprises:

(a) immunizing an animal with a cell expressing ICAM-1, (b) fusing the spleen cells of the animal with a myeloma cell line, (c) permitting the fused spleen and myeloma cells to form antibody secreting hybridoma cells, and (d) screening the hybridoma cells for the desired hybridoma cell that is capable of producing an antibody capable of binding to ICAM-1.

The invention includes as well the hybridoma cell, and the antibody produced by the hybridoma cell, obtained by the above method.

The invention is also directed to a method of identifying a non-immunoglobulin antagonist of intercellular adhesion which comprises:

(a) incubating a non-immunoglobulin agent capable of being an antagonist of intercellular adhesion with a lymphocyte preparation, the lymphocyte preparation containing a plurality of cells capable of aggregating;

(b) examining the lymphocyte preparation to determine whether the presence of the agent inhibits the aggregation of the cells of the lymphocyte preparation; wherein inhibition of the aggregation identifies the agent as an antagonist of intercellular adhesion.

The invention is also directed toward a method for treating inflammation resulting from a response of the specific defense system in a mammalian subject which comprises providing to a subject in need of such treatment an amount of an anti-inflammatory agent sufficient to suppress the inflammation; wherein the anti-inflammatory agent is selected from the group consisting of: an antibody capable of binding to ICAM-1; a fragment of an antibody, the fragment being capable of binding to ICAM-1; ICAM-1; a functional derivative of ICAM-1; and a non-immunoglobulin antagonist of ICAM-1.

The invention further includes the above-described method of treating inflammation wherein the non-immunoglobulin antagonist of ICAM-1 is a non-immunoglobulin antagonist of ICAM-1 other than LFA-1.

The invention is also directed to a method of suppressing the metastasis of a hematopoietic tumor cell, the cell requiring a functional member of the LFA-1 family for migration, which method comprises providing to a patient in need of such treatment an amount of an anti-inflammatory agent sufficient to suppress the metastasis; wherein the anti-inflammatory agent is selected from the group consisting of: an antibody capable of binding to ICAM-1; a fragment of an antibody, the fragment being capable of binding to ICAM-1; ICAM-1; a functional derivative of ICAM-1; and a non-immunoglobulin antagonist of ICAM-1.

The invention further includes the above-described method of suppressing the metastasis of a hematopoietic tumor cell, wherein the non-immunoglobulin antagonist of ICAM-1 is a non-immunoglobulin antagonist of ICAM-1 other than LFA-1.

The invention also includes a method of suppressing the growth of an ICAM-1-expressing tumor cell which comprises providing to a patient in need of such treatment an amount of a toxin sufficient to suppress the growth, the toxin being selected from the group consisting of a toxin-derivatized antibody capable of binding to ICAM-1; a toxin-derivatized fragment of an antibody, the fragment being capable of binding to ICAM-1; a toxin-derivatized member of the LFA-1 family of molecules; and a toxin-derivatized functional derivative of a member of the LFA-1 family of molecules.

The invention is also directed to a method of suppressing the growth of an LFA-1-expressing tumor cell which comprises providing to a patient in need of such treatment an amount of toxin sufficient to suppress such growth, the toxin being selected from the group consisting of a toxin-derivatized ICAM-1; and a toxin-derivatized functional derivative of ICAM-1.

The invention is further directed toward a method of diagnosing the presence and location of an inflammation resulting from a response of the specific defense system in a mammalian subject suspected of having the inflammation which comprises:

(a) administering to the subject a composition containing a detectably labeled binding ligand capable of identifying a cell which expresses ICAM-1, and (b) detecting the binding ligand.

The invention additionally provides a method of diagnosing the presence and location of an inflammation resulting from a response of the specific defense system in a mammalian subject suspected of having the inflammation which comprises:

(a) incubating a sample of tissue of the subject with a composition containing a detectably labeled binding ligand capable of identifying a cell which expresses ICAM-1, and (b) detecting the binding ligand.

The invention also pertains to a method of diagnosing the presence and location of an ICAM-1-expressing tumor cell in a mammalian subject suspected of having such a cell, which comprises:

(a) administering to the subject a composition containing a detectably labeled binding ligand capable of binding to ICAM-1, the ligand being selected from the group consisting of an antibody and a fragment of an antibody, the fragment being capable of binding to ICAM-1, and (b) detecting the binding ligand.

The invention also pertains to a method of diagnosing the presence and location of an ICAM-1-expressing tumor cell in a mammalian subject suspected of having such a cell, which comprises:

(a) incubating a sample of tissue of the subject with a composition containing a detectably labeled binding ligand capable of binding ICAM-1, the ligand being selected from group consisting of antibody and a fragment of an antibody, the fragment being capable of binding to ICAM-1, and (b) detecting the binding ligand.

The invention also pertains to a method of diagnosing the presence and location of a tumor cell which expresses a member of the LFA-1 family of molecules in a subject suspected of having such a cell, which comprises:

(a) administering to the subject a composition containing a detectably labeled binding ligand capable of binding to a member of the LFA-1 family of molecules, the ligand being selected from the group consisting of ICAM-1 and a functional derivative of ICAM-1, and (b) detecting the binding ligand.

The invention also pertains to a method of diagnosing the presence and location of a tumor cell which expresses a member of the LFA-1 family of molecules in a subject suspected of having such a cell, which comprises:

(a) incubating a sample of tissue of the subject in the presence of a detectably labeled binding ligand capable of binding to a member of the LFA-1 family of molecules, the ligand being selected from the group consisting of ICAM-1 and a functional derivative of ICAM-1, and (b) detecting the binding ligand which is bound to a member of the LFA-1 family of molecules present in the sample of tissue.

The invention additionally includes a phamaceutical composition comprising:

(a) an anti-inflammatory agent selected from the group consisting of: an antibody capable of binding to ICAM-1; a fragment of an antibody, the fragment being capable of binding to ICAM-1; ICAM-1; a functional derivative of ICAM-1; and a non-immunoglobulin antagonist of ICAM-1, and (b) at least one immunosuppressive agent selected from the group consisting of: dexamethesone, azathioprine and cyclosporin A.

BRIEF DESCRIPTION OF THE FIGURES

FIG. 8 (Panels A-C) nucleotide and amino acid sequence of ICAM-1 cDNA. The first ATG is at position 58. Translated sequences corresponding to ICAM-1 tryptic peptides are underlined. The hydrophobic putative signal peptide and transmembrane sequences have a bold underline. N-linked glycosylation sites are boxed. The polyadenylation signal AATAAA at position 2976 is over-lined. The sequence shown is for the HL-60 CDNA clone. The endothelial cell CDNA was sequenced over most of its length and showed only minor differences.

FIG. 9 shows the ICAM-1 homologous domains and relationship to the immunoglobulin supergene family. Alignment of 5 homologous domains (D1-5). Two or more identical residues which aligned are boxed. Residues conserved 2 or more times in NCAM domains, as well as resides conserved in domains of the sets C2 and C1 were aligned with the ICAM-1 internal repeats. The location of the predicted $\beta$ strands in the ICAM-1 domain is marked with bars and lower case letters above the alignments, and the known location of $\beta$-strands in immunoglobulin C domains is marked with bars and capital letters below the alignment. The position of the putative disulfide bridge within ICAM-1 domains is indicated by S-S. Alignment of protein domains homologous to ICAM-1 domains; proteins were initially aligned by searching NBRF databases using the FASTP program. The protein sequences are MAG, NCAM, T cell receptor a subunit V domain, IGM$\mu$ chain and $\alpha$-1-B-glycoprotein.

FIG. 20 shows the alignment of ICAM amino-terminal domains.

DESCRIPTION OF THE PREFERRED EMBODIMENTS

Figure 1:
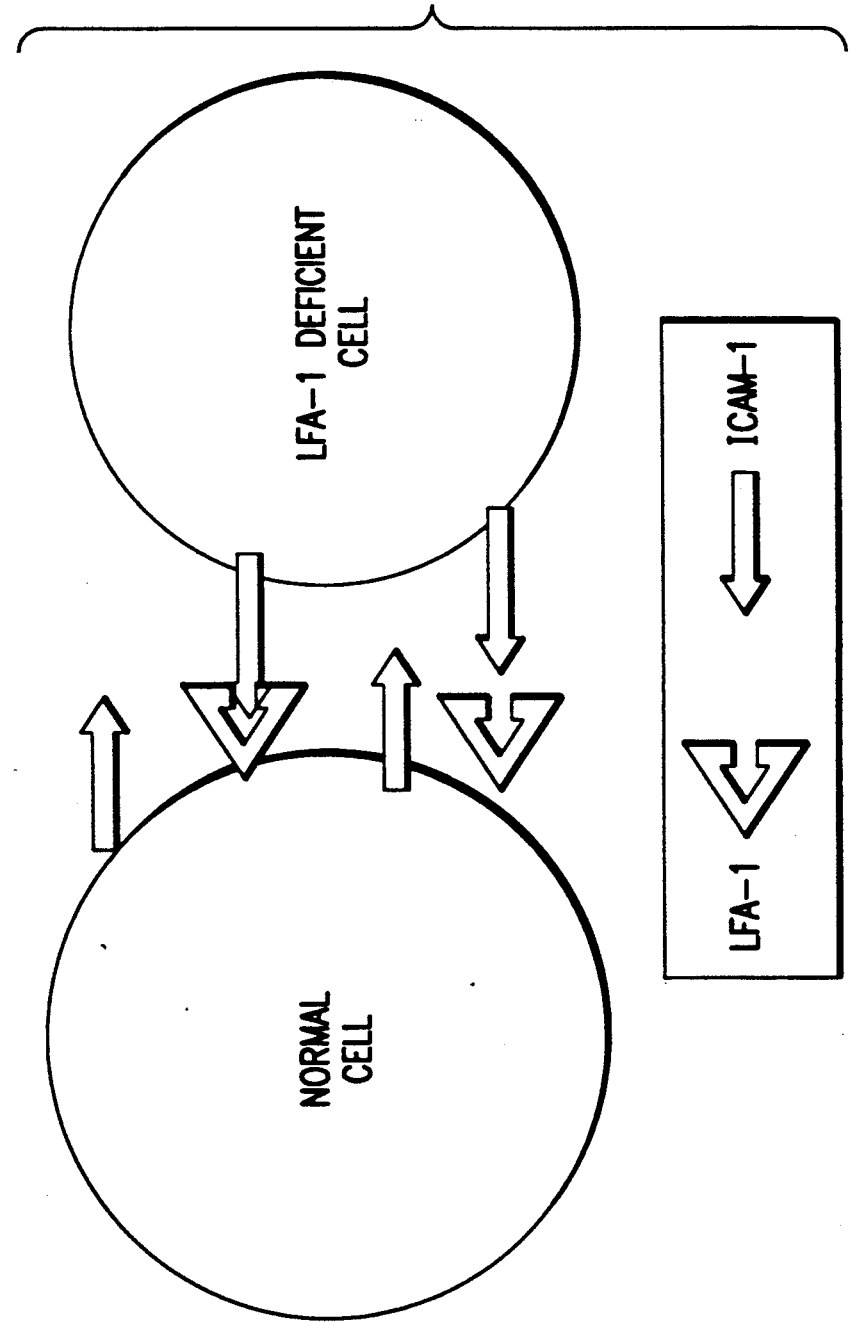
FIG. 1 shows in diagrammatic form the adhesion between a normal and an LFA-1 deficient cell.

One aspect of the present invention relates to the discovery of a natural binding ligand to LFA-1. Molecules such as those of LFA-1 family, which are involved in the process of cellular adhesion are referred to as "adhesion molecules."

The natural binding ligand of the present invention is designated "Intercellular Aadhesion Molecule-1" or "ICAM-1." ICAM-1 is a 76-97 Kd glycoprotein. ICAM-1 is not a heterodimer. The present invention is directed toward ICAM-1 and its "functional derivatives." A "functional derivative" of ICAM-1 is a compound which posesses a biological activity (either functional or structural) that is substantially similar to a biological activity of ICAM-1. The term "functional derivatives" is intended to include the "fragments," "variants," "analogs," or "chemical derivatives" of a molecule. A "fragment" of a molecule such as ICAM-1, is meant to refer to any polypeptide subset of the molecule. Fragments of ICAM-1 which have ICAM-1 activity and which are soluble (i.e not membrane bound) are especially preferred. A "variant" of a molecule such as ICAM-1 is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a molecule such as ICAM-1 is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Toxin-derivatized" molecules constitute a special class of "chemical derivatives." A "toxin-derivatized" molecule is a molecule (such as ICAM-1 or an antibody) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

A "peptidomimetic" of ICAM-1 is a functional derivative of ICAM-1 whose tertiary structure is substantially similar to the tertiary structure of ICAM-1.

An antigenic molecule such as ICAM-1, or members of the LFA-1 family of molecules are naturally expressed on the surfaces of lymphocytes. Thus, the introduction of such cells into an appropriate animal, as by intraperitoneal injection, etc., will result in the production of antibodies capable of binding to ICAM-1 or members of the LFA-1 family of molecules. If desired, the serum of such an animal may be removed and used as a source of polyclonal antibodies capable of binding these molecules. It is, however, preferable to remove splenocytes from such animals, to fuse such spleen cells with a myeloma cell line and to permit such fusion cells to form a hybridoma cell which secretes monoclonal antibodies capable of binding ICAM-1 or members of the LFA-1 family of molecules.

The hybridoma cells, obtained in the manner described above may be screened by a variety of methods to identify desired hybridoma cells that secrete antibody capable of binding either to ICAM-1 or to members of the LFA-1 family of molecules. In a preferred screening assay, such molecules are identified by their ability to inhibit the aggregation of Epstein-Barr virus-transformed cells. Antibodies capable of inhibiting such aggregation are then further screened to determine whether they inhibit such aggregation by binding to ICAM-1, or to a member of the LFA-1 family of molecules. Any means capable of distinguishing ICAM-1 from the LFA-1 family of molecules may be employed in such a screen. Thus, for example, the antigen bound by the antibody may be analyzed as by immunoprecipitation and polyacrylamide gel electrophoresis. If the bound antigen is a member of the LFA-1 family of molecules then the immunoprecipitated antigen will be found to be a dimer, whereas if the bound antigen is ICAM-1 a single molecular weight species will have been immunoprecipitated. Alternatively, it is possible to distinguish between those antibodies which bind to members of the LFA-1 family of molecules from those which bind ICAM-1 by screening for the ability of the antibody to bind to cells such as granulocytes, which express LFA-1, but not ICAM-1. The ability of an antibody (known to inhibit cellular aggregation) to bind to granulocytes indicates that the antibody is capable of binding LFA-1. The absence of such binding is indicative of an antibody capable of recognizing ICAM-1. The ability of an antibody to bind to a cell such as a granulocyte may be detected by means commonly employed by those of ordinary skill. Such means include immunoassays, cellular agglutination, filter binding studies, antibody precipitation, etc.

The anti-aggregation antibodies of the present invention may alternatively be identified by measuring their ability to differentially bind to cells which express ICAM-1 (such as activated endothelial cells), and their inability to bind to cells which fail to express ICAM-1. As will be readily appreciated by those of ordinary skill, the above assays may be modified, or performed in a different sequential order to provide a variety of potential screening assays, each of which is capable of identifying and discriminating between antibodies capable of binding to ICAM-1 versus members of the LFA-1 family of molecules.

In addition to the above-described functional derivatives of ICAM-1, other agents which may be used in accordance of the present invention in the treatment of inflammation include antibody to ICAM-1, and receptor molecules (such as LFA-1, p150, Mac-1, etc.), or fragments of such molecules, which are capable of binding to ICAM-1.

Since molecules of the CD-18 family are able to bind to ICAM-1, administration of such molecules (for example as heterodimers having both alpha and beta subunits, or as molecules composed of only an alpha, or a beta subunit, or as molecules having fragments of either or both subunits) is able to compete with (or exclude) HRV for binding to ICAM-1 present on endothelial cells.

The anti-inflammatory agents of the present invention may be obtained by natural processes (such as, for example, by inducing an animal, plant, fungi, bacteria, etc., to produce a non-immunoglobulin antagonist of ICAM-1, or by inducing an animal to produce polyclonal antibodies capable of binding to ICAM-1); by synthetic methods (such as, for example, by using the Merrifield method for synthesizing polypeptides to synthesize ICAM-1, functional derivatives of ICAM-1, or protein antagonists of ICAM-1 (either immunoglobulin or non-immunoglobulin)); by hybridoma technology (such as, for example, to produce monoclonal antibodies capable of binding to ICAM-1); or by recombinant technology (such as, for example, to produce the anti-inflammatory agents of the present invention in diverse hosts (i.e., yeast, bacteria, fungi, cultured mammalian cells, etc.), or from recombinant plasmids or viral vectors). The choice of which method to employ will depend upon factors such as convenience, desired yield, etc. It is not necessary to employ only one of the above-described methods, processes, or technologies to produce a particular anti-inflammatory agent; the above-described processes, methods, and technologies may be combined in order to obtain a particular anti-inflammatory agent.

A. Identification of the LFA-1 Binding Partner (ICAM-1)

1. Assays of LFA-1-Dependent Aggregation

Many Epstein-Barr virus-transformed cells exhibit aggregation. This aggregation can be enhanced in the presence of phorbol esters. Such homotypic aggregation (i.e., aggregation involving only one cell type) was found to be blocked by anti-LFA-1 antibodies (Rothlein, R. et al., *J. Exper. Med.* 163:1132–1149 (1986)), which reference is incorporated herein by reference). Thus, the extent of LFA-1-dependent binding may be determined by assessing the extent of spontaneous or phorbol ester-dependent aggregate formation.

An agent which interferes with LFA-1-dependent aggregation can be identified through the use of an assay capable of determining whether the agent interferes with either the spontaneous, or the phorbol ester-dependent aggregation of Epstein-Barr virus-transformed cells. Most Epstein-Barr virus-transformed cells may be employed in such an assay as long as the cells are capable of expressing the LFA-1 receptor molecule. Such cells may be prepared according to the technique of Springer, T. A. et al., *J. Exper. Med.* 160:1901–1918 (1984), which reference is herein incorporated by reference. Although any such cell may be employed in the LFA-1 dependent binding assay of the present invention, it is preferable to employ cells of the JY cell line (Terhost, C. T. et al., *Proc. Natl. Acad. Sci. USA* 73:910 (1976)). The cells may be cultivated in any suitable culture medium; however, it is most preferable to culture the cells in RMPI 1640 culture medium supplemented with 10% fetal calf serum and 50 $\mu$Ig/ml gentamycin (Gibco Laboratories, N.Y.). The cells should be cultured under conditions suitable for mammalian cell proliferation (i.e., at a temperature of generally 37° C., in an atmosphere of 5% $CO_2$, at a relative humidity of 95%, etc.).

2. LFA-1 Binds to ICAM-1

Human individuals have been identified whose lymphocytes lack the family of LFA-1 receptor molecules (Anderson, D. C. et al., *Fed. Proc.* 44:2671–2677 (1985); Anderson, D. C. et al., *J. Infect. Dis.* 152:668–689 (1985)). Such individuals are said to suffer from Leukocyte Adhesion Deficiency (LAD). EBV-transformed cells of such individuals fail to aggregate either spontaneously or in the presence of phorbol esters in the above-described aggregation assay. When such cells are mixed with LFA-1-expressing cells aggregation was observed (Rothlein, R. et al., *J. Exper. Med.* 163:1132–1149 (1986)) (FIG. 1). Importantly, these aggregates failed to form if these cells were incubated in the presence of anti-LFA-1 antibodies. Thus, although the aggregation required LFA-1, the ability of LFA-1-deficient cells to form aggregates with LFA-1-containing cells indicated that the LFA-1 binding partner was not LFA-1 but was rather a previously undiscovered cellular adhesion molecule. FIG. 1 shows the mechanism of cellular adhesion.

B. Intercellular Adhesion Molecule-1 (ICAM-1)

Figure 2:
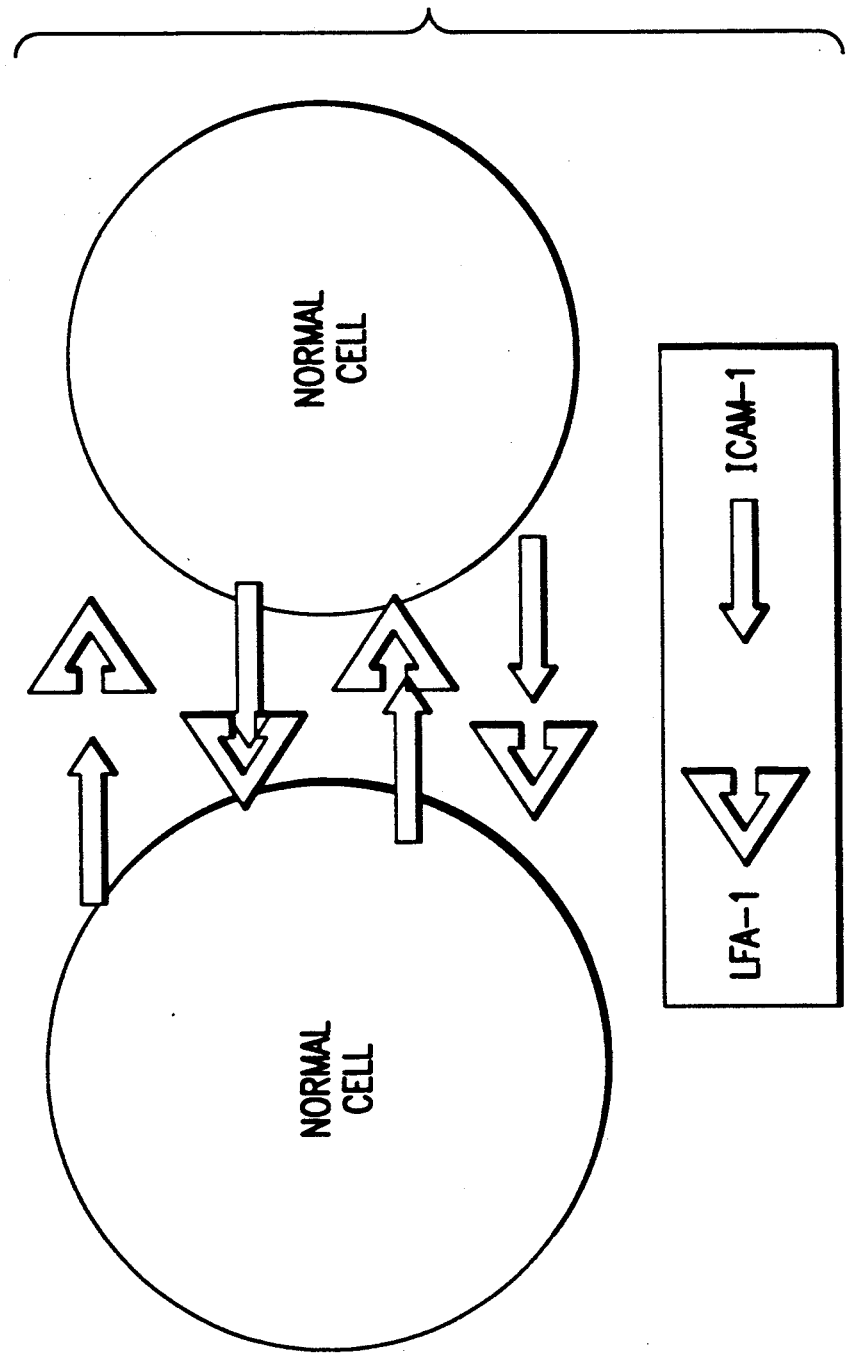
FIG. 2 shows in diagrammatic form the process of normal/normal cell adhesion.

The novel intercellular adhesion molecule ICAM-1 was first identified and partially characterized according to the procedure of Rothlein, R. et al. (*J. Immunol.* 137:1270–1274 (1986)), which reference is herein incorporated by reference. To detect the ICAM-1 molecule, monoclonal antibodies were prepared from spleen cells of mice immunized with cells from individuals genetically deficient in LFA-1 expression. Resultant antibodies were screened for their ability to inhibit the aggregation of LFA-1-expressing cells (FIG. 2). In detail, the ICAM-1 molecule, mice were immunized with EBV-transformed B cells from LAD patients which do not express the LFA-1 antigen. The spleen cells from these animals were subsequently removed, fused with myeloma cells, and allowed to become monoclonal antibody producing hybridoma cells. EBV-transformed B cells from normal individuals which express LFA-1 were then incubated in the presence of the monoclonal antibody of the hybridoma cell in order to identify any monoclonal antibody which was capable of inhibiting the phorbol ester mediated, LFA-1 dependent, spontaneous aggregation of the EBV-transformed B cells. Since the hybridoma cells were derived from cells which had never encountered the LFA-1 antigen no monoclonal antibody to LFA-1 was produced. Hence, any antibody found to inhibit aggregation must be capable of binding to an antigen that, although not LFA-1, participated in the LFA-1 adhesion process. Although any method of obtaining such monoclonal antibodies may be employed, it is preferable to obtain ICAM-1-binding monoclonal antibodies by immunizing BALB/C mice using the routes and schedules described by Rothlein, R. et al. (*J. Immunol.* 137: 1270–1274 (1986) with Epstein-Barr virus-transformed peripheral blood mononuclear cells from an LFA-1-deficient individuals. Such cells are disclosed by Springer, T. A., et al,. (*J. Exper. Med.* 160:1901–1918 (1984)).

In a preferred method for the generation and detection of antibodies capable of binding to ICAM-1, mice are immunized with either EBV-transformed B cells which express both ICAM-1 and LFA-1 or more preferably with TNF-activated endothelial cells which express ICAM-1 but not LFA-1. In a most preferred method for generating hybridoma cells which produce anti-ICAM-1 antibodies, a Balb/C mouse was sequentially immunized with JY cells and with differentiated U937 cells (ATCC CRL-1593). The spleen cells from such animals are removed, fused with myeloma cells and permitted to develop into antibody-producing hybridoma cells. The antibodies are screened for their ability to inhibit the LFA-1 dependent, phorbol ester induced aggregation of an EBV transformed cell line, such as JY cells, that expresses both the LFA-1 receptor and ICAM-1. As shown by Rothlein, R., et al., (*J. Immunol.* 137:1270–1274 (1987)), antibodies capable of inhibiting such aggregation are then tested for their ability to inhibit the phorbol ester induced aggregation of a cell line, such as SKW3 (Dustin, M., et al., *J. Exper. Med.* 165:672–692 (1987)) whose ability to spontaneously aggregate in the presence of a phorbol ester is inhibited by antibody capable of binding LFA-1 but is not inhibited by anti-ICAM-1 antibodies. Antibodies capable of inhibiting the phorbol ester induced aggregation of cells such as JY cells, but incapable of inhibiting the phorbol ester induced aggregation of cells such as SKW3 cells are probably anti-ICAM-1 antibodies. Alternatively, antibodies that are capable of binding to ICAM-1 may be identified by screening for antibodies which are capable of inhibiting the LFA-1 dependent aggregation of LFA-expression cells (such as JY cells) but are incapable of binding to cells that express LFA-1 but little or no ICAM-1 (such as normal granulocytes) or are capable of binding to cells that express ICAM-1 but not LFA-1 (such as TNF-activated endothelial cells). Another alternative is to immunoprecipitate from cells expressing ICAM-1, LFA-1, or both, using antibodies that inhibit the LFA-1 dependent aggregation of cells, such as JY cells, and through SDS-PAGE or an equivalent method determine some molecular characteristic of the molecule precipitated with the antibody. If the characteristic is the same as that of ICAM-1 then the antibody can be assumed to be an anti-ICAM-1 antibody.

Using monoclonal antibodies prepared in the manner described above, the ICAM-1 cell surface molecule was purified, and characterized. ICAM-1 was purified from human cells or tissue using monoclonal antibody affinity chromatography. In such a method, a monoclonal antibody reactive with ICAM-1 is coupled to an inert column matrix. Any method of accomplishing such coupling may be employed; however, it is preferable to use the method of Oettgen, H. C. et al., *J. Biol. Chem.* 259:12034 (1984)). When a cellular lysate is passed through the matrix the ICAM-1 molecules present are adsorbed and retained by the matrix. By altering the pH or the ion concentration of the column, the bound ICAM-1 molecules may be eluted from the column. Although any suitable matrix can be employed, it is preferable to employ sepharose (Pharmacia) as the matrix material. The formation of column matrices, and their use in protein purification are well known in the art.

In a manner understood by those of ordinary skill, the above-described assays may be used to identify compounds capable of attenuating or inhibiting the rate or extent of cellular adhesion.

ICAM-1 is a cell surface glycoprotein expressed on non-hematopoietic cells such as vascular endothelial cells, thymic epithelial cells, certain other epithelial cells, and fibroblasts, and on hematopoietic cells such as tissue macrophages, mitogen-stimulated T lymphocyte blasts, and germinal centered B cells and dendritic cells in tonsils, lymph nodes, and Peyer's patches. ICAM-1 is highly expressed on vascular endothelial cells in T cell areas in lymph nodes and tonsils showing reactive hyperplasia. ICAM-1 is expressed in low amounts on peripheral blood lymphocytes. Phorbol ester-stimulated differentiation of some myelomonocytic cell lines greatly increases ICAM-1 expression. Thus, ICAM-1 is preferentially expressed at sites of inflammation, and is not generally expressed by quiescent cells. ICAM-1 expression on dermal fibroblasts is increased threefold to fivefold by either interleukin 1 or gamma interferon at levels of 10 U/ml over a period of 4 or 10 hours, respectively. The induction is dependent on protein and mRNA synthesis and is reversible.

ICAM-1 displays molecular weight heterogeneity in different cell types with a molecular weight of 97 kd on fibroblasts, 114 kd on the myelomonocytic cell line U937, and 90 kd on the B lymphoblastoid cell JY. ICAM-1 biosynthesis has been found to involve an approximately 73 kd intracellular precursor. The non-N-glycosylated form resulting from tunicamycin treatment (which inhibits glycosylation) has a molecular weight of 55 kd.

ICAM-1 isolated from phorbol ester stimulated U937 cells or from fibroblast cells yields an identical major product having a molecular weight of 60 kd after chemical deglycosylation. ICAM-1 monoclonal antibodies interfere with the adhesion of phytohemagglutinin blasts to LFA-1 deficient cell lines. Pretreatment of fibroblasts, but not lymphocytes, with monoclonal antibodies capable of binding ICAM-1 inhibits lymphocyte-fibroblast adhesion. Pretreatment of lymphocytes, but not fibroblasts, with antibodies against LFA-1 has also been found to inhibit lymphocyte-fibroblast adhesion.

ICAM-1 is, thus, the binding ligand of the CD 18 complex on leukocytes. It is inducible on fibroblasts and endothelial cells in vitro by inflammatory mediators such as IL-1, gamma interferon and tumor necrosis factor in a time frame consistent with the infiltration of lymphocytes into inflammatory lesions in vivo (Dustin, M. L., et. al., *J. Immunol* 137:245-254, (1986); Prober, J. S., et. al., *J. Immunol* 137:1893-1896, (1986)). Further ICAM-1 is expressed on non-hematopoietic cells such as vascular endothelial cells, thymic epithelial cells, other epithelial cells, and fibroblasts and on hematopoietic cells such as tissue macophages, mitogen-stimulated T lymphocyte blasts, and germinal center B-cells and dendritic cells in tonsils, lymph nodes and Peyer's patches (Dustin, M. L., et. al., *J. Immunol* 137:245-254, (1986)). ICAM-1 is expressed on keratinocytes in benign inflammatory lesions such as allergic eczema, lichen planus, exanthema, urticaria and bullous diseases. Allergic skin reactions provoked by the application of a hapten on the skin to which the patient is allergic also revealed a heavy ICAM-1 expression on the keratinocytes. On the other hand toxic patches on the skin did not reveal ICAM-1 expression on the keratinocytes. ICAM-1 is present on keratinocytes from biopsies of skin lesions from various dermatological disorders and ICAM-1 expression is induced on lesions from allergic patch tests while keratinocytes from toxic patch test lesions failed to express ICAM-1.

ICAM-1 is, therefore, a cellular substrate to which lymphocytes can attach, so that the lymphocytes may migrate to sites of inflammation and/or carry out various effector functions contributing to this inflammation. Such functions include the production of antibody, lysis of virally infected target cells, etc. The term "inflammation," as used herein, is meant to include reactions of the specific and non-specific defense systems. As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases, delayed type hypersensitivity response mediated by T-cells (as seen, for example in individuals who test "positive" in the Mantaux test), etc.

A "non-specific defense system reaction" is a response mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: asthma; adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; and cytokine-induced toxicity.

In accordance with the present invention, ICAM-1 functional derivatives, and especially such derivatives which comprise fragments or mutant variants of ICAM-1 which possess domains 1, 2 and 3 can be used in the treatment or therapy of such reactions of the non-specific defense system. More preferred for such treatment or therapy are ICAM-1 fragments or mutant variants which contain domain 2 of ICAM-1. Most preferred for such treatment or therapy are ICAM-1 fragments or mutant variants which contain domain 1 of ICAM-1.

Functional derivatives of ICAM-1, or a member of the CD18 family, having up to about 100 residues may be conveniently prepared by in vitro synthesis. If desired, such fragments may be modified by reacting targeted amino acid residues of the purified or crude protein with an organic derivatizing agent that is capable of reacting with selected side chains or terminal residues. The resulting covalent derivatives may be used to identify residues important for biological activity. In the embodiments listed below, this aspect of the invention is described with reference to the functional derivatives of ICAM-1. Such methods may also be employed to produce functional derivatives of any member of the CD18 family of molecules.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; 0-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels, into tyrosyl residues by reaction with aromatic diazonium compounds or tetranitromethane. Most commonly, N-acetylimidizol and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking an ICAM-1 functional derivative molecule to a water-insoluble support matrix or surface for use in the method for cleaving an ICAM-1 functional derivatives fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Functional derivatives of ICAM-1 having altered amino acid sequences can also be prepared by mutations in the DNA. The nucleotide sequence which encodes the ICAM-1 gene is shown in FIG. 8. Such variants include, for example, deletions from, or insertions or substitutions of, residues within the amino acid sequence shown in FIG. 8. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary MRNA structure (see EP Patent Application Publication No. 75,444).

At the genetic level, these functional derivatives ordinarily are prepared by site-directed mutagenesis of nucleotides in the DNA encoding the ICAM-1 molecule, thereby producing DNA encoding the functional derivative, and thereafter expressing the DNA in recombinant cell culture. The functional derivatives typically exhibit the same qualitative biological activity as the naturally occurring analog. They may, however, differ substantially in such characteristics with respect to the normally produced ICAM-1 molecule.

While the site for introducing an amino acid sequence variation is predetermined, the mutation per se need not be predetermined. For example, to optimize the performance of a mutation at a given site, random mutagenesis may be conducted at the target codon or region and the expressed ICAM-1 functional derivatives screened for the optimal combination of desired activity. Techniques for making substitution mutations at predetermined sites in DNA having a known sequence are well known, for example, site-specific mutagenesis.

Preparation of an ICAM-1 functional derivative molecule in accordance herewith is preferably achieved by site-specific mutagenesis of DNA that encodes an earlier prepared functional derivatives or a nonvariant version of the protein. Site-specific mutagenesis allows the production of ICAM-1 functional derivatives through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as JM101 cells, and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete ICAM-1 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the ICAM-1 functional derivative from recombinant hosts.

The third group of functional derivatives are those in which at least one amino acid residue in the ICAM-1 molecule, and preferably, only one, has been removed and a different residue inserted in its place. Such substitutions preferably are made in accordance with the following Table when it is desired to modulate finely the characteristics of the ICAM-1 molecule.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ICAM-1 molecule. However, when it is difficult to predict the exact effect of the substitution, deletion, or insertion in advance of doing so, one skilled in the art will appreciate that the effect will be evaluated by routine screening assays. For example, a functional derivative typically is made by site-specific mutagenesis of the native ICAM-1 molecule-encoding nucleic acid, expression of the variant nucleic acid in recombinant cell culture, and, optionally, purification from the cell culture, for example, by immunoaffinity adsorption on an anti-ICAM-1 molecule antibody column (to absorb the functional derivative by binding it to at least one remaining immune epitope).

The activity of the cell lysate or purified ICAM-1 molecule functional derivative is then screened in a suitable screening assay for the desired characteristic. For example, a change in the immuno-logical character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

C. Cloning of the ICAM-1 Gene

Any of a variety of procedures may be used to clone the ICAM-1 gene. One such method entails analyzing a shuttle vector library of cDNA inserts (derived from an ICAM-1 expressing cell) for the presence of an insert which contains the ICAM-1 gene. Such an analysis may be conducted by transfecting cells with the vector and then assaying for ICAM-1 expression. The preferred method for cloning this gene entails determining the amino acid sequence of the ICAM-1 molecule. To accomplish this task ICAM-1 protein may be purified and analyzed by automated sequenators. Alternatively, the molecule may be fragmented as with cyanogen bromide, or with proteases such as papain, chymotrypsin or trypsin (Oike, Y. et al., *J. Biol. Chem.* 257:9751-9758 (1982); Liu, C. et al., *Int. J. Pept. Protein Res.* 21:209-215 (1983)). Although it is possible to determine the entire amino acid sequence of ICAM-1, it is preferable to determine the sequence of peptide fragments of the molecule. If the peptides are greater than 10 amino acids long, the sequence information is generally sufficient to permit one to clone a gene such as the gene for ICAM-1.

The sequence of amino acid residues in a peptide is designated herein either through the use of their commonly employed 3-letter designations or by their single-letter designations. A listing of these 3-letter and 1-letter designations may be found in textbooks such as *Biochemistry*, Lehninger, A., Worth Publishers, New York, N.Y. (1970). When such a sequence is listed vertically, the amino terminal residue is intended to be at the top of the list, and the carboxy terminal residue of the peptide is intended to be at the bottom of the list. Similarly, when listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence. As a purely illustrative example, the amino acid sequence designated:

-Gly-Ala-Ser-Pheindicates that an Ala residue is linked to the carboxy group of Gly, and that a Ser residue is linked to the carboxy group of the Ala residue and to the amino group of a Phe residue. The designation further indicates that the amino acid sequence contains the tetrapeptide Gly-Ala-Ser-Phe. The designation is not intended to limit the amino acid sequence to this one tetrapeptide, but is intended to include (1) the tetrapeptide having one or more amino acid residues linked to either its amino or carboxy end, (2) the tetrapeptide having one or more amino acid residues linked to both its amino and its carboxy ends, (3) the tetrapeptide having no additional amino acid residues.

Once one or more suitable peptide fragments have been sequenced, the DNA sequences capable of encoding them are examined. Because the genetic code is degenerate, more than one codon may be used to encode a particular amino acid (Watson, J. D., *In: Molecular Biology of the Gene*, 3rd Ed., W. A. Benjamin, Inc., Menlo Park, Calif. (1977), pp. 356-357). The peptide fragments are analyzed to identify sequences of amino acids which may be encoded by oligonucleotides having the lowest degree of degeneracy. This is preferably accomplished by identifying sequences that contain amino acids which are encoded by only a single codon. Although occasionally such amino acid sequences may be encoded by only a single oligonucleotide, frequently the amino acid sequence can be encoded by any of a set of similar oligonucleotides. Importantly, whereas all of the members of the set contain oligonucleotides which are capable of encoding the peptide fragment and, thus, potentially contain the same nucleotide sequence as the gene which encodes the peptide fragment, only one member of the set contains a nucleotide sequence that is identical to the nucleotide sequence of this gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

In a manner exactly analogous to that described above, one may employ an oligonucleotide (or set of oligonucleotides) which have a nucleotide sequence that is complementary to the loigonucleotide sequence or set of sequences that is capable of encoding the peptide fragment.

A suitable oligonucleotide, or set of oligonucleotides which is capable of encoding a fragment of the ICAM-1 gene (or which is complementary to such an oligonucleotide, or set of oligonucleotides) is identified (using the above-described procedure), synthesized, and hybridized, by means well known in the art, against a DNA or, more preferably, a CDNA preparation derived from human cells which are capable of expressing ICAM-1 gene sequences. Techniques of nucleic acid hybridization are disclosed by Maniatis, T. et al., *In: Molecular Cloning, a Laboratory Manual*, Coldspring Harbor, N.Y. (1982), and by Haymes, B. D. et al., *In: Nucleic Acid Hybrization, a Practical Approach*, IRL Press, Washington, D.C. (1985), which references are herein incorporated by reference. The source of DNA or CDNA used will preferably have been enriched for ICAM-1 sequences. Such enrichment can most easily be obtained from CDNA obtained by extracting RNA from cells cultured under conditions which induce ICAM-1 synthesis (such as U937 grown in the presence of phorbol esters, etc.).

Techniques such as, or similar to, those described above have successfully enabled the cloning of genes for human aldehyde dehydrogenases (Hsu, L. C. et al., *Proc. Natl. Acad. Sci. USA* 82:3771-3775 (1985)), fibronectin (Suzuki, S. et al., *Eur. Mol. Biol. Organ. J.* 4:2519-2524 (1985)), the human estrogen receptor gene (Walter, P. et al., *Proc. Natl. Acad. Sci. USA* 82:7889-7893 (1985)), tissue-type plasminogen activator (Pennica, D. et al., *Nature* 301:214-221 (1983)) and human term placental alkaline phosphatase complementary DNA (Kam, W. et al., *Proc. Natl. Acad. Sci. USA* 82:8715-8719 (1985)).

In a preferred alternative way of cloning the ICAM-1 gene, a library of expression vectors is prepared by cloning DNA or, more preferably CDNA, from a cell capable of expressing ICAM-1 into an expression vector. The library is then screened for members capable of expressing a protein which binds to anti-ICAM-1 antibody, and which has a nucleotide sequence that is capable of encoding polypeptides that have the same amino acid sequence as ICAM-1 or fragments of ICAM-1.

The cloned ICAM-1 gene, obtained through the methods described above, may be operably linked to an expression vector, and introduced into bacterial, or eukaryotic cells to produce ICAM-1 protein. Techniques for such manipulations are disclosed by Maniatis, T. et al., supra, and are well known in the art.

D. Uses of Assays of LFA-1 Dependent Aggregation

The above-described assay, capable of measuring LFA-1 dependent aggregation, may be employed to identify agents which act as antagonists to inhibit the extent of LFA-1 dependent aggregation. Such antagonists may act by impairing the ability of LFA-1 or of ICAM-1 to mediate aggregation. Thus, such agents include immunoglobulins such as an antibody capable of binding to either LFA-1 or ICAM-1. Additionally, non-immunoglobulin (i.e., chemical) agents may be examined, using the above-described assay, to determine whether they are antagonists of LFA-1 aggregation.

E. Uses of Antibodies Capable of Binding to ICAM-1 Receptor Proteins

1. Anti-Inflammatory Agents

Monoclonal antibodies to members of the CD 18 complex inhibit many adhesion dependent functions of leukocytes including binding to endothelium (Haskard, D., et al., *J. Immunol.* 137:2901–2906 (1986)), homotypic adhesions (Rothlein, R., et al., *J. Exp. Med.* 3:1132–1149 (1986)), antigen and mitogen induced proliferation of lymphocytes (Davignon, D., et al., *Proc. Natl. Acad. Sci., USA* 78:4535–4539 (1981)), antibody formation (Fischer, A., et al., *J. Immunol.* 136:3198–3203 (1986)), and effector functions of all leukocytes such as lytic activity of cytotoxic T cells (Krensky, A. M., et al., *J. Immunol.* 132:2180–2182 (1984)), macrophages (Strassman, G., et al., *J. Immunol.* 136:4328–4333 (1986)), and all cells involved in antibody-dependent cellular cytotoxicity reactions (Kohl, S., et al., *J. Immunol.* 133:2972–2978 (1984)). In all of the above functions, the antibodies inhibit the ability of the leukocyte to adhere to the appropriate cellular substrate which in turn inhibits the final outcome. Although both polyclonal and monoclonal antibodies may be employed in accordance with the invention, monoclonal antibodies are especially preferred for such use.

As discussed above, the binding of ICAM-1 molecules to the members of LFA-1 family of molecules is of central importance in cellular adhesion. Through the process of adhesion, lymphocytes are capable of continually monitoring an animal for the presence of foreign antigens. Although these processes are normally desirable, they are also the cause of organ transplant rejection, tissue graft rejection and many autoimmune diseases. Hence, any means capable of attenuating or inhibiting cellular adhesion would be highly desirable in recipients of organ transplants, tissue grafts or autoimmune patients.

Monoclonal and polyclonal antibodies capable of binding to ICAM-1 are highly suitable as anti-inflamatory agents in a mammalian subject. Monoclonal antibodies are especially preferred for such use. Significantly, such agents differ from general anti-inflammatory agents in that they are capable of selectively inhibiting adhesion, and do not offer other side effects such as nephrotoxicity which are found with conventional agents. Monoclonal antibodies capable of binding to ICAM-1 can therefore be used to prevent organ or tissue rejection, or modify autoimmune responses without the fear of such side effects, in the mammalian subject.

Importantly, the use of monoclonal antibodies capable of recognizing ICAM-1 may permit one to perform organ transplants even between individuals having HLA mismatch.

As indicated above, both polyclonal and monoclonal antibodies may be employed in accordance with the present invention. Of special interest to the present invention are antibodies to ICAM-1 (or their functional derivatives), or to members of the CD18 family (or their functional derivatives), which are produced in humans, or are "humanized" (i.e. non-immunogenic in a human) by recombinant or other technology. Such antibodies are the equivalents of the monoclonal and polyclonal antibodies disclosed herein, but are less immunogenic, and are better tolerated by the patient.

Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl.Cancer Inst.* 80:1553–1559 (1988); all of which references are incorporated herein by reference). General reviews of "humanized" chimeric antibodies are provided by Morrison, S. L. (*Science,* 229:1202–1207 (1985)) and by Oi, V. T. et al., *BioTechniques* 4:214 (1986); which references are incorporated herein by reference).

Suitable "humanized" antibodies can be alternatively produced by CDR or CEA substitution (Jones, P. T. et al., *Nature* 321:552–525 (1986); Verhoeyan et al., *Science* 239:1534 (1988); Bsidler, C. B. et al., *J. Immunol.* 141:4053–4060 (1988); all of which references are incorporated herein by reference).

2. Suppressors of Delayed Type Hypersensitivity Reaction

Since ICAM-1 molecules are expressed mostly at sites of inflammation, such as those sites involved in delayed type hypersensitivity reaction, antibodies (especially monoclonal antibodies) capable of binding to ICAM-1 molecules have therapeutic potential in the attenuation or elimination of such reactions. This potential therapeutic use may be exploited in either of two manners. First, a composition containing a monoclonal antibody against ICAM-1 may be administered to a patient experiencing delayed type hypersensitivity reaction. For example, such compositions might be provided to a individual who had been in contact with antigens such as poison ivy, poison oak, etc. In the second embodiment, the monoclonal antibody capable of binding to ICAM-1 is administered to a patient in conjunction with an antigen in order to prevent a subsequent inflammatory reaction. Thus, the additional administration of an antigen with an ICAM-1-binding monoclonal antibody may temporarily tolerize an individual to subsequent presentation of that antigen.

3. Therapy for Chronic Inflammatory Disease

Since LAD patients that lack LFA-1 do not mount an inflammatory response, it is believed that antagonism of LFA-1's natural ligand, ICAM-1, will also inhibit an inflammatory response. The ability of antibodies against ICAM-1 to inhibit inflammation provides the basis for their therapeutic use in the treatment of chronic inflammatory diseases and autoimmune diseases such as lupus erythematosus, autoimmune thyroiditis, experimental allergic encephalomyelitis (EAE), multiple sclerosis, some forms of diabetes Reynaud's syndrome, rheumatoid arthritis, etc. Such antibodies may also be employed as a therapy in the treatment of psoriasis. In general, the monoclonal antibodies capable of binding to ICAM-1 may be employed in the treatment of those diseases currently treatable through steroid therapy.

4. Diagnostic and Prognostic Applications

Since ICAM-1 is expressed mostly at sites of inflammation, monoclonal antibodies capable of binding to ICAM-1 may be employed as a means of imaging or visualizing the sites of infection and inflammation in a patient. In such a use, the monoclonal antibodies are detectably labeled, through the use of radioisotopes, affinity labels (such as biotin, avidin, etc.) fluorescent labels, paramagnetic atoms, etc. Procedures for accomplishing such labeling are well known to the art. Clinical application of antibodies in diagnostic imaging are reviewed by Grossman, H. B., *Urol. Clin. North Amer.* 13:465-474 (1986)), Unger, E. C. et al., *Invest. Radiol.* 20:693-700 (1985)), and Khaw, B. A. et al., *Science* 209:295-297 (1980)).

The presence of inflammation may also be detected through the use of binding ligands, such as MRNA, CDNA, or DNA which bind to ICAM-1 gene sequences, or to ICAM-1 MRNA sequences, of cells which express ICAM-1. Techniques for performing such hybridization assays are described by Maniatais, T. (supra).

The detection of foci of such detectably labeled antibodies is indicative of a site of inflammation or tumor development. In one embodiment, this examination for inflammation is done by removing samples of tissue or blood and incubating such samples in the presence of the detectably labeled antibodies. In a preferred embodiment, this technique is done in a non-invasive manner through the use of magnetic imaging, fluorography, etc. Such a diagnostic test may be employed in monitoring organ transplant recipients for early signs of potential tissue rejection. Such assays may also be conducted in efforts to determine an individual's predilection to rheumatoid arthritis or other chronic inflammatory diseases.

5. Adjunct to the Introduction of Antigenic Material Administered for Therapeutic or Diagnostic Purposes Immune responses to therapeutic or diagnostic agents such as, for example, bovine insulin, interferon, tissue-type plasminogen activator or murine monoclonal antibodies substantially impair the therapeutic or diagnostic value of such agents, and can, in fact, causes diseases such as serum sickness. Such a situation can be remedied through the use of the antibodies of the present invention. In this embodiment, such antibodies would be administered in combination with the therapeutic or diagnostic agent. The addition of the antibodies prevents the recipient from recognizing the agent, and therefore prevents the recipient from initiating an immune response against it. The absence of such an immune response results in the ability of the patient to receive additional administrations of the therapeutic or diagnostic agent.

F. Uses of Intercellular Adhesion Molecule-1 (ICAM-1)

ICAM-1 is a binding partner of LFA-1. As such, ICAM-1 or its functional derivatives may be employed interchangeably with antibodies capable of binding to LFA-1 in the treatment of disease. Thus, in solubilized form, such molecules may be employed to inhibit inflammation, organ rejection, graft rejection, etc. ICAM-1, or its functional derivatives may be used in the same manner as anti-ICAM antibodies to decrease the immunogenicity of therapeutic or diagnostic agents.

ICAM-1, its functional derivatives, and its antagonists may be used to block the metastasis or proliferation of tumor cells which express either ICAM-1 or LFA-1 on their surfaces. A variety of methods may be used to accomplish such a goal. For example, the migration of hematopoietic cells requires LFA-1-ICAM-1 binding. Antagonists of such binding therefore suppress this migration and block the metastasis of tumor cells of leukocyte lineage. Alternatively, toxin-derivatized molecules, capable of binding either ICAM-1 or a member of the LFA-1 family of molecules, may be administered to a patient. When such toxin-derivatized molecules bind to tumor cells that express ICAM-1 or a member of the LFA-1 family of molecules, the presence of the toxin kills the tumor cell thereby inhibiting the proliferation of the tumor.

G. Uses of Non-Immunoglobulin Antagonists of ICAM-1 Dependent Adhesion

ICAM-1-dependent adhesion can be inhibited by non-immunoglobulin antagonists which are capable of binding to either ICAM-1 or to LFA-1. One example of a non-immunoglobulin antagonist of ICAM-1 is LFA-1. An example of a non-immunoglobulin antagonist which binds to LFA-1 is ICAM-1. Through the use of the above-described assays, additional non-immunoglobulin antagonists can be identified and purified.

One especially preferred class of non-immunological antagonists comprise soluble derivatives of ICAM-1, CD11a, CD11b, CD11c, CD18 molecules, or of the CD11a/CD18, CD11b/CD18, or CD11c/CD18 heterodimers. The soluble derivatives referred to above are derivatives which are not bound to a membrane of a cell. Such derivatives may comprise truncated molecules which lack a transmembrane domain. Alternatively, they may comprise mutant forms of the natural molecules which lack the capacity to be bound (or stably bound) to the membrane of a cell even though they contain a transmembrane domain. Soluble derivatives of ICAM-1 and their preparation are disclosed by Marlin, S. D. et al., *Nature* 344:70-72 (1990), which reference is incorporated herein by reference). Among the preferred functional derivatives of the present invention are soluble fragments of the ICAM-1 molecule which contain domains 1, 2, and 3 of ICAM-1. More preferred are soluble fragments of the ICAM-1 molecule which contain domains 1 and 2 of ICAM-1. Most preferred are soluble fragments of the ICAM-1 molecule which contain domain 1 of ICAM-1.

Non-immunoglobulin antagonists of ICAM-1 dependent adhesion may be used for the same purpose as antibodies to LFA-1 or antibodies to ICAM-1.

H. Administration of the Compositions of the Present Invention

The therapeutic effects of ICAM-1 may be obtained by providing to a patient the entire ICAM-1 molecule, or any therapeutically active peptide fragments thereof.

ICAM-1 and its functional derivatives may be obtained either synthetically, through the use of recombinant DNA technology, or by proteolysis. The therapeutic advantages of ICAM-1 may be augmented through the use of functional derivatives of ICAM-1 possessing additional amino acid residues added to enhance coupling to carrier or to enhance the activity of the ICAM-1. The scope of the present invention is further intended to include functional derivatives of ICAM-1 which lack certain amino acid residues, or which contain altered amino acid residues, so long as such derivatives exhibit the capacity to affect cellular adhesion.

Both the antibodies of the present invention and the ICAM-1 molecule disclosed herein are said to be "substantially free of natural contaminants" if preparations which contain them are substantially free of materials with which these products are normally and naturally found.

The present invention extends to antibodies, and biologically active fragments thereof, (whether polyclonal or monoclonal) which are capable of binding to ICAM-1. Such antibodies may be produced either by an animal, or by tissue culture, or recombinant DNA means.

In providing a patient with antibodies, or fragments thereof, capable of binding to ICAM-1, or when providing ICAM-1 (or a fragment, variant, or derivative thereof) to a recipient patient, the dosage of administered agent will vary depending upon such factors as the patient's age, weight, height, sex, general medical condition, previous medical history, etc. In general, it is desirable to provide the recipient with a dosage of antibody which is in the range of from about 1 pg/kg to 10 mg/kg (body weight of patient), although a lower or higher dosage may be administered. When providing ICAM-1 molecules or their functional derivatives to a patient, it is preferable to administer such molecules in a dosage which also ranges from about 1 pg/kg to 10 mg/kg (body weight of patient) although a lower or higher dosage may also be administered. As discussed below, the therapeutically effective dose can be lowered if the anti-ICAM-1 antibody is additionally administered with an anti-LFA-1 antibody. As used herein, one compound is said to be additionally administered with a second compound when the administration of the two compounds is in such proximity of time that both compounds can be detected at the same time in the patient's serum.

Both the antibody capable of binding to ICAM-1 and ICAM-1 itself may be administered to patients intravenously, intramuscularly, subcutaneously, enterally, or parenterally. When administering antibody or ICAM-1 by injection, the administration may be by continuous infusion, or by single or multiple boluses.

The anti-inflammatory agents of the present invention are intended to be provided to recipient subjects in an amount sufficient to suppress inflammation. An amount is said to be sufficient to "suppress" inflammation if the dosage, route of administration, etc. of the agent are sufficient to attenuate or prevent inflammation.

Anti-ICAM-1 antibody, or a fragment thereof, may be administered either alone or in combination with one or more additional immunosuppressive agents (especially to a recipient of an organ or tissue transplant). The administration of such compound(s) may be for either a "prophylactic" or "therapeutic" purpose. When provided prophylactically, the immunosuppressive compound(s) are provided in advance of any inflammatory response or symptom (for example, prior to, at, or shortly after) the time of an organ or tissue transplant but in advance of any symptoms of organ rejection). The prophylactic administration of the compound(s) serves to prevent or attenuate any subsequent inflammatory response (such as, for example, rejection of a transplanted organ or tissue, etc.). When provided therapeutically, the immunosuppressive compound(s) is provided at (or shortly after) the onset of a symptom of actual inflammation (such as, for example, organ or tissue rejection). The therapeutic administration of the compound(s) serves to attenuate any actual inflammation (such as, for example, the rejection of a transplanted organ or tissue). The anti-inflammatory agents of the present invention may, thus, be provided either prior to the onset of inflammation (so as to suppress an anticipated inflammation) or after the initiation of inflammation.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The antibody and ICAM-1 molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of anti-ICAM antibody or ICAM-1 molecule, or their functional derivatives, together with a suitable amount of carrier vehicle.

Additional pharmaceutical methods may be employed to control the duration of action. Control release preparations may be achieved through the use of polymers to complex or absorb anti-ICAM-1 antibody or ICAM-1, or their functional derivatives. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate anti-ICAM-1 antibody or ICAM-1 molecules, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Culturing of Mammalian Cells

In general, the EBV-transformed and hybridoma cells of the present invention were maintained in RMPI 1640 culture medium, supplemented with 20 mM L-glutamine, 50 μg/ml gentamicin, and 10% fetal bovine (or fetal calf) sera. Cells were cultured at 37° C. in a 5% $CO_2$, 95% air humidity atmosphere.

To establish Epstein-Barr virus (EBV) transformants, $10^6$ T cell depleted peripheral blood mononuclear cells/ml in RPMI 1640 medium supplemented with 20% fetal calf serum (FCS), and 50 μg/ml gentamicin were incubated for 16 hours with EBV-containing supernatant of B95-8 cells (Thorley-Lawson, D. A. et al., *J. Exper. Med.* 146:495 (1977)). Cells in 0.2 ml aliquot were placed in 10 microtiter wells. Medium was replaced with RPMI 1640 medium (supplemented with 20% fetal calf serum and 50 μg/ml gentamicin) until cell growth was noted. Cells grew in most wells and were expanded in the same medium. Phytohemagglutinin (PHA) blasts were established at $10^6$ cells/ml in RPMI 1640 medium (supplemented with 20% fetal calf serum) containing a 1:800 dilution of PHA-P (Difco Laboratories, Inc., Detroit, Mich.). PHA lines were expanded with interleukin 2 (IL-2)-conditioned medium and pulsed weekly with PHA (Cantrell, D. A. et al., *J. Exper. Med.* 158:1895 (1983)). The above procedure was disclosed by Springer, T. et al., *J. Exper. Med.* 160:1901–1918 (1984), which reference is herein incorporated by reference. Cells obtained through the above procedure are then screened with anti-LFA-1 antibodies to determine whether they express the LFA-1 antigen. Such antibodies are disclosed by Sanchez-Madrid, F. et al., *J. Exper. Med.* 158:1785 (1983).

EXAMPLE 2

Assays of Cellular Aggregation and Adhesion

In order to assess the extent of cellular adhesion, aggregation assays were employed. Cell lines used in such assays were washed two times with RPMI 1640 medium containing 5 MM Hepes buffer (Sigma Chemical Co., St. Louis) and resuspended to a concentration of $2 \times 10^6$ cells/ml. Added to flat-bottomed, 96-well microtiter plates (No. 3596; Costar, Cambridge, Mass.) were 50 μl of appropriate monoclonal antibody supernatant or 50 μl of complete medium with or without purified monoclonal antibodies, 50 μl of complete medium containing 200 ng/ml of the phorbol ester phorbol myristate acetate (PMA) and 100 μl of cells at a concentration of $2 \times 10^6$ cells/ml in complete medium. This yielded a final concentration of 50 ng/ml PMA and $2 \times 10^5$ cells/well. Cells were allowed to settle spontaneously, and the degree of aggregation was scored at various time points. Scores ranged from 0 to 5+, where 0 indicated that essentially no cells were in clusters; 1+ indicated that less than 10% of the cells were in aggregates; 2+ indicated that less than 50% of the cells were aggregated; 3+ indicated that up to 100% of the cells were in small, loose clusters; 4+ indicated that up to 100% of the cells were aggregated in larger clusters; and 5+ indicated that 100% of the cells were in large, very compact aggregates. In order to obtain a more quantitative estimate of cellular adhesion, reagents and cells were added to 5 ml polystyrene tubes in the same order as above. Tubes were placed in a rack on a gyratory shaker at 37° C. After 1 hour at approximately 200 rpm, 10 μl of the cell suspension was placed in a hemocytometer and the number of free cells was quantitated. Percent aggregation was determined by the following equation:

$$\% \text{ aggregation} = 100 \times \left(1 - \frac{\text{number of free cells}}{\text{number of input cells}}\right)$$

The number of input cells in the above formula is the number of cells per ml in a control tube containing only cells and complete medium that had not been incubated. The number of free cells in the above equation equals the number of non-aggregated cells per ml from experimental tubes. The above procedures were described by Rothlein, R., et al., *J. Exper. Med.* 163:1132–1149 (1986).

EXAMPLE 3

LFA-1 Dependent Cellular Aggregation

The qualitative aggregation assay described in Example 2 was performed using the Epstein-Barr transformed cell line JY. Upon addition of PMA to the culture medium in the microtiter plates, aggregation of cells was observed. Time lapse video recordings showed that the JY cells on the bottom of the microtiter wells were motile and exhibited active membrane ruffling and pseudopodia movement. Contact between the pseudopodia of neighboring cells often resulted in cell-cell adherence. If adherence was sustained, the region of cell contact moved to the uropod. Contact could be maintained despite vigorous cell movements and the tugging of the cells in opposite directions. The primary difference between PMA-treated and untreated cells appeared to be in the stability of these contacts once they were formed. With PMA, clusters of cells developed, growing in size as additional cells adhered at their periphery.

Figure 3:
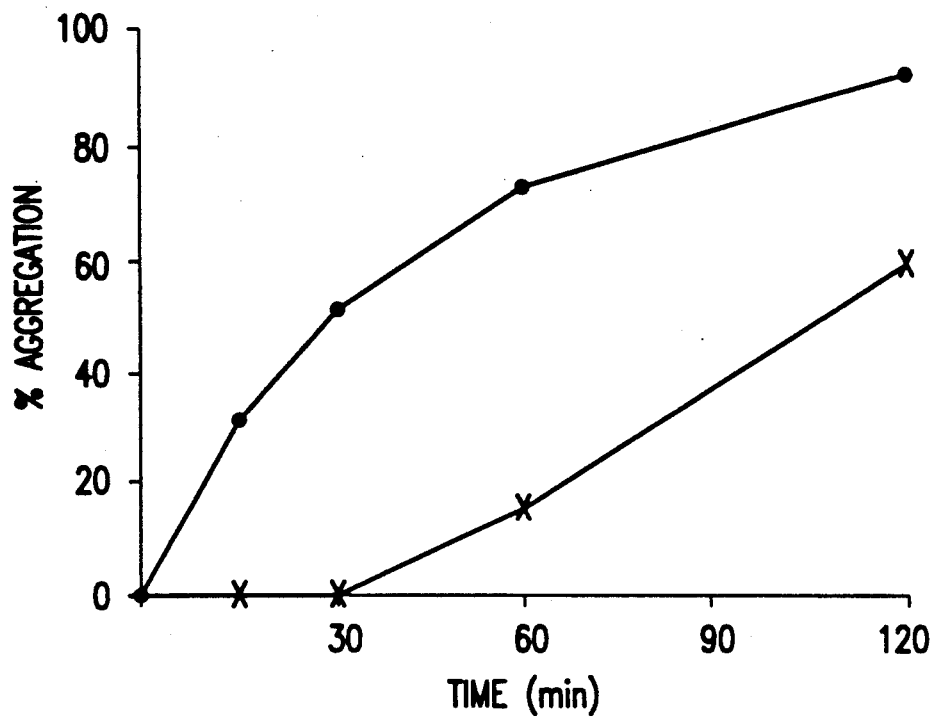
FIG. 3 shows the kinetics of cellular aggregation in the absence (X) or presence of 50 ng/ml of PMA (0).

As a second means of measuring adhesion, the quantitative assay described in Example 2 was used. Cell suspensions were shaken at 200 rpm for 2 hours, transferred to a hemocytometer, and cells not in aggregates were enumerated. In the absence of PMA, 42% (SD=20%, N=6) of JY cells were in aggregates after 2 hours, while JY cells incubated under identical conditions with 50 ng/ml of PMA had 87% (SD=8%, N=6) of the cells in aggregates. Kinetic studies of aggregation showed that PMA enhanced the rate and magnitude of aggregation at all time points tested (FIG. 3).

EXAMPLE 4

Inhibition of Aggregation of Cells Using Anti-LFA-1 Monoclonal Antibodies

To examine the effects of anti-LFA-1 monoclonal antibodies on PMA-induced cellular aggregation, such antibodies were added to cells incubated in accordance with the qualitative aggregation assay of Example 2. The monoclonal antibodies were found to inhibit the formation of aggregates of cells either in the presence or absence of PMA. Both the F(ab')₂ and Fab' fragments of monoclonal antibodies against the alpha chain of LFA-1 were capable of inhibiting cellular aggregation. Whereas essentially 100% of cells formed aggregates in the absence of anti-LFA-1 antibody, less than 20% of the cells were found to be in aggregates when antibody was added. The results of this experiment were described by Rothlein, R. et al. (*J. Exper. Med.* 163:1132-1149 (1986)).

EXAMPLE 5

Cellular Aggregation Requires the LFA-1 Receptor

EBV-transformed lymphoblastoid cells were prepared from patients in the manner described in Example 1. Such cells were screened against monoclonal antibodies capable of recognizing LFA-1 and the cells were found to be LFA-1 deficient.

The qualitative aggregation assay described in Example 2 was employed, using the LFA-1 deficient cells described above. Such cells failed to spontaneously aggregate, even in the presence of PMA.

EXAMPLE 6

The Discovery of ICAM-1

Figure 4:
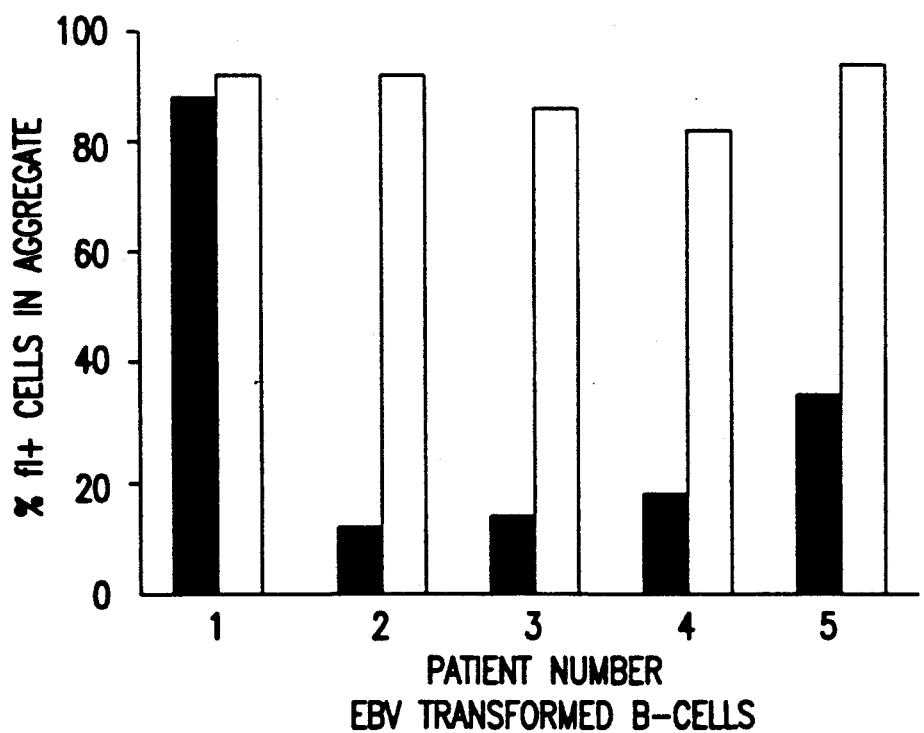
FIG. 4 shows coaggregation between LFA-1$^-$ and LFA-1$^+$ cells. Carboxyfluorescein diacetate labeled EBV-transformed cells ($10^4$) as designated in the figure were mixed with $10^5$ unlabeled autologous cells (solid bars) or JY cells (open bars) in the presence of PMA. After 1.5 h the labeled cells, in aggregates or free, were enumerated using the qualitative assay of Example 2. The percentage of labeled cells in aggregates is shown. One representative experiment of two is shown.

The LFA-1 deficient cells of Example 5 were labeled with carboxyfluorescein diacetate (Patarroyo, M. et al., *Cell. Immunol.* 63:237-248 (1981)). The labeled cells were mixed in a ratio of 1:10 with autologous or JY cells and the percentage of fluorescein-labeled cells in aggregates was determined according to the procedure of Rothlein, R. et al., *J. Exper. Med.* 163:1132-1149 (1986). The LFA-1 deficient cells were found to be capable of coaggregating with LFA-1 expressing cells (FIG. 4).

To determine whether LFA-1 was important only in forming aggregates, or in their maintenance, antibodies capable of binding to LFA-1 were added to the preformed aggregates described above. The addition of antibody was found to strongly disrupt the preformed aggregation. Time lapse video recording confirmed that addition of the monoclonal antibodies to preformed aggregates began to cause disruption within 2 hours (Table 2). After addition of monoclonal antibodies against LFA-1, pseudopodial movements and changes in shape of individual cells within aggregates continued unchanged. Individual cells gradually disassociated from the periphery of the aggregate; by 8 hours cells were mostly dispersed. By video time lapse, the disruption of preformed aggregates by LFA-1 monoclonal antibodies appeared equivalent to the aggregation process in the absence of LFA-1 monoclonal antibody running backwards in time.

TABLE 2

Ability of Anti-LFA-1 Monoclonal Antibodies to Disrupt Preformed PMA-Induced JY Cell Aggregates

| Exp. | 2 h[a] | Aggregation score 18 h −mAb | 18 h +mAb |
|---|---|---|---|
| 1 | 4+ | 4+ | 1+[b] |
| 2 | 3+ | 4+ | 1+[c] |

TABLE 2-continued

Ability of Anti-LFA-1 Monoclonal Antibodies to Disrupt Preformed PMA-Induced JY Cell Aggregates

| Exp. | 2 h[a] | Aggregation score 18 h −mAb | 18 h +mAb |
|---|---|---|---|
| 3 | 5+ | 5+ | 1+[d] |

Aggregation in the qualitative microtiter plate assay was scored visually. With anti-LFA-1 present throughout the assay period, aggregation was less than 1+.
[a]Amount of aggregation just before addition of Mono-clonal antibody at 2 h.
[b]TS1/18 + TS1/22.
[c]TS1/18.
[d]TS1/22.

EXAMPLE 7

The Requirement of Divalent Ions for LFA-1 Dependent Aggregation

LFA-1 dependent adhesions between cytotoxic T cells and targets require the presence of magnesium (Martz, E. *J. Cell Biol.* 84:584-598 (1980)). PMA-induced JY cell aggregation was tested for divalent cation dependence. JY cells failed to aggregate (using the assay of Example 2) in medium free of calcium or magnesium ions. The addition of divalent magnesium supported aggregation at concentrations as low as 0.3 mM. Addition of calcium ions alone had little effect. Calcium ions, however, were found to augment the ability of magnesium ions to support PMA-induced aggregation. When 1.25 mM calcium ions were added to the medium, magnesium ion concentrations as low as 0.02 millimolar were found to support aggregation. These data show that the LFA-1 dependent aggregation of cells requires magnesium ions, and that calcium ions, though insufficient of themselves, can synergize with magnesium ions to permit aggregation.

EXAMPLE 8

The Isolation of Hybridoma Cells Capable of Expressing Anti-ICAM-1 Monoclonal Antibodies Monoclonal antibodies capable of binding to ICAM-1 were isolated according to the method of Rothlein, R. et al., J. Immunol. 137:1270-1274 (1986), which reference has been incorporated by reference herein. Thus, 3 BALB/C mice were immunized intraperitoneally with EBV-transformed peripheral blood mononuclear cells from an LFA-1-deficient individual (Springer, T. A. et al., *J. Exper. Med.* 160:1901 (1984)). Approximately 10⁷ cells in 1 ml RPMI 1640 medium was used for each immunization. The immunizations were administered 45, 29, and 4 days before spleen cells were removed from the mice in order to produce the desired hybridoma cell lines. On day 3 before the removal of the spleen cells, the mice were given an additional 10⁷ cells in 0.15 ml medium (intravenously).

Isolated spleen cells from the above-described animals were fused with P3X73Ag8.653 myeloma cells at a ratio of 4:1 according to the protocol of Galfre, G. et al., *Nature* 266:550 (1977). Aliquots of the resulting hybridoma cells were introduced into 96-well microtiter plates. The hybridoma supernatants were screened for inhibition of aggregation, and one inhibitory hybridoma (of over 600 wells tested) was cloned and subcloned by limiting dilution. This subclone was designated RR1/1.1.1 (hereinafter designated "RR1/1").

Monoclonal antibody RR1/1 was consistently found to inhibit PMA-stimulated aggregation of the LFA-1 expressing cell line JY. The RR1/1 monoclonal antibody inhibited aggregation equivalently, or slightly less than some monoclonal antibodies to the LFA-1 alpha or beta subunits. In contrast, control monoclonal antibody against HLA, which is abundantly expressed on JY cells, did not inhibit aggregation. The antigen bound by monoclonal antibody RR1/1 is defined as the intercellular adhesion molecule-1 (ICAM-1).

EXAMPLE 9

Figure 5:
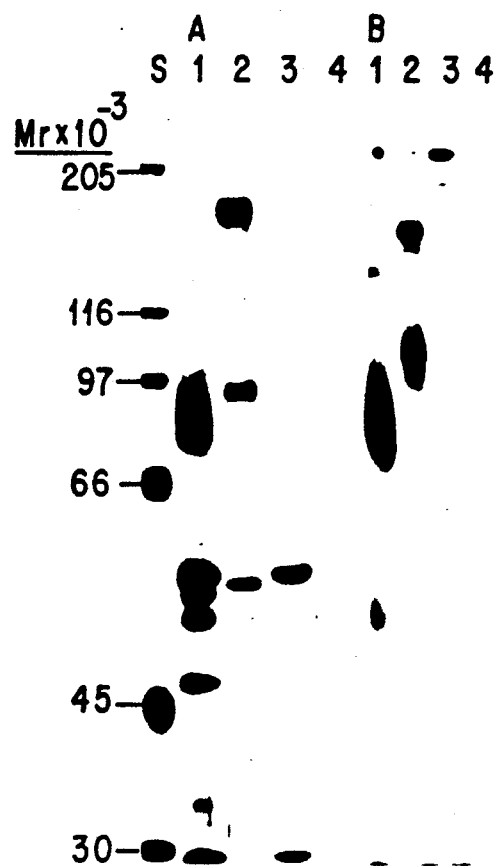
FIG. 5 shows the immunoprecipitation of ICAM-1 and LFA-1 from JY cells. Triton X-100 lysates of JY cells (lanes I and 2) or control lysis buffer (lanes 3 and 4) were immunoprecipitated with antibody capable of binding to ICAM-1 (lanes 1 and 3) or antibodies capable of binding to LFA-1 (lanes 2 and 4). Panel A shows results under reducing conditions; Panel B shows results obtained under non-reducing conditions. Molecular weight standards were run in lane S.

Use of Anti-ICAM-1 Monoclonal Antibodies to Characterize the ICAM-1 Molecule In order to determine the nature of ICAM-1, and particularly to determine whether ICAM-1 was distinct from LFA-1, cell proteins were immunoprecipitated using monoclonal antibody RR1/1. The imunoprecipitation was performed according to the method of Rothlein, R. et al. (*J. Immunol.* 137:1270–1274 (1986)). JY cells were lysed at $5 \times 10^7$ cells/ml in 1% Tri ton X-100, 0.14 m NaCl, 10 mM Tris, pH 8.0, with freshly added 1 mM phenylmethylsulfonylfluoride, 0.2 units per ml trypsin inhibitor aprotinin (lysis buffer) for 20 minutes at 4° C. Lysates were centrifuged at 10,000 $\times$g for 10 minutes and precleared with 50 μl of a 50% suspension of CNBr-activated, glycine-quenched Sepharose C1-4B for 1 hour at 4° C. One milliliter of lysate was immunoprecipitated with 20 μl of a 50% suspension of monoclonal antibody RR1/1 coupled to Sepharose C1-4B (1 mg/ml) overnight at 40° C. (Springer, T. A. et al., *J. Exper. Med.* 160:1901 (1984)). Sepharose-bound monoclonal antibody was prepared using CNBr-activation of Sepharose CL-4B in carbonate buffer according to the method of March, S. et al. (*Anal. Biochem.* 60:149 (1974)). Washed immunoprecipitates were subjected to SDS-PAGE and silver staining according to the procedure of Morrissey, J. H. *Anal. Biochem.* 117:307 (1981). After elution of proteins with SDS sample buffer (Ho, M. K. et al., *J. Biol. Chem.* 258:636 (1983)) at 100° C., the samples were divided in half and subjected to electrophoresis (SDS-8% PAGE) under reducing (FIG. 5A) or nonreducing conditions (FIG. 5B). Bands having molecular weights of 50 kd and 25 kd corresponded to the heavy and light chains of immunoglobulins from the monoclonal antibody Sepharose (FIG. 5A, lane 3). Variable amounts of other bands in the 25–50 kd weight range were also observed, but were not seen in precipitates from hairy leukemia cells, which yielded only a 90 kd molecular weight band. The 177 kd alpha subunit and 95 kd beta subunit of LFA-1 were found to migrate differently from ICAM-1 under both reducing (FIG. 5A, lane 2) and nonreducing (FIG. 5B, lane 2) conditions.

In order to determine the effect of monoclonal antibody RR1/1 on PHA-lymphoblast aggregation, the quantitative aggregation assay described in Example 2 was employed. Thus, T cell blast cells were stimulated for 4 days with PHA, thoroughly washed, then cultured for 6 days in the presence of IL-2 conditioned medium. PHA was found to be internalized during this 6-day culture, and did not contribute to the aggregation assay. In three different assays with different T cell blast preparations, ICAM-1 monoclonal antibodies consistently inhibited aggregation (Table 3).

TABLE 3

Inhibition of PMA-Stimulated PHA-Lymphoblast Aggregation by RR1/1 Monoclonal Antibody[a]

| Expt. | PMA | MAb | % Aggregation | % Inhibition[b] |
|---|---|---|---|---|
| 1[c] | − | Control | 9 | — |
|  | + | Control | 51 | 0 |
|  | + | HLA—A,B | 58 | −14[d] |
|  | + | LFA-1 alpha | 31 | 39 |
|  | + | ICAM-1 | 31 | 39 |
| 2[e] | − | Control | 10 | — |
|  | + | Control | 78 | 0 |
|  | + | LFA-1 beta | 17 | 78 |
|  | + | ICAM-1 | 50 | 36 |
| 3[f] | − | — | 7 |  |
|  | + | Control | 70 |  |
|  | + | HLA—A,B | 80 | −14 |
|  | + | LFA-3 | 83 | −19 |
|  | + | LFA-1 alpha | 2 | 97 |
|  | + | LFA-1 beta | 3 | 96 |
|  | + | ICAM-1 | 34 | 51 |

[a] Aggregation of PHA-induced lymphoblasts stimulated with 50 ng/ml PMA was quantitated indirectly by microscopically counting the number of nonaggregated cells as descirbed in Example 2.
[b] Percent inhibition relative to cells treated with PMA and X63 monoclonal antibody.
[c] Aggregation was measured 1 hr after the simultaneous addition of monoclonal antibody and PMA. Cells were shaken at 175 rpm.
[d] A negative number indicates percent enhancement of aggregation.
[e] Aggregation was measured 1 hr after the simultaneous addition of monoclonal antibody and PMA. Cells were pelleted at 220 × G for 1 min. incubated at 37° C. and for 15 min. gently resuspended, and shaken for 45 min. at 100 rpm.
[f] Cells were pretreated with PMA for 4 hr at 37° C. After monoclonal antibody was added, the tubes were incubated at 37° C. stationary for 20 min. and shaken at 75 rpm for 100 min.

LFA-1 monoclonal antibodies were consistently more inhibitory than ICAm-1 monoclonal antibodies, whereas HLA-A, B and LFA-3 monoclonal antibodies were without effect. These results indicate that of the monoclonal antibodies tested, only those capable of binding to LFA-1 or ICAM-1 were capable of inhibiting cellular adhesion.

EXAMPLE 10

Preparation of Monoclonal Antibody to ICAM-1

Immunization

A Balb/C mouse was immunized intraperitoneally (i.p.) with 0.5 mls of $2 \times 10^7$ JY cells in RPMI medium 103 days and 24 days prior to fusion. On day 4 and 3 prior to fusion, mice were immunized i.p. with $10^7$ cells of PMA differentiated U937 cells in 0.5 ml of RPMI medium.

Differentiation of U937 Cells

U937 cells (ATCC CRL-1593) were differentiated by incubating them at $5 \times 10^5$/ml in RPMI with 10% Fetal Bovine Serum, 1% glutamine and 50 μg/ml gentamyin (complete medium) containing 2 ng/ml phorbol-12-myristate acetate (PMA) in a sterile polypropylene container. On the third day of this incubation, one-half of the volume of medium was withdrawn and replaced with fresh complete medium containing PMA. On day 4, cells were removed, washed and prepared for immunization.

Fusion

Spleen cells from the immunized mice were fused with P3x63 Ag8-653 myeloma cells at a 4:1 ratio according to Galfre et al., (*Nature* 266:550 (1977)). After the fusion, cells were plated in a 96 well flat bottomed microtiter plates at $10^5$ spleen cells/well.

Selection for Anti-ICAM-1 Positive Cells

After one week, 50 μl of supernatant were screened in the qualitative aggregation assay of Example 2 using both JY and SKW-3 as aggregating cell lines. Cells from supernatants inhibiting JY cell aggregation but not SKW-3 were selected and cloned 2 times utilizing limiting dilution.

This experiment resulted in the identification and cloning of three separate hybridoma lines which produced anti-ICAM-1 monoclonal antibodies. The antibodies produced by these hybridoma lines were $IgG_{2a}$, $IgG_{2b}$, and IgM, respectively. The hybridoma cell line which produced the $IgG_{2a}$ anti-ICAM-1 antibody was given the designation R6'5'D6'E9'B2. The antibody produced by the preferred hybridoma cell line was designated R6'5'D6'E9'B2 (herein referred to as "R6-5-D6"). Hybridoma cell line R6'5'D6'E9'B2 was deposited with the American Type Culture Collection on Oct. 30, 1987 and given the designation ATCC HB 9580.

EXAMPLE 11

The Expression and Regulation of ICAM-1

In order to measure ICAM-1 expression, a radioimmune assay was developed. In this assay, purified RR1/1 was iodinated using iodogen to a specific activity of 10 μCi/μg. Endothelial cells were grown in 96 well plates and treated as described for each experiment. The plates were cooled at 4° C. by placing in a cold room for 0.5-1 hr, not immediately on ice. The monolayers were washed 3× with cold complete media and then incubated 30 m at 4° C. with $^{125}$I RR1/1. The monolayers were then washed 3× with complete media. The bound $^{125}$I was released using 0.1 N NAOH and counted. The specific activity of the $^{125}$I RR1/1 was adjusted using unlabeled RR1/1 to obtain a linear signal over the range of antigen densities encountered in this study. Non-specific binding was determined in the presence of a thousand fold excess of unlabeled RR1/1 and was subtracted from total binding to yield the specific binding.

ICAM-1 expression, measured using the above described radioimmune assay, is increased on human umbilical vein endothelial cells (HUVEC) and human saphenous vein endothelial cells (HSVEC) by IL-1, TNF, LPS and IFN gamma (Table 4). Saphenous vein endothelial cells were used in this study to confirm the results from umbilical vein endothelial cells in cultured large vein endothelial cells derived from adult tissue. The basal expression of ICAM-1 is 2 fold higher on saphenous vein endothelial cells than on umbilical vein endothelial cells. Exposure of umbilical vein endothelial cell to recombinant IL-1 alpha, IL-1 beta, and TNF gamma increase ICAM-1 expression 10-20 fold. IL-1 alpha, TNF and LPS were the most potent inducers and IL-1 was less potent on a weight basis and also at saturating concentrations for the response (Table 4). IL-1 beta at 100 ng/ml increased ICAM-1 expression by 9 fold on HUVEC and 7.3 fld on HSVEC with half-maximal increase occuring at 15 ng/ml. RTNF at 50 ng/ml increased ICAM-1 expression 16 fold on HUVEC and 11 fold on HSVEC with half maximal effects at 0.5 ng/ml. Interferon-gamma produced a significant increase in ICAM-1 expression of 5.2 fold on HUVEC or 3.5 fold on HSVEC at 10,000 U/ml. The effect of LPS at 10 μg/ml was similar in magnitude to that of RTNF. Pairwise combinations of these mediators resulted in additive or slightly less than additive effects on ICAM-1 expression (Table 4). Cross-titration of RTNF with rIL-1 beta or RIFN gamma showed no synergism between these at suboptimal or optimal concentrations.

Since LPS increased ICAM-1 expression on endothelial cells at levels sometimes found in culture media, the possibility that the basal ICAM-1 expression might be due to LPS was examined. When several serum batchs were tested it was found that low endotoxin serum gave lower ICAM-1 basal expression by 25%. All the results reported here were for endothelial cells grown in low endotoxin serum. However, inclusion of the LPS neutralizing antibiotic polymyxin B at 10 μg/ml decreased ICAM-1 expression only an additional 25% (Table 4). The increase in ICAM-1 expression on treatment with IL-1 or TNF was not effected by the presence of 10 μg/ml polymyxin B which is consistent with the low endotoxin levels in these preparations (Table 4).

TABLE 4

Anti-ICAM-1 Monoclonal Antibodies

| Condition (16 hr) | $^{125}$I Specifically bound (CPM) HUVEC | | HSVEC | |
|---|---|---|---|---|
| control | 603 ± 11 | — | 1132 ± 31 | — |
| 100 ng/ml rIL-1 beta | 5680 ± 633 | 9x | 8320 ± 766 | 7.3x |
| 50 ng/ml rIL-1 alpha | 9910 ± 538 | 16x | — | — |
| 50 ng/ml rTNF alpha | 9650 ± 1500 | 16x | 12690 ± 657 | 11.2x |
| 10 μg/ml LPS | 9530 ± 512 | 16x | 10459 ± 388 | 9.2x |
| 10 ng/ml rIFN gamma | 3120 ± 308 | 5.2x | 4002 ± 664 | 3.5x |
| rIL-1 beta + rTNF | 1469 ± 1410 | 24x | 16269 ± 660 | 14x |
| rIL-1 beta + LPS | 13986 ± 761 | 23x | 10870 ± 805 | 10x |
| rIL-1 beta + rIFN gamma | 7849 ± 601 | 13x | 8401 ± 390 | 7.4x |
| rTNF + LPS | 15364 ± 1241 | 24x | 16141 ± 1272 | 14x |
| rTNF + rIFN gamma | 13480 ± 1189 | 22x | 13238 ± 761 | 12x |
| LPS + IFN gamma | 10206 ± 320 | 17x | 10987 ± 668 | 10x |
| polymyxin B (10 μg/ml) | 480 ± 23 | — | — | — |
| polymyxin B + rIL-1 | 5390 ± 97 | 11x | — | — |
| polymyxin B + rTNF | 9785 ± 389 | 20x | — | — |
| 1 μg/ml LPS | 7598 ± 432 | 13x | — | — |
| polymyxin B + LPS | 510 ± 44 | 1.1x | — | — |

Upregulation of ICAM-1 expression on HVEC and HSVEC- HUVEC or HSVEC were seeded into 96 well plates at 1:3 from a confluent monolayer and allowed to grow to confluence. Cells were then treated with the indicated materials or media for 16 hr and the RIA done as in methods. All points were done in quadruplicate.

EXAMPLE 12

Kinetics of Interleukin 1 and Gamma Interferon Induction of ICAM-1

The kinetics of interleukin I and gamma interferon effects on ICAM-1 expression on dermal fibroblasts were determined using the $^{125}$I goat anti-mouse IgG binding assay of Dustin, M. L. et al. (*J. Immunol.* 137:245-254 (1986); which reference is herein incorporated by reference). To perform this binding assay, human dermal fibroblasts were grown in a 96-well microtiter plate to a density of $2-8 \times 10^4$ cells/well (0.32 cm²). The cells were washed twice with RPMI 1640 medium supplemented as described in Example 1. The cells were additionally washed once with Hanks Balanced Salt Solution (HBSS), 10 mM HEPES, 0.05% $NaN_3$ and 10% heat-inactivated fetal bovine serum. Washing with this binding buffer was done at 4° C. To each well was added 50 μl of the above-described binding buffer and 50 μl of the appropriate hybridoma supernatant with X63 and W6/32 as the negative and positive controls, respectively. After incubation for 30 minutes at 4° C., with gentle agitation, the wells were washed twice with binding buffer, and the second antibody $^{125}$I-goat anti-mouse IgG, was added at 50 nCi in 100 μl. The $^{125}$I-goat anti-mouse antibody was prepared by using Iodogen (Pierce) according to the method of Fraker, P. J. et al. (*Biochem. Bioshys. Res. Commun.* 80:849 (1978)). After 30 minutes at 4° C., the wells were washed twice with 200 μl of binding buffer and the cell layer was solubilized by adding 100 μl of 0.1 N NAOH. This and a 100 μl wash were counted in a Beckman 5500 gamma counter. The specific counts per minute bound was calculated as [cpm with monoclonal antibody]-[cpm with X63]. All steps, including induction with specific reagents, were carried out in quadruplicate.

Figure 6:
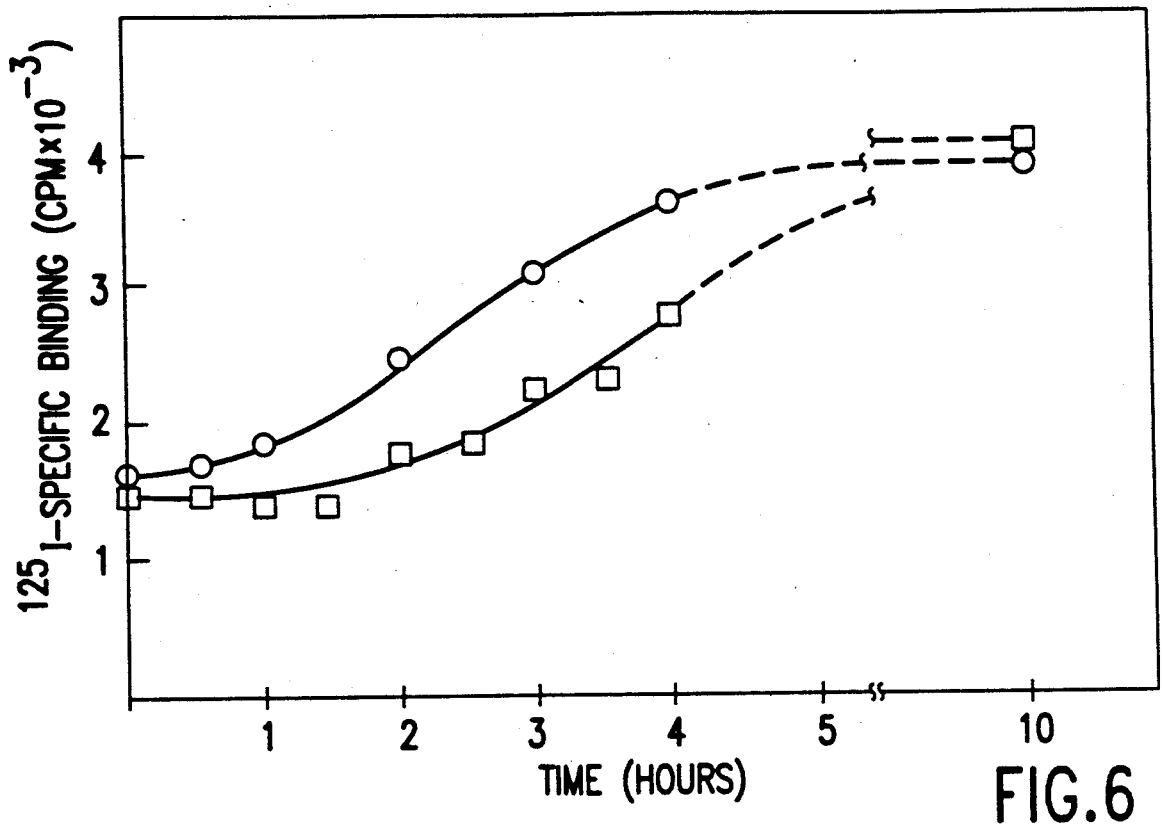
FIG. 6 shows the kinetics of IL-1 and gamma interferon effects on ICAM-1 expression on human dermal fibroblasts. Human dermal fibroblasts were grown to a density of $8 \times 10^4$ cells/0.32 cm$^2$ well . IL-1 (10 U/ml, closed circles) or recombinant gamma interferon (10 U/ml, open squares) was added, and at the indicated time, the assay was cooled to 4° C. and an indirect binding assay was performed. The standard deviation did not exceed 10%.

The effect of interleukin I with a half-life for ICAM-1 induction of 2 hours was more rapid than that of gamma interferon with a half-life of 3.75 hours (FIG. 6). The time course of return to resting levels of ICAM-1 appeared to depend upon the cell cycle or rate of cell growth. In quiescent cells, interleukin 1 and gamma interferon effects are stable for 2-3 days, whereas in log phase cultures, ICAM-1 expression is near baseline 2 days after the removal of these inducing agents.

Figure 7:
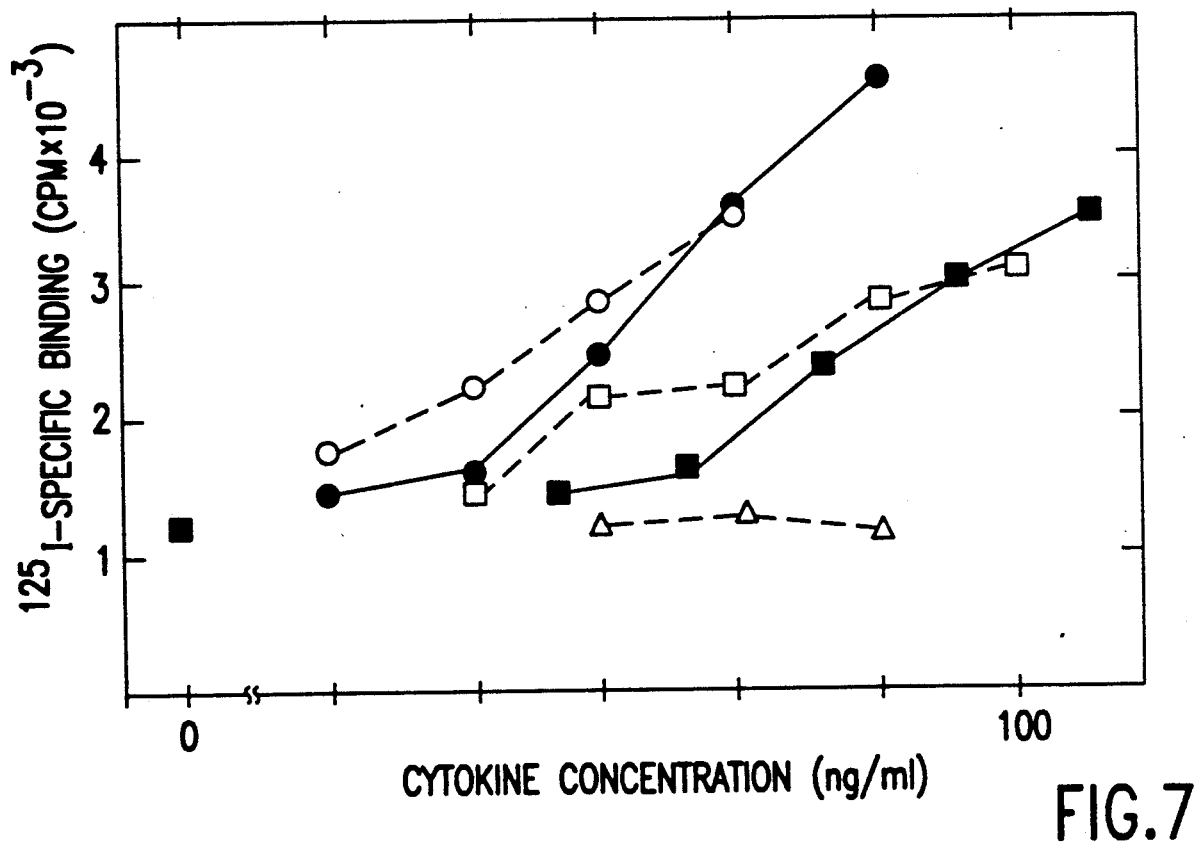
FIG. 7 shows the concentration dependence of IL-1 and gamma interferon effects on ICAM-1. Human dermal fibroblasts were grown to a density of $8 \times 10^4$ cells/0. 32 cm$^2$well. IL-2 (open circle), recombinant human IL-1 (open square), recombinant mouse IL-1 (solid square), recombinant human gamma interferon (solid circles), and recombinant beta interferon (open triangle) were added at the indicated dilution and were incubated for 4 hours (IL-1) or 16 hours (beta and gamma interferon). The indicated results are the means from quadruplicate determinations; standard deviation did not exceed 10%.

The dose response curves for induction of ICAM-1 by recombinant mouse and human interleukin 1, and for recombinant human gamma interferon, are shown in FIG. 7. Gamma interferon and interleukin 1 were found to have similar concentration dependencies with nearly identical effects at 1 ng/ml. The human and mouse recombinant interleukin 1 also have similar curves, but are much less effective than human interleukin 1 preparations in inducing ICAM-1 expression.

Cyclohexamide, an inhibitor of protein synthesis, and actinomycin D, an inhibitor of MRNA synthesis, abolish the effects of both interleukin 1 and gamma interferon on ICAM-1 expression on fibroblasts (Table 5). Furthermore, tunicamycin, an inhibitor of N-linked glycosylation, only inhibited the interleukin 1 effect by 43%. These results indicate that protein and MRNA synthesis, but not N-linked glycosylation, are required for interleukin 1 and gamma interferon-stimulated increases in ICAM-1 expression.

TABLE 5

Effects of Cycloheximide, Actinomycin D, and Tunicamycin on ICAM-1 Induction by IL 1 and gamma IFN on Human Dermal Fibroblasts[a]

| Treatment | $^{125}$I Goat Anti-Mouse IgG Specifically Bound (cpm) | |
|---|---|---|
| | anti-ICAM-1 | anti-HLA-A,B,C |
| Control (4 hr) | 1524 ± 140 | 11928 ± 600 |
| +cycloheximide | 1513 ± 210 | 10678 ± 471 |
| +actinomycin D | 1590 ± 46 | 12276 ± 608 |
| +tunicamycin | 1461 ± 176 | 12340 ± 940 |
| IL 1 (10 U/ml) (4 hr) | 4264 ± 249 | 12155 ± 510 |
| +cycloheximide | 1616 ± 381 | 12676 ± 446 |
| +actinomycin D | 1613 ± 88 | 12294 ± 123 |
| +tunicamycin | 3084 ± 113 | 13434 ± 661 |
| IFN-γ (10 U/ml) (18 hr) | 4659 ± 109 | 23675 ± 800 |
| +cyclohexamide | 1461 ± 59 | 10675 ± 800 |
| +actinomycin D | 1326 ± 186 | 12089 ± 550 |

[a]Human fibroblasts were grown to a density of 8 × 10$^4$ cells/0.32 cm$^2$ well. Treatments were carried out in a final volume of 50 μl containing the indicated reagents. Cycloheximide, actinomycin D, and tunicamycin were added at 20 μg/ml, 10 μM, and 2 μg/ml, respectively, at the same time as the cytokines. All points are means of quadruplicate wells ± SD.

EXAMPLE 13

The Tissue Distribution of ICAM-1

Histochemcial studies were performed on frozen tissue of human organs to determine the distribution of ICAM-1 in thymus, lymph nodes, intestine, skin, kidney, and liver. To perform such an analysis, frozen tissue sections (4 μm thick) of normal human tissue were fixed in acetone for 10 minutes and stained with the monoclonal antibody, RR1/1 by an immunoperoxidase technique which employed the avidin-biotin complex method (Vector Laboratories, Burlingame, Calif.) described by Cerf-Bensussan, N. et al. (*J. Immunol.* 130:2615 (1983)). After incubation with the antibody, the sections were sequentially incubated with biotinylated horse anti-mouse IgG and avidin-biotinylated peroxidase complexes. The sections were finally dipped in a solution containing 3-amino-9-ethylcarbazole (Aldrich Chemical Co., Inc., Milwaukee, Wis.) to develop a color reaction. The sections were then fixed in 4% formaldehyde for 5 minutes and were counterstained with hematoxylin. Controls included sections incubated with unrelated monoclonal antibodies instead of the RR1/1 antibody.

ICAM-1 was found to have a distribution most similar to that of the major histocompatibility complex (MHC) Class II antigens. Most of the blood vessels (both small and large) in all tissues showed staining of endothelial cells with ICAM-1 antibody. The vascular endothelial staining was more intense in the interfollicular (paracortical) areas in lymph nodes, tonsils, and Peyer's patches as compared with vessels in kidney, liver, and normal skin. In the liver, the staining was mostly restricted to sinusoidal lining cells; the hepatocytes and the endothelial cells lining most of the portal veins and arteries were not stained.

In the thymic medulla, diffuse staining of large cells and a dendritic staining pattern was observed. In the cortex, the staining pattern was focal and predominantly dendritic. Thymocytes were not stained. In the peripheral lymphoid tissue, the germinal center cells of the secondary lymphoid follicles were intensely stained. In some lymphoid follicles, the staining pattern was mostly dendritic, with no recognizable staining of lymphocytes. Faint staining of cells in the mantle zone was also observed. In addition, dendritic cells with cytoplasmic extensions (interdigitating reticulum cells) and a small number of lymphocytes in the interfollicular or paracortical areas stained with the ICAM-1 binding antibody.

Cells resembling macrophages were stained in the lymph nodes and lamina propria of the small intestine. Fibroblast-like cells (spindle-shaped cells) and dendritic cells scattered in the stroma of most of the organs studied stained with the ICAM-1 binding antibody. No staining was discerned in the Langerhans/indeterminant cells in the epidermis. No staining was observed in smooth muscle tissue.

The staining of epithelial cells was consistently seen in the mucosa of the tonsils. Although hepatocytes, bile duct epithelium, intestinal epithelial cells, and tubular epithelial cells in kidney did not stain in most circumstances, sections of normal kidney tissue obtained from a nephrectomy specimen with renal cell carcinoma showed staining of many proximal tubular cells for ICAM-1. These tubular epithelial cells also stained with an anti-HLA-DR binding antibody.

In summary, ICAM-1 is expressed on non-hematopoietic cells such as vascular endothelial cells and on hematopoietic cells such as tissue macrophages and mitogen-stimulated T lymphocyte blasts. ICAM-1 was found to be expressed in low amounts on peripheral blood lymphocytes.

EXAMPLE 14

The Purification of ICAM-1 by Monoclonal Antibody Affinity Chromatography

General purification scheme

ICAM-1 was purified from human cells or tissue using monoclonal antibody affinity chromatography. Monoclonal antibody, RR1/1, reactive with ICAM-1 was first purified, and coupled to an inert column matrix. This antibody is described by Rothlein, R. et al. *J. Immunol.* 137:1270–1274 (1986), and Dustin, M. L. et al. (*J. Immunol. IL*7:245 (1986). ICAM-1 was solubilized from cell membranes by lysing the cells in a non-ionic detergent, Triton X-100, at a near neutral pH. The cell lysate containing solubilized ICAM-1 was then passed through precolumns designed to remove materials that bind nonspecifically to the column matrix material, and then through the monoclonal antibody column matrix, allowing the ICAM-1 to bind to the antibody. The antibody column was then washed with a series of detergent wash buffers of increasing pH up to pH 11.0. During these washes ICAM-1 remained bound to the antibody matrix, while non-binding and weakly binding contaminants were removed. The bound ICAM-1 was then specifically eluted from the column by applying a detergent buffer of pH 12.5.

Purification of monoclonal antibody RR1/1 and covalent coupling to Sepharose CL-4B.

The anti-ICAM-1 monoclonal antibody RR1/1 was purified from the ascites fluid of hybridoma-bearing mice, or from hybridoma culture supernates by standard techniques of ammonium sulfate precipitation and protein A affinity chromatography (Ey et al., *Immunochem.* 15:429 (1978)). The purified IgG, or rat IgG (Sigma Chemical Co., St. Louis, Mo.) was covalently coupled to Sepharose CL-4B (Pharmacia, Upsala, Sweden) using a modification of the method of March et al. (*Anal. Biochem.* 60:149 (1974)). Briefly, Sepharose CL-4B was washed in distilled water, activated with 40 mg/ml CNBr in 5 M $K_2HPO_4$ (pH approximately 12) for 5 minutes, and then washed extensively with 0.1 mM HCl at 4° C. The filtered, activated Sepharose was resuspended with an equal volume of purified antibody (2-10 mg/ml in 0.1 M $NaHCO_3$, 0.1 M NaCl). The suspension was incubated for 18 hours at 4° C. with gentle end-over-end rotation. The supernatant was then monitored for unbound antibody by absorbance at 280 nm, and remaining reactive sites on the activated Sepharose were saturated by adding glycine to 0.05 M. Coupling efficiency was usually greater than 90%.

Detergent solubilization of membranes prepared from human spleen.

All procedures were done at 4° C. Frozen human spleen (200 g fragments) from patients with hairy cell leukemia were thawed on ice in 200 ml Tris-saline (50 mM Tris, 0.14 M NaCl, pH 7.4 at 4° C.) containing 1 mM phenylmethylsulfonylfluoride (PMSF), 0.2 U/ml aprotinin, and 5 mM iodoacetamide. The tissue was cut into small pieces, and homogenized at 4° C. with a Tekmar power homogenizer. The volume was then brought to 300 ml with Tris-saline, and 100 ml of 10% Tween 40 (polyoxyethylene sorbitan monopalmitate) in Tris-saline was added to achieve a final concentration of 2.5% Tween 40.

To prepare membranes, the homogenate was extracted using three strokes of a Dounce or, more preferably, a Teflon Potter Elvejhem homogenizer, and then centrifuged at 1000 ×g for 15 minutes. The supernatant was retained and the pellet was re-extracted with 200 ml of 2.5% Tween 40 in Tris-saline. After centrifugation at 1000 ×g for 15 minutes, the supernatants from both extractions were combined and centrifuged at 150,000 ×g for 1 hour to pellet the membranes. The membranes were washed by resuspending in 200 ml Tris-saline, centrifuged at 150,000 ×g for 1 hour. The membrane pellet was resuspended in 200 ml Tris-saline and was homogenized with a motorized homogenizer and Teflon pestle until the suspension was uniformly turbid. The volume was then brought up to 900 ml with Tris-saline, and N-lauroyl sarcosine was added to a final concentration of 1%. After stirring at 4° C. for 30 minutes, insoluble material in the detergent lysate was removed by centrifugation at 150,000 ×g for 1 hour. Triton X-100 was then added to the supernatant to a final concentration of 2%, and the lysate was stirred at 4° C. for 1 hour.

Detergent solubilization of JY B-lymphoblastoid cells

The EBV-transformed B-lymphoblastoid cell line JY was grown in RPMI-1640 containing 10% fetal calf serum (FCS) and 10 mM HEPES to an approximate density of $0.8-1.0 \times 10^6$ cells/ml. To increase the cell surface expression of ICAM-1, phorbol 12-myristate 13-acetate (PMA) was added at 25 ng/ml for 8-12 hours before harvesting the cells. Sodium vanadate (50 $\mu$M) was also added to the cultures during this time. The cells were pelleted by centrifugation at 500 ×g for 10 minutes, and washed twice in Hank's Balanced Salt Solution (HBSS) by resuspension and centrifugation. The cells (approximately 5 g per 5 liters of culture) were lysed in 50 ml of lysis buffer (0.14 M NaCl, 50 mM Tris pH 8.0, 1% Triton X-100, 0.2 U/ml aprotinin, 1 mM PMSF, 50 $\mu$M sodium vanadate) by stirring at 4° C. for 30 minutes. Unlysed nuclei and insoluble debris were removed by centrifugation at 10,000 ×g for 15 minutes, followed by centrifugation of the supernatant at 150,000 ×g for 1 hour, and filtration of the supernatant through Whatman 3 mm filter paper.

Affinity chromatography of ICAM-1 for structural studies

For large scale purification of ICAM-1 to be used in structural studies, a column of 10 ml of RR1/1-Sepharose CL-4B (coupled at 2.5 mg of antibody/ml of gel), and two 10 ml pre-columns of CNBr-activated, glycine-quenched Sepharose CL-4B, and rat-IgG coupled to Sepharose CL-4B (2mg/ml) were used. The columns were connected in series, and pre-washed with 10 column volumes of lysis buffer, 10 column volumes of pH 12.5 buffer (50 mM triethylamine, 0.1% Triton X-100, pH 12.5 at 4° C.), followed by equilibration with 10 column volumes of lysis buffer. One liter of the detergent lysate of human spleen was loaded at a flow rate of 0.5–1.0 ml per minute. The two pre-columns were used to remove non-specifically binding material from the lysate before passage through the RR1/1-Sepharose column.

After loading, the column of RRI/1-Sepharose and bound ICAM-1 was washed sequentially at a flow rate of 1 ml/minute with a minimum of 5 column volumes each of the following: 1) lysis buffer, 2) 20 mM Tris pH 8.0/0.14 M NaCl/0.1% Triton X-100, 3) 20 Mm glycine pH 10.0/0.1% Triton X-100, and 4) 50 mM triethylamine pH 11.0/0.1% Triton X-100. All wash buffers contained 1 mM PMSF and 0.2 U/ml aprotinin. After washing, the remaining bound ICAM-1 was eluted with 5 column volumes of elution buffer (50 mM triethylamine/0.1% Triton X-100/pH 12.5 at 4° C.) at a flow rate of 1 ml/3 minutes. The eluted ICAM-1 was collected in 1 ml fractions and immediately neutralized by the addition of 0.1 ml of 1 M Tris, pH 6.7. Fractions containing ICAM-1 were identified by SDS-polyacrylamide electrophoresis of 10 μl aliquots (Springer et al., *J. Exp. Med.* 160:1901 (1984)), followed by silver staining (Morrissey, J. H., *Anal. Biochem.* 117:307 (1981)). Under these conditions, the bulk of the ICAM-1 eluted in approximately 1 column volume and was greater than 90% pure as judged from silver-stained electropherograms (a small amount of IgG, leeched from the affinity matrix, was the major contaminant). The fractions containing ICAM-1 were pooled and concentrated approximately 20-fold using Centricon-30 microconcentrators (Amicon, Denvers, Mass.). The purified ICAM-1 was quantitated by Lowry protein assay of an ethanol-precipitated aliquot of the pool: approximately 500 μg of pure ICAM-1 were produced from the 200 g of human spleen.

Approximately 200 μg of purified ICAM-1 was subjected to a second stage purification by preparative SDS-polyacrylamide gel electrophoresis. The band representing ICAM-1 was visualized by soaking the gel in 1 M KCl. The gel region which contained ICAM-1 was then excised and electroeluted according to the method of Hunkapiller et al., *Meth. Enzymol.* 91:227–236 (1983). The purified protein was greater than 98% pure as judged by SDS-PAGE and silver staining.

Affinity purification of ICAM-1 for functional studies

ICAM-1 for use in functional studies was purified from detergent lysates of JY cells as described above, but on a smaller scale (a 1 ml column of RR1/1-Sepharose), and with the following modifications. All solutions contained 50 μM sodium vanadate. After washing the column with pH 11.0 buffer containing 0.1% Triton X-100, the column was washed again with five column volumes of the same buffer containing 1% n-octyl-beta-D-glucopyranoside (octylglucoside) in place of 0.1% Triton X-100. The octylglucoside detergent displaces the Triton X-100 bound to the ICAM-1, and unlike Triton X-100, can be subsequently removed by dialysis. The ICAM-1 was then eluted with pH 12.5 buffer containing 1% octylglucoside in place of 0.1% Triton X-100, and was analyzed and concentrated as described above.

EXAMPLE 15

Characteristics of Purified ICAM-1

ICAM-1 purified from human spleen migrates in SDS-polyacrylamide gels as a broad band of $M_r$ of 72,000 to 91,000. ICAM-1 purified from JY cells also migrates as a broad band of $M_r$ of 76,500 to 97,000. These $M_r$ are within the reported range for ICAM-1 immunoprecipitated from different cell sources: $M_r = 90,000$ for JY cells, 114,000 on the myelomonocytic cell line U937, and 97,000 on fibroblasts (Dustin et al., *J. Immunol.* 137:245 (1986) This wide range in $M_r$ has been attributed to an extensive, but variable degree of glycosylation. The non-glycosylated precursor has a $M_r$ of 55,000 (Dustin et al.). The protein purified from either JY cells or human spleen retains its antigenic activity as evidenced by its ability to re-bind to the original affinity column, and by immunoprecipitation with RR1/1-Sepharose and SDS-polyacrylamide electrophoresis.

To produce peptide fragments of ICAM-1, approximately 200 μg was reduced with 2 mM dithiothreitol/2% SDS, followed by alkylation with 5 mM iodoacetic acid. The protein was precipitated with ethanol, and redissolved in 0.1 M $NH_4CO_3$/0.1 mM $CaCl_2$/0.1% zwittergent 3-14 (Calbiochem), and digested with 1% w/w trypsin at 37° C. for 4 hours, followed by an additional digestion with 1% trypsin for 12 hours at 37° C. The tryptic peptides were purified by reverse-phase HPLC using a 0.4×15 cm C4 column (Vydac). The peptides were eluted with a linear gradient of 0% to 60⅒: acetonitrile in 0.1% trifluoroacetic acid. Selected peptides were subjected to sequence analysis on a gas phase microsequenator (Applied Biosystems). The sequence information obtained from this study is shown in Table 6.

TABLE 6

Amino Acid Sequences of ICAM-1 Tryptic Peptides

| Amino Acid Residue | 50a | 50b | 46a | 46b | X | 45 | K | AA | J | U | O | M1 |
|---|---|---|---|---|---|---|---|---|---|---|---|---|
| 1 | [T/V] | A | (V/A) | E | V | S | L | E | A | L | V | L |
| 2 | F | S | Q | P | E | F | N | L | G | L | T | L/E |
| 3 | L | I | T | A | L | P | P | D | S | G | L | P/(G) |
| 4 | T | S | F | | A | A | T | L | V | I | | P |
| 5 | V | L | P | | P | P | V | R | L | E | | G/Y |
| 6 | Y | G | L | | L | N | T | P | V | T | | N/L |
| 7 | P | W | P | | P | V | Y | Q | T | P | | (N) |
| 8 | T | P | I | | I | T/I | G | G | C | P/V | | (Q) |
| 9 | S | F | G | | (G) | L | — | L | S | K | | (E) |
| 10 | E | | E | | (Q) | — | D | E | T | | | (D) |
| 11 | A | | S | | D/P | K | S | L | S | | | |
| 12 | G/S | | V | | V | P | F | F | C | | | |
| 13 | A | | T | | D | Q | S | E | D | | | |
| 14 | G | | V | | W | V/L | A | — | Q | | | |
| 15 | | | | | | I | K | T | P | | | |
| 16 | | | | | | | | S | K | | | |
| 17 | | | | | | | | A | | | | |
| 18 | | | | | | | | P | | | | |
| 19 | | | | | | | | X | | | | |
| 20 | | | | | | | | Q | | | | |

TABLE 6-continued

| Amino Acid Sequences of ICAM-1 Tryptic Peptides | | | | | | | | | | | |
|---|---|---|---|---|---|---|---|---|---|---|---|
| Amino Acid Residue | 50a | 50b | 46a | 46b | X | 45 | K | AA | J | U | O | M1 |
| 21 | | | | | | | | | L | | | |

( ) = Low confidence sequence.
[ ] = Very low confidence sequence.
/ = Indicates ambiguity in the sequence; most probable amino acid is listed first.
a = Major peptide.
b = Minor peptide.

EXAMPLE 16

Cloning of the ICAM-1 Gene

The gene for ICAM-1 may be cloned using any of a variety of procedures. For example, the amino acid sequence information obtained through the sequencing of the tryptic fragments of ICAM-1 (Table 6) can be used to identify an oligonucleotide sequence which would correspond to the ICAM-1 gene. Alternatively, the ICAM-1 gene can be cloned using anti-ICAM-1 antibody to detect clones which produce ICAM-1.

Cloning of the gene for ICAM-1 through the use of oligonucleotide probes

Using the genetic code (Watson, J. D., In: *Molecular Biology of the Gene*, 3rd Ed., W. A. Benjamin, Inc., Menlo Park, Calif. (1977)), one or more different oligonucleotides can be identified, each of which would be capable of encoding the ICAM-1 tryptic peptides. The probability that a particular oligonucleotide will, in fact, constitute the actual ICAM-1 encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence (i.e. the nucleotide sequence having the lowest redundancy) capable of encoding the ICAM-1 tryptic peptide sequences is identified.

The oligonucleotide, or set of oligonucleotides, containing the theoretical "most probable" sequence capable of encoding the ICAM-1 fragments is used to identify the sequence of a complementary oligonucleotide or set of oligonucleotides which is capable of hybridizing to the "most probably" sequence, or set of sequences. An oligonucleotide containing such a complementary sequence can be employed as a probe to identify and isolate the ICAM-1 gene (Maniatis, T., et al., *Molecular Cloning A Laboratory Manual*, Cold Spring Harbor Press, Cold Spring Harbor, N.Y. (1982).

As described in Section C, supra, it is possible to clone the ICAM-1 gene from eukaryotic DNA preparations suspected of containing this gene. To identify and clone the gene which encodes the ICAM-1 protein, a DNA library is screened for its ability to hybridize with the oligonucleotide probes described above. Because it is likely that there will be only two copies of the gene for ICAM-1 in a normal diploid cell, and because it is possible that the ICAM-1 gene may have large non-transcribed intervening sequences (introns) whose cloning is not desired, it is preferable to isolate ICAM-1-encoding sequences from a CDNA library prepared from the MRNA of an ICAM-1-producing cell, rather than from genomic DNA. Suitable DNA, or CDNA preparations are enzymatically cleaved, or randomly sheared, and ligated into recombinant vectors. The ability of these recombinant vectors to hybridize to the above-described oligonucleotide probes is then measured. Procedures for hybridization are disclosed, for example, in Maniatis, T., *Molecular Cloning A Laboratory Manual*, Cold Spring Harbor Press, Cold Spring Harbor, N.Y. (1982) or in Haymes, B. T., et al., *Nucleic Acid Hybridization a Practical Approach*, IRL Press, Oxford, England (1985). Vectors found capable of such hybridization are then analyzed to determine the extent and nature of the ICAM-1 sequences which they contain. Based purely on statistical considerations, a gene such as that which encodes the ICAM-1 molecule could be unambiguously identified (via hybridization screening) using an oligonucleotide probe having only 18 nucleotides.

Thus, in summary, the actual identification of ICAM-1 peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate the ICAM-1 gene.

Using the ICAM-1 peptide sequences of Table 6, the sequence of the "most probable" sequence of an oligonucleotide capable of encoding the AA and J peptides was determined (Tables 7 and 8, respectively). Oligonucleotides complementary to these sequences were synthesized and purified for use as probes to isolate ICAM-1 gene sequences. Suitable size-selected CDNA libraries were generated from the poly(A)+ RNA of both PMA-induced HL-60 cells and from PS-stimulated umbilical vein endothelial cells. A size-selected CDNA library was prepared using poly(A)+ RNA from PMA-induced HL-60 cells according to the method of Gubler, U., et al. ((*Gene* 25:263–269 (1983)) and Corbi, A., et al. (*EMBO J.* 6:4023–4028 (1987)), which references are herein incorporated by reference.

A size-selected CDNA library was prepared using poly(A) RNA+ RNA from umbilical vein endothelial cells which had been stimulated for 4 hours with PS 5 $\mu$g/ml. The RNA was extracted by homogenizing the cells in 4 M guanidinium isothiocyanate and subjecting the supernatant to ultracentrifugation through a CsCl gradient (Chirgwin, J. M., et al., *Biochem.* 18:5294–5299 (1979)). Poly(A)+ RNA was isolated from the mixture of total RNA species through the use of oligo (dT)-cellulose chromatography (Type 3, Collaborative Research) (Aviv, H., et al., *Proc. Natl. Acad. Sci.* (*USA*) 69:1408–1412 (1972).

TABLE 7

Oligonucleotide Complementary to the Most Probable Nucleotide Sequence Capable of Encoding the ICAM-1 AA Peptide

| Amino Acid Residue of ICAM-1 | ICAM-1 AA Peptide | Most Probable Sequence Encoding AA Peptide (5'→3') | Complementary Sequence (3'→5') |
|---|---|---|---|
| 162 | Glu | G A G | C T C |
| 163 | Leu | C T G | G A C |
| 164 | Asp | G A C | C T G |
| 165 | Leu | C T G | G A C |
| 166 | Arg | C G G | G C C |
| 167 | Pro | C C C | G G G |
| 168 | Gln | C A G | G T C |
| 169 | Gly | G G C | C C G |
| 170 | Leu | C T G | G A C |
| 171 | Glu | G A G | C T C |
| 172 | Leu | C T G | G A C |
| 173 | Phe | T T T | A A A |
| 174 | Glu | G A G | C T C |
| 175 | Asn | A A C | T T G |
| 176 | Thr | A C C | T G G |
| 177 | Ser | U C A | A G T |

TABLE 8

Oligonucleotide Complementary to the Most Probable Nucleotide Sequence Capable of Encoding the ICAM-1 J Peptide

| Amino Acid Residue of ICAM-1 | ICAM-1 AA Peptide | Most Probable Sequence Encoding AA Peptide (5'→3') | Complementary Sequence (3'→5') |
|---|---|---|---|
| 19 | Val | G T G | C A C |
| 20 | Thr | A C C | T G G |
| 21 | Cys | T G C | A C G |
| 22 | Ser | T C C | A G G |
| 23 | Thr | A C C | T G G |
| 24 | Ser | T C C | A G G |
| 25 | Cys | T G T | A C A |
| 26 | Asp | G A C | C T G |
| 27 | Gln | C A G | G T C |
| 28 | Pro | C C C | G G G |
| 29 | Lys | A A A | T T T |

First strand cDNA was synthesized using 8 μg of poly(A)+ RNA, avian myeloblastosis virus reverse transcriptase (Life Sciences) and an oligo(dT) primer. The DNA-RNA hybrid was digested with RNase H (BRL) and the second strand was synthesized using DNA polymerase I (New England Biolabs). The product was methylated with Eco R1 methylase (New England Biolabs), blunt end ligated to Eco R1 linkers (New England Biolabs), digested with Eco R1 and size selected on a low melting point agarose gel. cDNA greater than 500bp were ligated to λgt10 which had previously been Eco R1 digested and dephosphorylated (Stratagene) The product of the ligation was then packaged (Stratagene gold).

The umbilical vein endothelial cell and HL-60 cDNA libraries were then plated at 20,000 PFU/150 mm plate. Recombinant DNA was transferred in duplicate to nitrocellulose filters, denatured in 0.5 M NaOH/1.5M NaCl, neutralized in 1M Tris, pH7.5/1.5M NaCl and baked at 80° C. for 2 hours (Benton, W. D., et al., Science 196:180–182 (1977)). Filters were prehybridized and hybridized in 5X SSC containing 5X Denhardt's solution, 50 mM NaPO$_4$ and 1 μg/ml salmon sperm DNA. Prehybridization was carried out at 45° for 1 hour.

Hybridization was carried out using 32bp ('5-TTGGGCTGGTCACAGGAGGTGGAGCAGGT-GAC) or 47bp (5'-GAGGTGTTCTCAAACAGCT-CCAGGCCCTGG GGCCGCAGGTCCAGCTC) anti-sense oligonucleotides based, in the manner discussed above, on the ICAM-1 tryptic peptides J and AA, respectively (Tables 7 and 8) (Lathe, R., J. Molec. Biol., 183:1–12 (1985)). Oligonucleotides were end labeled with γ-($^{32}$P)ATP using T4 polynucleotide kinase and conditions recommended by the manufacturer (New England Biolabs). Following overnight hybridization the filters were washed twice with 2X SSC/0.1% SDS for 30 minutes at 45° C. Phages were isolated from those plaques which exhibited hybridization, and were purified by successive replating and rescreening.

Cloning of the gene for ICAM-1 through the use of anti-ICAM-1 antibody

The gene for ICAM-1 may alternatively be cloned through the use of anti-ICAM-1 antibody. DNA, or more preferably cDNA, is extracted and purified from a cell which is capable of expressing ICAM-1. The purified cDNA is fragmentized (by shearing, endonuclease digestion, etc.) to product a pool of DNA or cDNA fragments. DNA or cDNA fragments from this pool are then cloned into an expression vector in order to produce a genomic library of expression vectors whose members each contain a unique cloned DNA or cDNA fragment.

EXAMPLE 17

Analysis of the cDNA clones

Phage DNA from positive clones were digested with Eco R1 and examined by Southern analysis using a cDNA from one clone as a probe. Maximal size cDNA inserts which cross-hybridized were subcloned into the Eco R1 site of plasmid vector PGEM 4Z (Promega). HL-60 subclones containing the cDNA in both orientations were deleted by exonuclease III digestion (Henikoff, S., *Gene* 28:351-359 (1984)) according to the manufacturers recommendations (Erase-a-Base, Promega). Progressively deleted cDNAs were then cloned and subjected to dideoxynucleotide chain termination sequencing (Sanger, F. et al., *Proc. Natl. Acad. Sci. (USA)* 74:5463-5467 (1977)) according to the manufacturers recommendations (Sequenase, U.S. Biochemical). The HL-60 cDNA 5' and coding regions were sequenced completely on both strands and the 3' region was sequenced approximately 70% on both strands. A representative endothelial cDNA was sequenced over most of its length by shotgun cloning of 4bp-recognition restriction enzyme fragments.

The cDNA sequence of one HL-60 and one endothelial cell cDNA was established (FIG. 8). The 3023 bp sequence contains a short 5' untranslated region and a 1.3 kb 3' untranslated region with a consensus polyadenylation signal at position 2966. The longest open reading frame begins with the first ATG at position 58 and ends with a TGA terminating triplet at position 1653. Identity between the translated amino acid sequence and sequences determined from 8 different tryptic peptides totaling 91 amino acids (underlined in FIG. 8) confirmed that authentic ICAM-1 cDNA clones had been isolated. The amino acid sequences of ICAM-1 tryptic peptides are shown in Table 9.

TABLE 9

Amino Acid Sequences of ICAM-1 Tryptic Peptides

| Peptide | Residues | Sequence |
|---------|----------|----------|
| J | 14–29 | X G S V L <u>V T C S T S C D Q P K</u> |
| U | 30–39 | L L G I E T P L (P) (K) |
| 50 | 78–85 | (T) F L T V Y X T |
| X | 89–95 | V E L A P L P |
| AA | 161–182 | X <u>E L D L R P Q G L E</u> —<br><u>L F E X T S</u> A P X Q L |
| K | 232–246 | L N P T V T Y G X D S F S A K |
| 45 | 282–295 | S F P A P N V (T/I) L X K P Q (V/L) |

—Indicates that the sequence continues on the next line. Underlined sequences were used to prepare oligonucleotide probes.

Hydrophobicity analysis (Kyte, J., et al., *J. Molec. Biol.*, 157:105-132 (1982)) suggests the presence of a 27 residue signal sequence. The assignment of the +1 glutamine is consistent with out inability to obtain N-terminal sequence on 3 different ICAM-1 protein preparations; glutamine may cyclize to pyroglumatic acid, resulting in a blocked N-terminus. The translated sequence from 1 to 453 is predominantly hydrophilic followed by a 24 residue hydrophobic putative transmembrane domain. The transmembrane domain is immediately followed by several charged residues contained within a 27 residue putative cytoplasmic domain.

The predicted size of the mature polypeptide chain is 55,219 daltons, in excellent agreement with the observed size of 55,000 for deglycosylated ICAM-1 (Dustin, M. L., et al., *J. Immunol.* 137:245-254 (1986)). Eight N-linked glycosylation sites are predicted. Absence of asparagine in the tryptic peptide sequences of 2 of these sites confirm their glycosylation and their extracellular orientation. Assuming 2,500 daltons per high mannose N-linked carbohydrate, a size of 75,000 daltons is predicted for the ICAM-1 precursor, compared to the observed six of 73,000 daltons (Dustin, M. L., et al., *J. Immunol*. 137: 245-254 (1986)). After conversion of high mannose to complex carbohydrate, the mature ICAM-1 glycoprotein is 76 to 114 kd, depending on cell type (Dustin, M. L., et al., *J. Immunol.* 137:245-254 (1986)). Thus ICAM-1 is a heavily glycosylated but otherwise typical integral membrane protein.

EXAMPLE 18

ICAM-1 is an Integrin-Binding Member of the Immunoglobulin Supergene family

Alignment of ICAM-1 internal repeats was performed using the Microgenie protein alignment program (Queen, C., et al., *Nucl. Acid Res.*, 12:581-599 (1984)) followed by inspection. Alignment of ICAM-1 to IgM, N-CAM and MAG was carried out using Microgenie and the ALIGN program (Dayhoff, M. O., et al., *Meth. Enzygol,* 91:524-545 (1983)). Four protein sequence databases, maintained by the National Biomedical Research Foundation, were searched for protein sequence similarities using the FASTP program of Williams and Pearson (Lipman, D. J., et al., *Science* 227:1435-1439 (1985)).

Since ICAM-1 is a ligand of an integrin, it was unexpected that it would be a member of the immunoglobulin supergene family. However, inspection of the ICAM-1 sequence shows that it fulfills all criteria proposed for membership in the immunoglobulin supergene family. These criteria are discussed in turn below.

The entire extracellular domain of ICAM-1 is constructed from 5 homologous immunoglobulin-like domains which are shown aligned in FIG. 9A. Domains 1–4 are 88, 97, 99, and 99 residues long, respectively and thus are of typical Ig domain size; domain 5 is truncated within 68 residues. Searches of the NBRF data base using the FASTP program revealed significant homologies with members of the immunoglobulin supergene family including IgM and IgG C domains, T cell receptor α subunit variable domain, and alpha 1 beta glycoprotein (FIG. 9B–D).

Using the above information, the amino acid sequence of ICAM-1 was compared with the amino acid sequences of other members of the immunoglobulin supergene family.

Three types of Ig superfamily domains, V, C1, and C2 have been differentiated. Both V and C domains are constructed from 2 β-sheets linked together by the intradomain disulfide bond; V domains contain 9 antiparallel β-strands while C domains have 7. Constant domains were divided into the C1- and C2- sets based on characteristic residues shown in FIG. 9A. The C1-set includes proteins involved in antigen recognition. The C2-set includes several Fc receptors and proteins involved in call adhesion including CD2, LFA-3, MAG, and NCAM. ICAM-1 domains were found to be most strongly homologous with domains of the C2-set placing ICAM-1 in this set; this is reflected in stronger similarity to conserved residues in C2 than C1 domains as shown for β-strands B-F in FIG. 9. Also, ICAM-1 domains aligned much better with β-strands A and G of C2 domains than with these strands in V and C1 domains, allowing good alignments across the entire C2 domain strength. Alignments with C2 domains from NCAM, MAG, and alpha 1-β glycoprotein are shown in FIGS. 9B and 9C; identity ranged from 28 to 33%. Alignments with a T cell receptor Vα 27% identity and IgM C domain 3 34% identity are also shown (FIGS. 9B, 9D).

One of the most important characteristics of immunoglobulin domains is the disulfide-bonded cysteines bridging the B and F β strands which stabilizes the β sheet sandwich; in ICAM-1 the cysteines are conserved in all cases except in strand f of domain 4 where a leucine is found which may face into the sandwich and stabilize the contact as proposed for some other V- and C2-sets domains. The distance between the cysteines (43, 50, 52, and 37 residues) is as described for the C2-set.

To test for the presence of intrachain disulfide bonds in ICAM-1, endothelial cell ICAM-1 was subjected to SDS-PAGE under reducing and non-reducing conditions. Endothelial cell ICAM-1 was used because it shows less glycosylation heterogeneity than JY or hairy cell splenic ICAM-1 and allows greater sensitivity to shifts in $M_r$. ICAM-1 was, therefore, purified from 16 hour LPS (5 μg/ml) stimulated umbilical vein endothelial cell cultures by immunoaffinity chromatography as described above. Acetone precipitated ICAM-1 was resuspended in sample buffer (Laemmli, U. K., Nature 227:680-685 (1970)) with 0.25% 2-mercaptoethanol or 25 mM iodoacetamide and brought to 100° C. for 5 min. The samples were subjected to SDS-PAGE 4670 and silver staining 4613. Endothelial cell ICAM-1 had an apparent $M_r$ of 100 Kd under reducing conditions and 96 Kd under non-reducing conditions strongly suggesting the presence of intrachain disulfides in native ICAM-1.

Use of the primary sequence to predict secondary structure (Chou, P. Y., et al., Biochem. 3:211-245 (1974)) showed the 7 expected β-strands in each ICAM-1 domain, labeled a-g in FIG. 9A upper, exactly fulfilling the prediction for an immunoglobulin domain and corresponding to the positions of strands A-H in immunoglobulins (FIG. 9A, lower). Domain 5 lacks the A and C strands but since these form edges of the sheets the sheets could still form, perhaps with strand D taking the place of strand C as proposed for some other C2 domains; and the characteristic disulfide bond between the B and F strands would be unaffected. Thus, the criteria for domain size, sequence homology, conserve cysteines forming the putative intradomain disulfide bond, presence of disulfide bonds, and predicted β sheet structure are all met for inclusion of ICAM-1 in the immunoglobulin supergene family.

Figure 10:
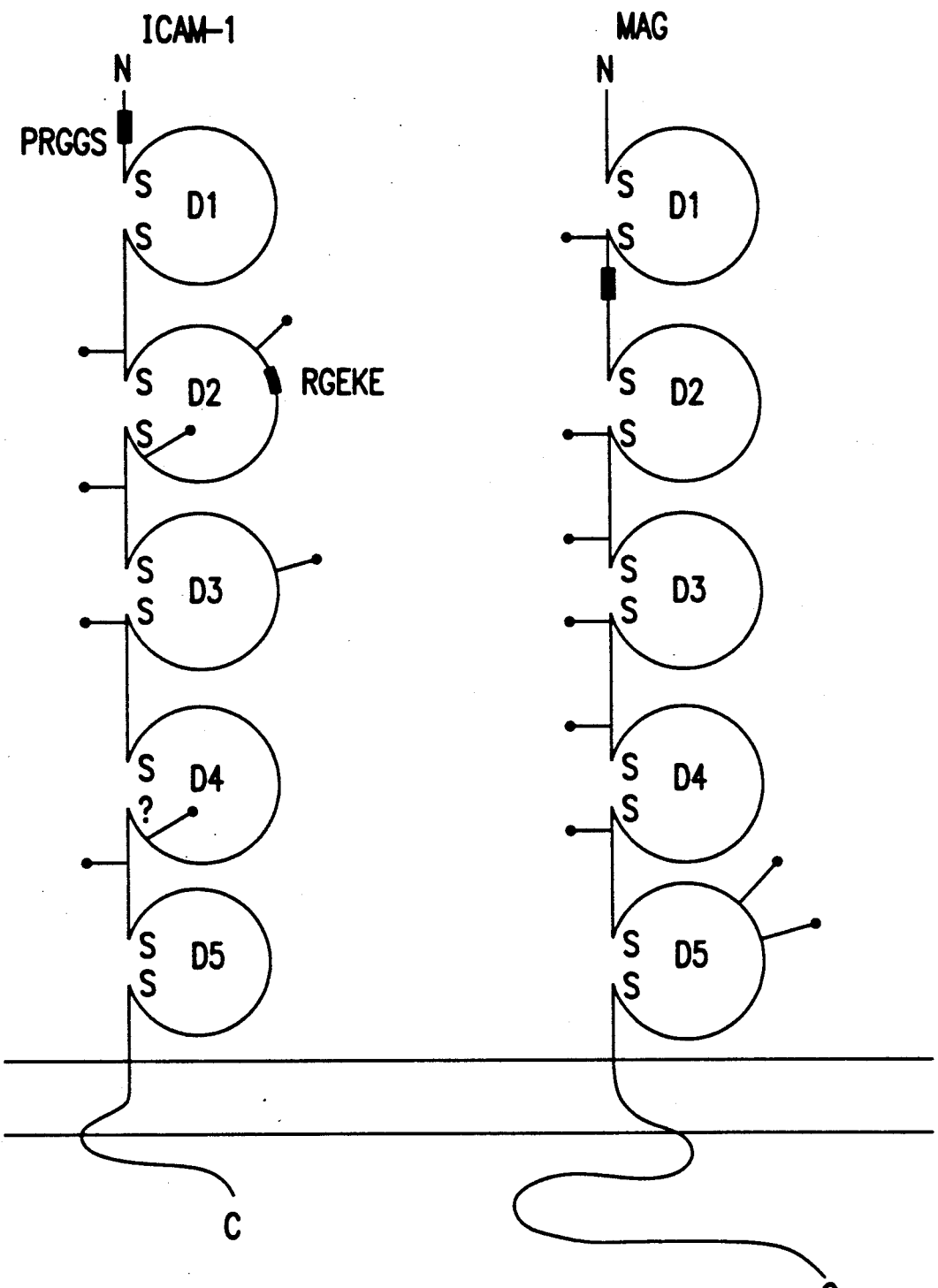
FIG. 10 shows a diagrammatic comparison of the secondary structures of ICAM-1 and MAG.

ICAM-1 was found to be most strongly homologous with the NCAM and MAG glycoproteins of the C2 set. This is of particular interest since both NCAM and MAG mediate cell-cell adhesion. NCAM is important in neuron-neuron and neuromuscular interactions (Cunningham, B. A., et al., Science 236:799-806 (1987) while MAG is important in neuron-oligodendrocyte and oligodendrocyte-oligodendrocyte interactions during myelination (Poltorak, M., et al., i. Cell Biol. 105:1893-1899 (1987)). The cell surface expression of NCAM and MAG is developmentally regulated during nervous system formation and myelination, respectively, in analogy to the regulated induction of ICAM-1 in inflammation (Springer, T. A., et al., Ann. Rev. Immunol. 5:223-252 (1987)). ICAM-1, NCAM (Cunningham, B. A., et al., Science 236:799-806 (1987)), and MAG (Salzer, J. L., et al., J. Cell. Biol. 104:957-965 (1987)) are similar in overall structure as well as homologous, since each is an integral membrane glycoprotein constructed from 5 C2 domains forming the N-terminal extracellular region, although in NCAM some additional non-Ig-like sequence is present between the last C2 domain and the transmembrane domain. ICAM-1 aligns over its entire length including the transmembrane and cytoplasmic domains with MAG with 21% identity; the same % identity is found comparing the 5 domains of ICAM-1 and NCAM-1. A diagrammatic comparison of the secondary structures of ICAM-1 and MAG is shown in FIG. 10. Domain by domain comparisons show that the level of homology between domains within the ICAM-1 and NCAM molecules (x±s.d. 21±2.8% and 18.6±3.8%, respectively) is the same as the level of homology comparing ICAM-1 domains to NCAM and MAG domains (20.4±3.7 and 21.9±2.7, respectively). Although there is evidence for alternative splicing in the C-terminal regions of NCAM (Cunningham, B. A., et al., Science 236:799-806 (1987); Barthels, D., et al., EMBO J. 6:907-914 (1987)) and MAG (Lai, C., et al., Proc. Natl. Acad. Sci. (USA) 84:4377-4341 (1987)), no evidence for this has been found in the sequencing of endothelial or HL-60 ICAM-1 clones or in studies on the ICAM-1 protein backbone and precursor in a variety of cell types (Dustin, M. L., et al., J. Immunol. 137:245-254 (1986)).

ICAM-1 functions as a ligand for LFA-1 in lymphocyte interactions with a number of different cell types. Lymphocytes bind to ICAM-1 incorporated in artificial membrane bilayers, and this requires LFA-1 on the lymphocyte, directly demonstrating LFA-1 interaction with ICAM-1 (Marlin, S. D., et al., cell 51:813-819 (1987)). LFA-1 is a leukocyte integrin and has no immunoglobulin-like features. Leukocyte integrins comprise one integrin subfamily. The other two subfamilies mediate cell-matrix interactions and recognize the sequence RGD within their ligands which include fibronectin, vitronectin, collagen, and fibrinogen (Hynes, R. O., Cell 48:549-554 (1987); Ruoslahti, E., et al., Science 238:491-497 (1987)). The leukocyte integrins are only expressed on leukocytes, are involved in cell-cell interactions, and the only known ligands are ICAM-1 and iC3b, a fragment of the complement component C3 which shows no immunoglobulin-like features and is recognized by Mac-1 (Kishimoto, T. K., et al., In: Leukocyte Typing III, McMichael, M. (ed.), Springer-Verlag, New York (1987); Springer, T. A., et al., Ann. Rev. Immunol. 5:223-252 (1987); Anderson, D. C., et al., Ann. Rev. Med. 38:175-194 (1987)). Based upon sequence analysis, possible peptides within the ICAM-1 sequence recognized by LFA-1 are shown in Table 10.

TABLE 10

Peptides Within the ICAM-1 Sequence Possibly Recognized by LFA-1

—L—R—G—E—K—E—L—
—R—G—E—K—E—L—K—R—E—P—
—L—R—G—E—K—E—L—K—R—E—P—A—V—G—E—P—A—E—
—P—G—N—N—R—K—
—Q—E—D—S—Q—P—M—
—T—P—E—R—V—E—L—A—P—L—P—S—
—R—R—D—H—H—G—A—N—F—S—
—D—L—R—P—Q—G—L—E—

ICAM-1 is the first example of a member of the immunoglobulin supergene family which binds to an integrin. Although both of these families play an important role in cell adhesion, interaction between them had not previously been expected. In contrast, interactions within the immunoglobulin gene superfamily are quite common. It is quite possible that further examples of interactions between the integrin and immunoglobulin families will be found. LFA-1 recognizes a ligand distinct from ICAM-1 (Springer, T. A., et al., *Ann. Rev. Immunol.* 5:223-252 (1987)), and the leukocyte integrin Mac-1 recognizes a ligand distinct from C36i in neutrophil-neutrophil adhesion (Anderson, D. C., et al., *Ann. Rev. Med.* 38:175-194 (1987)). Furthermore, purified MAG-containing vesicles bind to neurites which are MAG, and thus MAG must be capable of heterophilic interaction with a distinct receptor (Poltorak, M., et al., *J. Cell Biol.* 105:1893-1899 (1987)).

NCAM's role in neural-neural and neural-muscular cell interactions has been suggested to be due to homophilic NCAM-NCAM interactions (Cunningham, B. A., et al., *Science* 236:799-806 (1987)). The important role of MAG in interactions between adjacent turning loops of Schwann cells enveloping axons during myelin sheath formation might be due to interaction with a distinct receptor, or due to homophilic MAG-MAG interactions. The homology with NCAM and the frequent occurrence of domain-domain interactions within the immunoglobulin supergene family raises the possibility that ICAM-1 could engage in homophilic interactions as well as ICAM-1-LFA-1 heterophilic interactions. However, binding of B lymphoblast cells which co-express similar densities of LFA-1 and ICAM-1 to ICAM-1 in artificial or cellular monolayers can be completely inhibited by pretreatment of the B lymphoblast with LFA-1 MAb, while adherence is unaffected by B lymphoblast pretreatment with ICAM-1 MAb. Pretreatment of the monolayer with ICAM-1 Mab completely abolishes binding (Dustin, M. L., et al., *J. Immunol.* 137:245-254 (1986); Marlin, S. D., et al., *cell* 51:813-819 (1987)). These findings show that if ICAM-1 homophilic interactions occur at all, they must be much weaker than heterophilic interaction with LFA-1.

The possibility that the leukocyte integrins recognize ligands in a fundamentally different way is consistent with the presence of a 180 residue sequence in their a subunits which may be important in ligand binding and which is not present in the RGD-recognizing integrins (Corbi, A., et al. (*EMBO J.* 6:4023-4028 (1987)). Although Mac-1 has been proposed to recognize RGD sequence present in iC3b 5086, there is no RGD sequence in ICAM-1 (FIG. 8). This is in agreement with the failure of the fibronectin peptide GRGDSP and the control peptide GRGESP to inhibit ICAM-1-LFA-1 adhesion (Marlin, S. D., et al., *cell* 51:813-819 (1987)). However, related sequences such as PRGGS and RGEKE are present in ICAM-1 in regions predicted to loop between β strands a and b of domain 2 and c and d of domain 2, respectively (FIG. 9), and thus may be accessible for recognition. It is of interest that the homologous MAG molecule contains an RGD sequence between domains 1 and 2 (Poltorak, M., et al., *J. Cell Biol.* 105:1893-1899 (1987); Salzer, J. L., et al., *J. Cell. Biol.* 104:957-965 (1987)).

EXAMPLE 19

Southern and Northern Blots

Southern blots were performed using a 5 µg of genomic DNA extracted from three cell lines: BL2, a Burkitt lymphoma cell line (a gift from Dr. Gilbert Lenoir); JY and ER-LCL, EBV transformed B-lymphoblastoid cell lines.

The DNAs were digested with 5× the manufacturers recommended quantity of Bam H1 and Eco R1 endonucleases (New England Biolabs). Following electrophoresis through a 0.8% agarose gel, the DNAs were transferred to a nylon membrane (Zeta Probe, BioRad). The filter was prehybridized and hybridized following standard procedures using ICAM cDNA from HL-60 labeled with $\alpha$-($^{32}$P)d XTP's by random priming (Boehringer Mannheim). Northern blots were performed using 20 µg of total RNA or 6 µg of poly(A)+ RNA. RNA was denatured and electrophoresed through a 1% agarose-formaldehyde gel and electrotransferred to Zeta Probe. Filters were prehybridized and hybridized as described previously (Staunton, D. E., et al. *Embo J.* 6:3695-3701 (1987)) using the HL-60 cDNA probe of $^{32}$P-labeled oligonucleotide probes (described above).

The Southern blots using the 3 kb cDNA probe and genomic DNA digested with Bam H1 and Eco R1 showed single predominant hybridizing fragments of 20 and 8 kb, respectively, suggesting a single gene and suggesting that most of the coding information is present within 8 kb. In blots of 3 different cell lines there is no evidence of restriction fragment polymorphism.

EXAMPLE 20

Expression of the ICAM-1 Gene

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing ICAM-1 in order to produce a prokaryotic genomic expression vector library. Procedures for preparing cDNA and for producing a genomic library are disclosed by Maniatis, T., et al. (*Molecular Clonina: Laboratory Manual*, Cold Spring Harbor Press, Cold Spring Harbor, N.Y. (1982)).

The above-described expression vector genomic library is used to create a bank of host cells (each of which contains one member of the library). The expression vector may be introduced into the host cell by any of a variety of means (i.e., transformation, transfection, protoplast fusion, electroporation, etc.). The bank of expression vector-containing cells is clonally propagated, and its members are individually assayed (using an immunoassay) to determine whether they produce a protein capable of binding to anti-ICAM-1 antibody.

The expression vectors of those cells which produce a protein capable of binding to anti-ICAM-1 antibody are then further analyzed to determine whether they express (and thus contain) the entire ICAM-1 gene, whether they express (and contain) only a fragment of the ICAM-1 gene, or whether they express (and contain) a gene whose product, though immunologically related to ICAM-1, is not ICAM-1. Although such an analysis may be performed by any convenient means, it is preferable to determine the nucleotide sequence of the DNA or cDNA fragment which had been cloned into the expression vector. Such nucleotide sequences are then examined to determine whether they are capable of encoding polypeptides having the same amino acid sequence as the tryptic digestion fragments of ICAM-1 (Table 6).

An expression vector which contains a DNA or cDNA molecule which encodes the ICAM-1 gene may, thus, be recognized by: (i) the ability to direct the expression of a protein which is capable of binding to anti-ICAM-1 antibody; and (ii) the presence of a nucleotide sequence which is capable of encoding each of the tryptic fragments of ICAM-1. The cloned DNA molecule of such an expression vector may be removed from the expression vector and isolated in pure form.

EXAMPLE 21

Functional Activities of Purified ICAM-1

In cells, ICAM-1 normally functions as a surface protein associated with the cell membrane. Therefore, the function of purified ICAM-1 was tested after the molecule was reconstituted into artificial lipid membranes (liposomes, or vesicles) by dissolving the protein in detergent-solubilized lipids, followed by the removal of the detergent by dialysis. ICAM-1 purified from JY cells and eluted in the detergent octylglucoside as described above was reconstituted into vesicles, and the ICAM-1 containing vesicles were fused to glass coverslips or plastic culture wells to allow the detection of cells binding to the protein.

Preparation of planar membranes and plastic-bound vesicles

Vesicles were prepared by the method of Gay et al. (J. Immunol. 136:2026 (1986) Briefly, egg phosphatidylcholine and cholesterol were dissolved in chloroform and mixed in a molar ratio of 7:2. The lipid mixture was dried to a thin film while rotating under a stream of nitrogen gas, and was then lyophilized for I hour to remove all traces of chloroform. The lipid film was then dissolved in 1% octylglucoside/0.14 M NaCl/20 mM Tris (pH 7.2) to a final concentration of phosphatidylcholine of 0.1 mM. Approximately 10 μg of purified ICAM-1 or human glycophorin (Sigma Chemical Co., St. Louis, Mo.) as a control membrane glycoprotein, was added to each ml of dissolved lipids. The protein-lipid-detergent solution was then dialyzed at 4° C. against 3 changes of 200 volumes of 20 mM Tris/0.14 M NaCl, pH 7.2, and one change of HBSS.

Planar membranes were prepared by the method of Brian et al., Proc. Natl. Acad. Sci. 81:6159 (1984). Glass coverslips (11 Mm in diameter) were boiled for 15 minutes in a 1:6 dilution of 7× detergent (Linbro), washed overnight in distilled water, soaked in 70% ethanol, and air dried. An 80 μl drop of vesicle suspension containing either ICAM-1 or glycophorin was placed in the bottom of wells in a 24-well cluster plate, and the prepared glass coverslips were gently floated on top. After 20-30 minutes incubation at room temperature, the wells were filled with HBSS, and the coverslips were inverted to bring the planar membrane face up. The wells were then washed extensively with HBSS to remove unbound vesicles. The planar membrane surface was never exposed to air.

In the course of experiments with planar membrane fused to glass surfaces, vesicles containing ICAM-1 were found to bind directly to the plastic surface of multi-well tissue culture plates, and retain functional activity as evidenced by specific cell binding. Such vesicles are hereinafter referred to as "plastic-bound vesicles" (PBV) since the nature of the lipid vesicles bound to the plastic has not been determined. Plastic-bound vesicles were prepared by adding 30 μl of vesicle suspension directly to the bottom of wells in 96-well tissue culture trays (Falcon), followed by incubation and washing as described for planar membranes.

Cell adhesion assays

Cell adhesion assays using planar membranes or plastic-bound vesicles were both done in essentially the same way, except that the cell numbers and volumes for PBV assays were reduced to one-fifth that used in planar membrane assays.

T-lymphocytes from normal controls and a Leukocyte Adhesion Deficiency (LAD) patient whose cells fail to express LFA-1 (Anderson, D. C. et al., J. Infect. Dis. 152:668 (1985)) were prepared by culturing peripheral blood mononuclear cells with 1 μg/ml Concanavalin-A (Con-A) in RPMI-1640 plus 20% FCS at $5 \times 10^5$ cells/ml for 3 days. The cells were then washed twice with RPMI and once with 5 mM methyl-alpha-D-mannopyranoside to remove residual lectin from the cell surface. The cells were grown in RPMI/20% FCS containing 1 ng/ml recombinant IL-2, and were used between 10 and 22 days after the initiation of culture.

To detect cell binding to planar membranes or PBV, Con-A blasts, the T-lymphoma SKW-3, and the EBV-transformed B-lymphoblastoid cell lines JY (LFA-1 positive) and LFA-1 deficient lymphoblastoid cell line (BBN) (derived from patient 1, Springer, T. A. et al., J. Exper. Med. 160:1901-1918 (1986) were radiolabeled by incubation of $1 \times 10^7$ cells in 1 ml of RPMI-1640/10% FCS with 100 μCi of $Na^{51}CrO_4$ for 1 hour at 37° C., followed by four washes with RPMI-1640 to remove unincorporated label. In monoclonal antibody blocking experiments, cells or plastic-bound vesicles were pretreated with 20 μg/ml of purified antibody in RPMI-1640/10% FCS at 4° C. for 30 minutes, followed by 4 washes to remove unbound antibody. In experiments on the effects of divalent cations on cell binding, the cells were washed once with $Ca^{2+}$, $Mg^{2+}$-free HBSS plus 10% dialyzed FCS, and CaCl and MgCl were added to the indicated concentrations. In all experiments, cells and planar membranes or PBV were pre-equilibrated at the appropriate temperature (4° C., 22° C., or 37° C.) in the appropriate assay buffer.

To measure cell binding to purified ICAM-1, $^{51}$Cr-labeled cells ($5 \times 10^5$ EBV-transformants in planar membrane assays; $1 \times 10^5$ EBV-transformants or SKW-3 cells, $2 \times 10^5$ Con-A blasts in PBV assays) were centrifuged for 2 minutes at 25 ×g onto planar membranes or PBV, followed by incubation at 4° C., 22° C., or 37° C. for one hour. After incubation, unbound cells were removed by eight cycles of filling and aspiration with buffer pre-equilibrated to the appropriate temperature. Bound cells were quantitated by solubilization of well contents with 0.1 N NaOH/1% Triton X-100 and counting in a gamma counter. Percent cell binding was determined by dividing cpm from bound cells by input cell-associated cpm. In planar membrane assays, input cpm were corrected for the ratio of the surface area of coverslips compared to the surface area of the culture wells.

Figure 11:
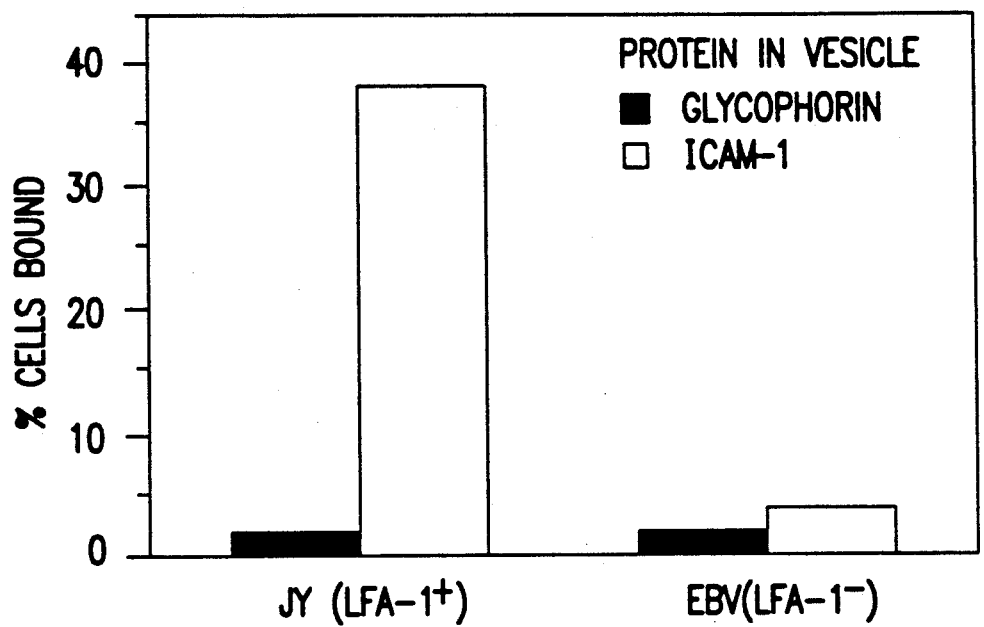
FIG. 11 shows LFA-1-positive EBV-transformed B-lymphoblastoid cells binding to ICAM-1 in planar membranes.
Figure 12A:
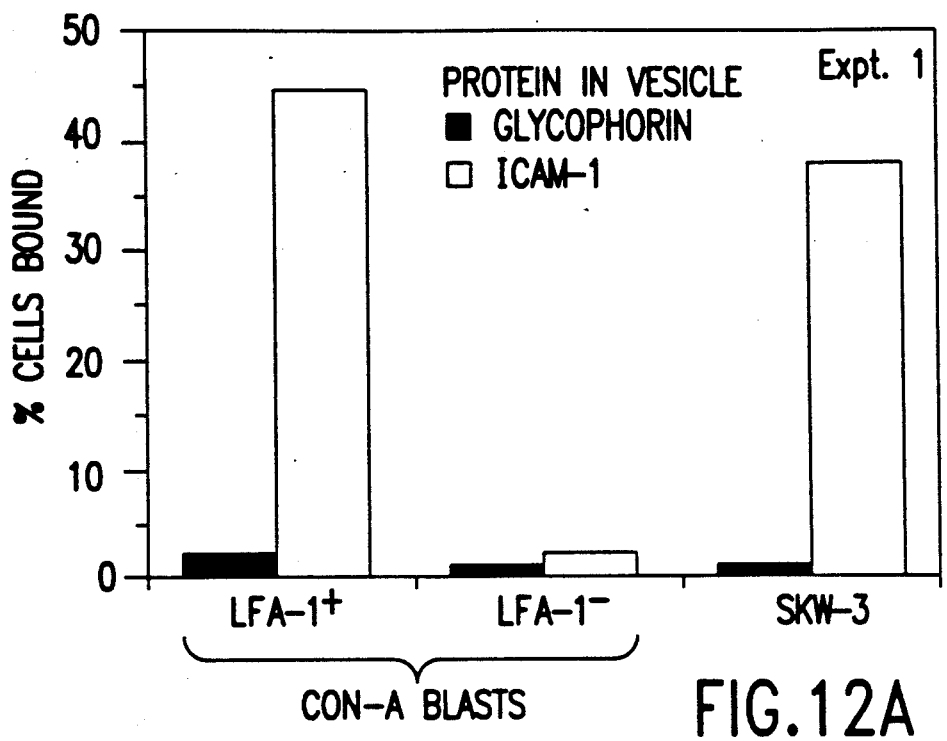
FIG. 12 (Panels A-B) shows L A-1-positive T lymphoblasts and T lymphoma cells bind to ICAM-1 in plastic-bound vesicles.
Figure 12B:
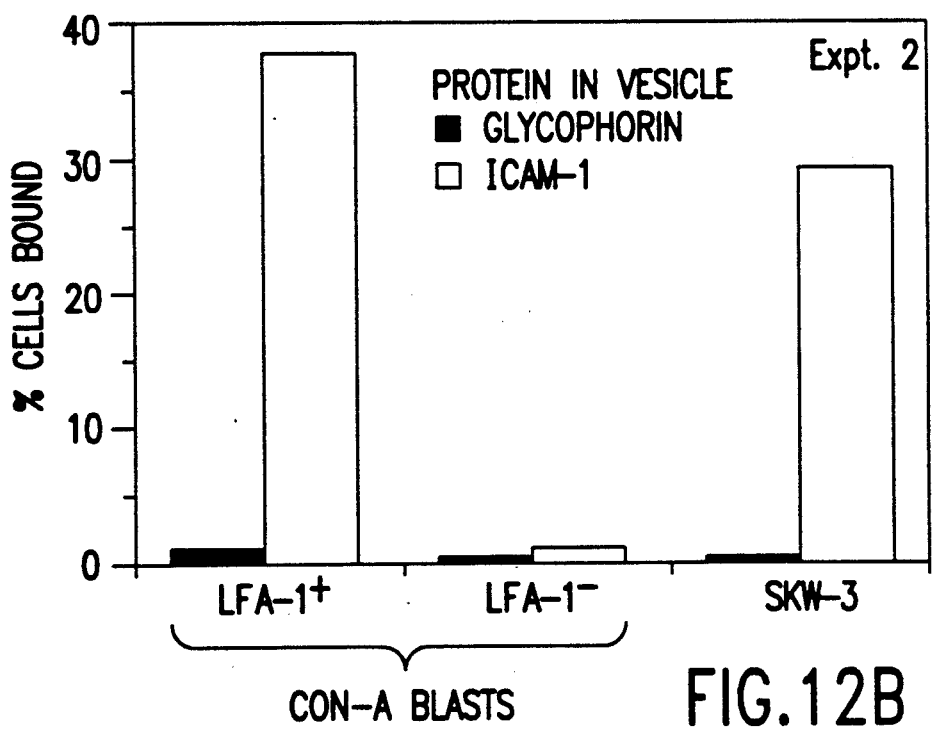

In these assays, EBV-transformed B-lymphoblastoid cells, SKW-3 T-lymphoma cells, and Con-A T-lymphoblasts bound specifically to ICAM-1 in artificial membranes (FIGS. 11 and 12). The binding was specific since the cells bound very poorly to control planar membranes or vesicles containing equivalent amounts of another human cell surface glycoprotein, glycophorin. Furthermore, LFA-1 positive EBV-transformants and Con-A blasts bound, while their LFA-1 negative counterparts failed to bind to any significant extent, demonstrating that the binding was dependent on the presence of LFA-1 on the cells.

Figure 13:
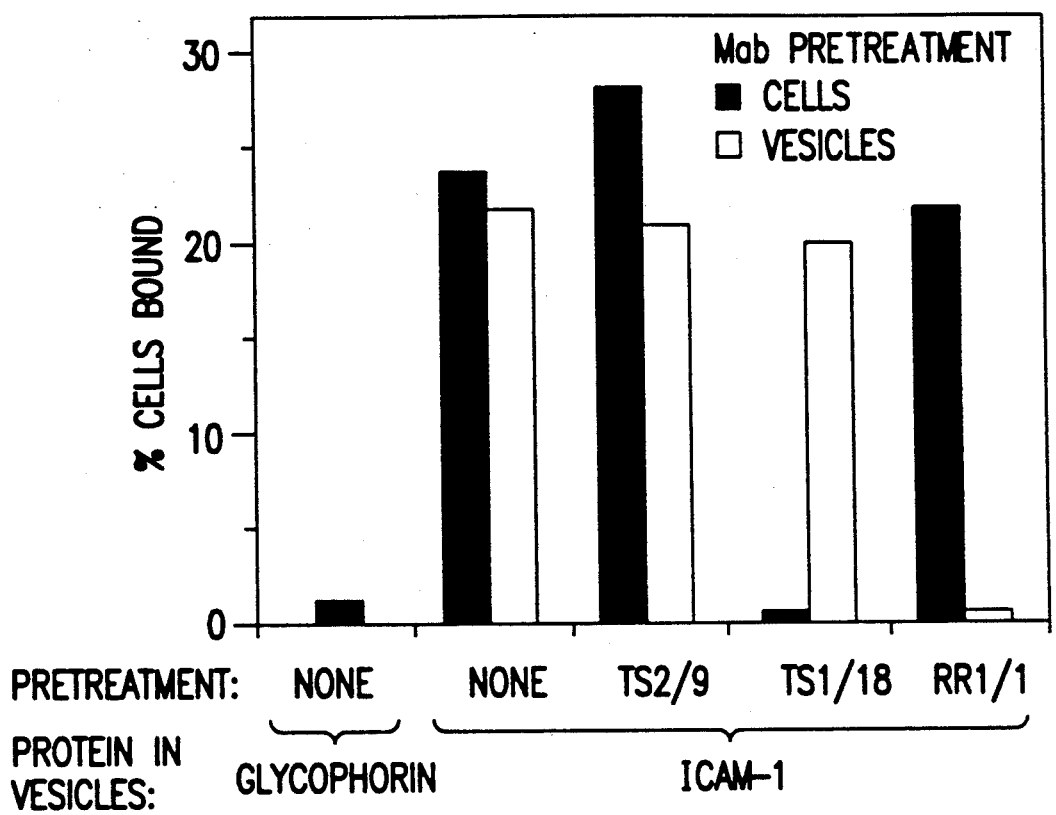
FIG. 13 shows the inhibition of binding of JY B-lymphoblastoid cell binding to ICAM-1 in plastic-bound vesicles by pretreatment of cells or vesicles with monoclonal antibodies.

Both the specificity of cell binding and the dependence on cellular LFA-1 were confirmed in monoclonal antibody blocking experiments (FIG. 13). The binding of JY cells could be inhibited by 97% when the ICAM-1-containing PBV were pretreated with anti-ICAM-1 monoclonal antibody RR1/1. Pretreatment of the cells with the same antibody had little effect. Conversely, the anti-LFA-1 monoclonal antibody TS1/18 inhibited binding by 96%, but only when the cells, but not the PBV, were pretreated. A control antibody TS2/9 reactive with LFA-3 (a different lymphocyte surface antigen) had no significant inhibitory effect when either cells or PBV were pretreated. This experiment demonstrates that ICAM-1 itself in the artificial membranes, and not some minor contaminant, mediates the observed cellular adhesion and that the adhesion is dependent on LFA-1 on the binding cell.

Figure 14:
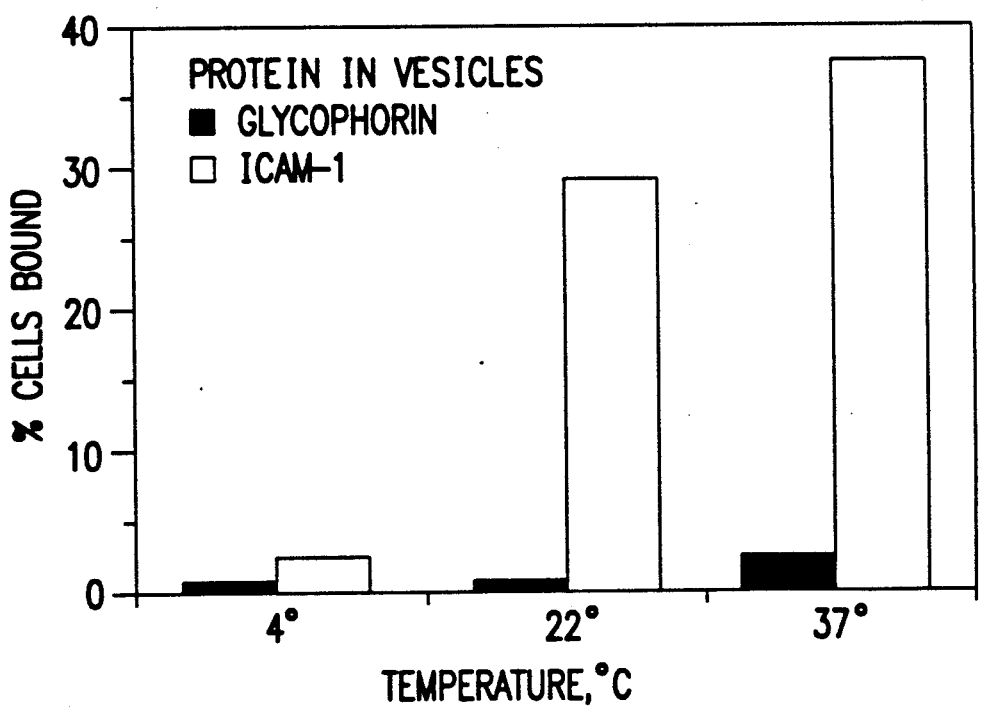
FIG. 14 shows the effect of temperature on binding of T-lymphoblasts to ICAM-1 in plastic-bound vesicles.
Figure 15:
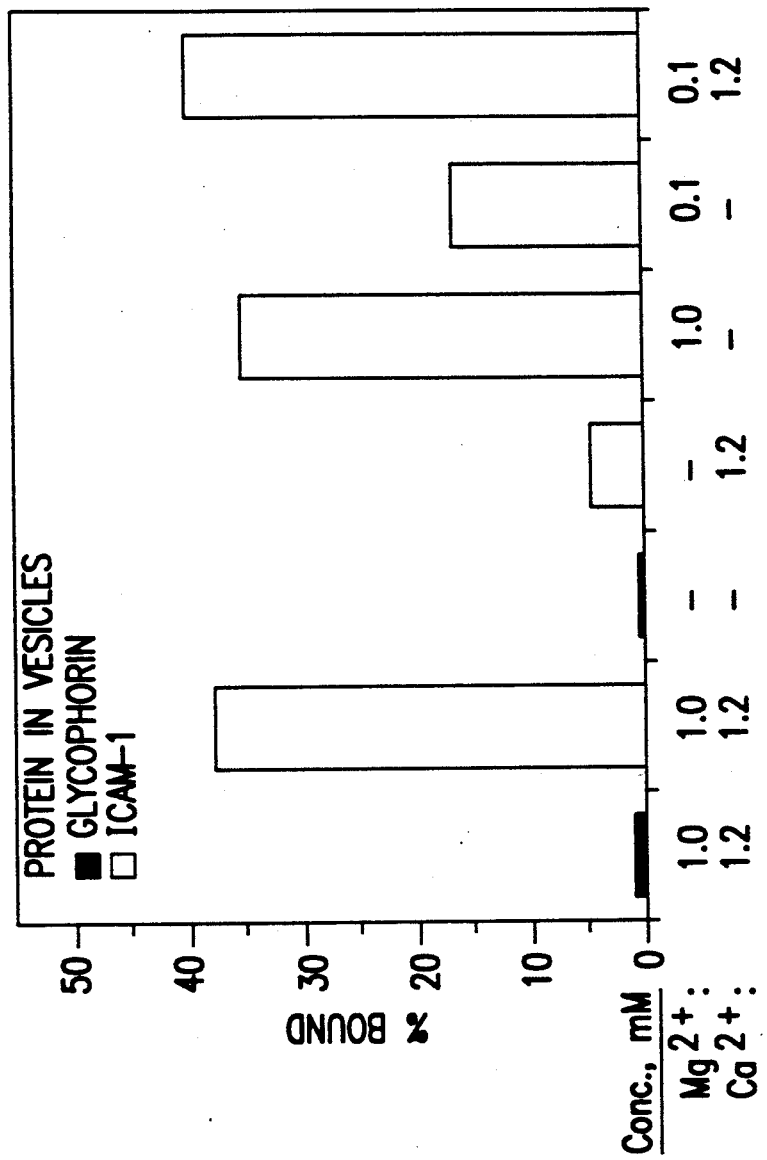
FIG. 15 shows divalent cation requirements for binding of T-lymphoblasts to ICAM-1 in plastic-bound vesicles.

The binding of cells to ICAM-1 in artificial membranes also displayed two other characteristics of the LFA-1 dependent adhesion system: temperature dependence and a requirement for divalent cations. As shown in FIG. 14, Con-A blasts bound to ICAM-1 in PBV most effectively at 37° C., partially at 22° C., and very poorly at 4° C. As shown in FIG. 15, the binding was completely dependent on the presence of divalent cations. At physiological concentrations, $Mg^{2+}$ alone was sufficient for maximal cell binding, while $Ca^{2+}$ alone produced very low levels of binding. However, $Mg^{2+}$ at one-tenth of the normal concentration combined with $Ca^{2+}$ was synergistic and produced maximal binding.

In summary, the specificity of cell binding to purified ICAM-1 incorporated into artificial membranes, the specific inhibition with monoclonal antibodies, and the temperature and divalent cation requirements demonstrate that ICAM-1 is a specific ligand for the LFA-1-dependent adhesion system.

EXAMPLE 22

Expression of ICAM-1 and HLA-DR in Allergic and Toxic Patch Test Reactions

Skin biopsies of five normal individuals were studied for their expression of ICAM-1 and HLA-DR. It was found that while the endothelial cells in some blood vessels usually expressed ICAM-1, there was no ICAM-1 expressed on keratinocytes from normal skin. No staining for HLA-DR on any keratinocyte from normal skin biopsies was observed. The kinetics of expression of ICAM-1 and class II antigens were then studied on cells in biopsies of allergic and toxic skin lesions. It was found that one-half of the six subjects studied had keratinocytes which expressed ICAM-1, four hours after application of the hapten (Table 11). There was an increase in the percentage of individuals expressing ICAM-1 on their keratinocytes with time of exposure to the hapten as well as an increase in the intensity of staining indicating more ICAM-1 expression per keratinocyte up to 48 hours. In fact, at this time point a proportion of keratinocytes in all biopsies stained positively for ICAM-1. At 72 hours (24 hours after the hapten was removed), seven of the eight subjects still had ICAM-1 expressed on their keratinyocytes while the expression of ICAM-1 on one subject waned between 48 and 72 hours.

TABLE 11

| Kinetics of Induction of ICAM-1 and HLA-DR on Keratinocytes from Allergic Patch Test Biopsies | | | | |
|---|---|---|---|---|
| Time After Patch Application (h) | No. of Biopsies | ICAM-1 Only | HLA-DR Only | ICAM-1 & HLA-DR |
| Normal Skin | 5 | 0 | 0 | 0 |
| Allergic Patch Test | | | | |
| 4 | 6 | 3[a] | 0 | 0 |
| 8 | 9 | 3 | 0 | 0 |
| 24 | 8 | 7 | 0 | 0 |
| 48[b] | 8 | 5 | 0 | 3 |
| 72 | 8 | 6 | 0 | 1 |

[a]Samples were considered as positive if at least small clusters of keratinocytes were stained.
[b]All patches were removed at this point.

[a]Samples were considered as positive if at least small clusters of keratinocytes were stained.

[b]All patches were removed at this time point.

Histologically, the staining pattern for ICAM-1 on keratinocytes from biopsies taken four hours after application of the hapten was usually in small clusters. At 48 hours, ICAM-1 was expressed on the surface of the majority of the keratinocytes, no difference being seen between the center and periphery of the lesion. The intensity of the staining decreased as the keratinocytes approached the stratum corneum. This was found in biopsies taken from both the center and the periphery of the lesions.. Also at this time point, the patch test was positive (infiltration, erythema and vesicles). No difference in ICAM-1 expression was observed when different haptens were applied on sensitive individuals. In addition to keratinocytes, ICAM-1 was also expressed on some mononuclear cells and endothelial cells at the site of the lesion.

The expression of HLA-DR on keratinocytes in the allergic skin lesions was less frequent than that of ICAM-1. None of the subjects studied had lesions with keratinocytes that stained positively for HLA-DR up to 24 hours after the application of the hapten. In fact, only four biopsy samples had keratinocytes that expressed HLA-DR and no biopsy had keratinocytes that was positive for HLA-DR and not ICAM-1 (Table 11).

In contrast to the allergic patch test lesion, the toxic patch test lesion induced with croton oil or sodium lauryl sulfate had keratinocytes that displayed little if any ICAM-1 on their surfaces at all time points tested (Table 12). In fact, at 48 hours after the patch application, which was the optimum time point for ICAM-1 expression in the allergic patch test subjects, only one of the 14 toxic patch test subjects had keratinocytes expressing ICAM-1 in their lesions. Also in contrast to the allergic patch test biopsies, there was no HLA-DR expressed on keratinocytes of toxic patch test lesions.

These data indicate that ICAM-1 is expressed in immune-based inflammation and not in toxic based inflammation, and thus the expression of ICAM-1 may be used to distinguish between immuno based and toxic based inflammation, such as acute renal failure in kidney transplant patients where it is difficult to determine whether failure is due to rejection or nephrotoxicity of the immuno-suppressive therapeutic agent. Renal biopsy and assessment of upregulation of ICAM-1 expression will allow differentiation of immune based rejection and non-immune based toxicity reaction.

TABLE 12

Kinetics of Induction of ICAM-1 and HLA-DR on Keratinocytes from Toxic Patch Test Biopsies

| Time After Patch Application (h) | No. of Biopsies | ICAM-1 Only | HLA-DR Only | ICAM-1 & HLA-DR |
|---|---|---|---|---|
| 4 | 4 | 0 | 0 | 0 |
| 8 | 3 | 1[a] | 0 | 0 |
| 24 | 3 | 1 | 0 | 0 |
| 48[b] | 14 | 1 | 0 | 0 |
| 72 | 3 | 1 | 0 | 0 |

[a]Samples were considered as positive if at least small clusters of keratinocytes were stained.
[b]All patches were removed at this time point.

EXAMPLE 23

Expression of ICAM-1 and HLA-DR in Benign Cutaneous Diseases

Cells form skin biopsies of lesions form patients with various types of inflammatory skin diseases were studied for their expression of ICAM-1 and HLA-DR. A proportion of keratinocytes in biopsies of allergic contact eczema, pemphigoid/pemphigus and lichen planus expressed ICAM-1. Lichen planus biopsies showed the most intense staining with a pattern similar to or even stronger than that seen in the 48-hour allergic patch test biopsies (Table 13). Consistent with results seen in the allergic patch test, the most intensive ICAM-1 staining was seen at sites of heavy mononuclear cell infiltration. Furthermore, 8 out of the 11 Lichen planus biopsies tested were positive for HLA-DR expression on keratinocytes.

The expression of ICAM-1 on keratinocytes from skin biopsies of patients with exanthema and urticaria was less pronounced. Only four out of the seven patients tested with these diseases had keratinocytes that expressed ICAM-1 at the site of the lesion. HLA-DR expression was only found on one patient and this was in conjunction with ICAM-1.

Endothelial cells and a proportion of the mononuclear cell infiltrate from all the benign inflammatory skin diseases tested expressed ICAM-1 to a varying extent.

TABLE 13

Expression of ICAM-1 and HLA-DR on Keratinocytes from Benign Cutaneous Diseases

| Diagnosis | No. of Cases | ICAM-1 Only | HLA-DR Only | ICAM-1 & HLA-DR |
|---|---|---|---|---|
| Allergic Contact Eczema | 5 | 3[a] | 0 | 2 |
| Lichen Planus | 11 | 3 | 0 | 8 |
| Pemphigoid/Pemphigus | 2 | 2 | 0 | 0 |
| Exanthema | 3 | 2 | 0 | 0 |
| Urticaria | 4 | 1 | 0 | 1 |

[a]Samples were considered as positive if at least small clusters of keratinocytes were stained.

EXAMPLE 24

Expression of ICAM-1 on Keratinocytes of Psoriatic Skin Lesions

The expression of ICAM-1 in skin biopsies from 5 patients with psoriasis were studied before the initiation and periodically during a course of PUVA treatment. Biopsies were obtained from 5 patients with classical psoriasis confirmed by histology. Biopsies were taken sequentially before and during indicated time of PUVA treatment. PUVA was given 3 to 4 times weekly. Biopsies were taken from the periphery of the psoriatic plaques in five patients and, in addition biopsies were taken from clinically normal skin in four of the patients. Fresh skin biopsy specimens were frozen and stored in liquid nitrogen. Six micron cryostat sections were air dried overnight at room temperature, fixed in acetone for 10 minutes and either stained immediately or wrapped in aluminum foil and stored at $-80°$ C. until staining.

Staining was accomplished in the following manner. Sections were incubated with monoclonal antibodies and stained by a three stage immunoperoxidase method (Stein, H., et. al., Adv. Cancer Res 42:67–147, (1984)), using a diaminobenzidine $H_2O_2$, substrate. Tonsils and lymph nodes were used as positive control for anti-ICAM-1 and HLA-DR staining. Tissue stained in the absence of primary antibody were negative controls.

The monoclonal antibodies against HLA-DR were purchased from Becton Dickinson (Mountainview, Calif.). The monoclonal anti-ICAM-1 antibody was R6-5-D6. Peroxidase-conjugated rabbit anti-mouse Ig and peroxidase-conjugated swine anti-rabbit Ig were purchased from DAKAPATTS, Copenhagen, Denmark. Diaminobenzidine-tetrahydrochloride were obtained from Sigma (St. Louis, Mo.).

The results of the study show that the endothelial cells in some blood vessels express ICAM-1 in both diseased and normal skin, but the intensity of staining and the number of blood vessels expressing ICAM-1 was increased in the psoriatic skin lesions. Moreover, the pattern of expression of ICAM-1 in keratinocytes of untreated psoriatic skin lesions from the five patients varied from only small clusters of cells staining to many keratinocytes being stained. During the course of PUVA treatment, the ICAM-1 expression on 2 of the patients (patients 2 and 3) showed marked reduction which preceded or was concurrent with clinical remission (Table 14). Patients 1, 4 and 5 had decreases and increases of ICAM-1 expression during the PUVA treatment which correlated to clinical remissions and relapses, respectively. There was no ICAM-1 expression on keratinocytes from normal skin before or after PUVA treatment. This indicates that PUVA does not induce ICAM-1 on keratinocytes from normal skin.

Of note was the observation that the density of the mononuclear cell infiltrate correlated with the amount of ICAM-1 expression on keratinocytes. This pertained to both a decreased number of mononuclear cells in lesions during PUVA treatment when ICAM-1 expression also waned and an increased number of mononuclear cells during PUVA treatment when ICAM-1 expression on keratinocytes was more prominent. Endothelial cells and dermal mononuclear cells are also ICAM-1-positive. In clinically normal skin, ICAM-1 expression was confined to endothelial cells with no labelling of keratinocytes.

The expression of HLA-DR on keratinocytes was variable. There was no HLA-DR positive biopsy that was not also ICAM-1 positive.

In summary, these results show that before treatment, ICAM-1 expression is pronounced on the keratinocytes and correlate to a dense mononuclear cellular infiltrate. During PUVA treatment a pronounced decrease of the ICAM-1 staining is seen to parallel the clinical improvement. Histologically the dermal infiltrate also diminished. When a clinical relapse was obvious during treatment, the expression of ICAM-1 on the keratinocytes increased, as well as the density of the dermal infiltrate. When a clinical remission was seen during treatment, there was a concurrent decrease in ICAM-1 staining on the keratinocytes as well as decrease in the dermal infiltrate. Thus the expression of ICAM-1 on keratinocytes corresponded to the density of the mononuclear cellular infiltrate of the dermis. These data show that clinical response to PUVA treatment resulted in a pronounced decrease of ICAM-1 expression on keratinocytes parallel to a more moderate decline of the mononuclear cells. This indicates that ICAM-1 expression on keratinocytes is responsible for initiating and maintaining the dermal infiltrate and that PUVA treatment down regulates ICAM-1 which in turn mitigates the dermal infiltrate and the inflammatory response. The data also indicates that there was variable HLA-DR expression on keratinocytes during PUVA treatment.

The expression of ICAM-1 on keratinocytes of psoriatic lesions correlates with the clinical severity of the lesion as well as with the size of the dermal infiltrate. Thus ICAM-1 plays a central role in psoriasis and inhibition of its expression and/or inhibition of its interaction with the CD 18 complex on mononuclear cells will be an effective treatment of the disease. Furthermore, monitoring ICAM-1 expression on keratinocytes will be an effective tool for diagnosis and prognosis, as well as evaluating the course of therapy of psoriasis.

TABLE 14

Sequential ICAM-1 Expression by Keratinocytes in Psoriatic Skin Lesions (PS) and Clinically Normal Skin (N) Before and During PUVA Treatment

| Time before and during PUVA treatment | patient no. | | | | | | | |
|---|---|---|---|---|---|---|---|---|
| | 1 | 2 | | 3 | | 4 | | 5 |
| | PS | PS | N | PS | N | PS | N | PS | N |
| 0 | + | + | − | ++ | − | ++ | − | +++ | − |
| 1 day | + | | | | | | | | |
| 1 week | +○ | + | − | − | − | ++ | − | + | − |
| 2 weeks | ++ | | | + | − | + | − | + | − |
| 3 weeks | ++ | | | | | * | ○ | | |
| 4 weeks | ++ | +● | − | − | − | ++ | − | | * |
| 5-6 weeks | | − | − | | | | | − | − |
| 7 weeks | ● | | | | | (++) | (+) | +++ | − |
| 10 weeks | (+) | | | | | | | − | − |

+++ Many positive keratinocytes
++ A proposition of positive keratinocytes
+ Focal positive keratinocytes
(+) Very few scattered positive keratinocytes
− No positive staining
*Clinical remission
○ Clinical relapse

EXAMPLE 25

Expression of ICAM-1 and HLA-DR in Malignant Cutaneous Diseases

Unlike lesions from benign cutaneous conditions, the expression of ICAM-1 on keratinocytes form malignant skin lesions was much more variable (Table 15). Of the 23 cutaneous T-cell lymphomas studied, ICAM-1 positive keratinocytes were identified in only 14 cases. There was a tendency for keratinocytes form biopsies of mycosis fungoides lesions to lose their ICAM-1 expression with progression of the disease to more advanced stages. However, ICAM-1 expression was observed on a varying proportion of the mononuclear cell infiltrate from most of the cutaneous T cell lymphoma lesions. Among the remaining lymphomas studied, four of eight had keratinocytes that expressed ICAM-1. Of the 29 patients with malignant cutaneous diseases examined, 5 had keratinocytes that expressed HLA-DR without expressing ICM-1 (Table 15).

TABLE 15

Expression of ICAM-1 and HLA-DR on Keratinocytes from Malignant Cutaneous Diseases

| Diagnosis | No. of Cases | ICAM-1 Only | HLA-DR Only | ICAM-1 & HLA-DR |
|---|---|---|---|---|
| CTCL, MFI | 8 | 1[a] | 0 | 4 |
| CTCL, MFII-III | 10 | 1 | 2 | 5 |
| CTCL, SS | 3 | 1 | 0 | 2 |
| CTCL, Large Cell | 2 | 0 | 2 | 0 |
| CBCL | 2 | 0 | 0 | 1 |
| Leukemia Cutis | 3 | 1 | 1 | 1 |
| Histiocytosis X | 1 | 0 | 0 | 0 |

[a]Samples were considered as positive if at least small clusters of keratinocytes were stained.

EXAMPLE 26

Effect of Anti-ICAM-1 Antibodies on the Proliferation of Human Peripheral Blood Mononuclear Cells Human peripheral blood mononuclear cells are induced to proliferate by the presence and recognition of antigens or mitogens. Certain molecules, such as the mitogen, concanavalin A, or the T-cell-binding antibody OKT3, cause a non-specific proliferation of peripheral blood mononuclear cells to occur.

Human peripheral blood mononuclear cells are heterogeneous in that they are composed of subpopulations of cells which are capable of recognizing specific antigens. When a peripheral blood mononuclear cell which is capable of recognizing a particular specific antigen, encounters the antigen, the proliferation of that subpopulation of mononuclear cell is induced. Tetanus toxoid and keyhole limpet hemocyanin are examples of antigens which are recognized by subpopulations of peripheral mononuclear cells but are not recognized by all peripheral mononuclear cells in sensitized individuals.

The ability of anti-ICAM-1 monoclonal antibody R6-5-D6 to inhibit proliferative responses of human peripheral blood mononuclear cells in systems known to require cell-cell adhesions was tested.

Peripheral blood mononuclear cells were purified on Ficoll-Paque (Pharmacia) gradients as per the manufacturer's instructions. Following collection of the interface, the cells were washed three times with RPMI 1640 medium, and cultured in flat-bottomed 96-well microtiter plates at a concentration of $10^6$ cells/ml in RPMI 1640 medium supplemented with 10% fetal bovine serum, 2 mM glutamine, and gentamicin (50 μg/ml).

Antigen, either the T-cell mitogen, concanavalin A (0.25 μg/ml); the T-cell-binding antibody, OKT3 (0.001 μg/ml); keyhole limpet hemocyanin (10 g/ml) or tetanus toxoid (1:100 dilution from source) were added to cells which were cultured as described above in either the presence or absence of anti-ICAM antibody (R6-5-D6; final concentration of 5 g/ml). Cells were cultured for 3.5 days (concanavalin A experiment), 2.5 days (OKT3 experiment), or 5.5 days (keyhole limpet hemocyanin and tetanus toxoid experiments) before the assays were terminated.

Figure 16:
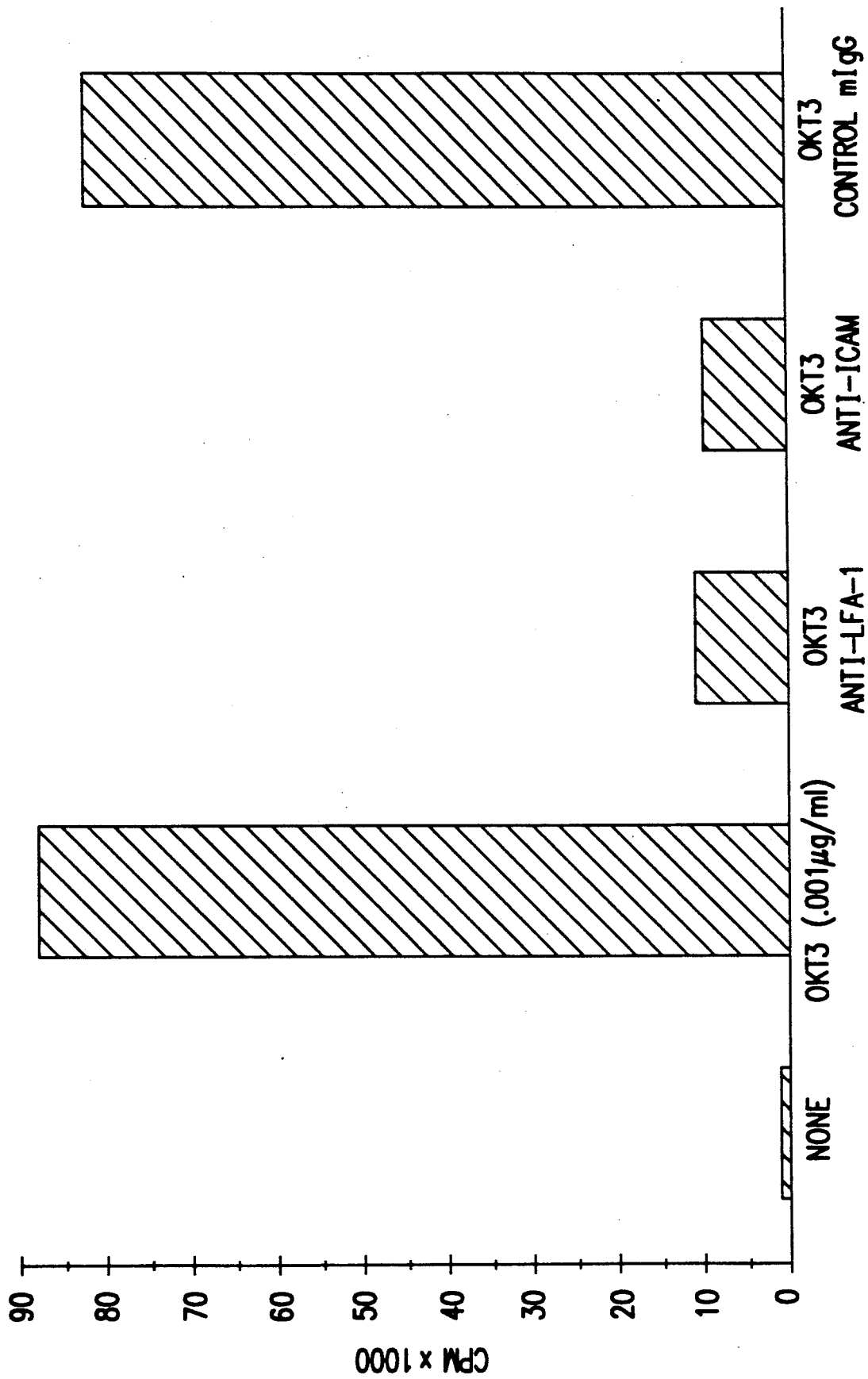
FIG. 16 shows the effect of anti-adhesion antibodies on the ability of peripheral blood mononuclear cells to proliferate in response to the recognition of the T-cell associated antigen OKT3. "OKT3" indicates the addition of antigen.
Figure 17:
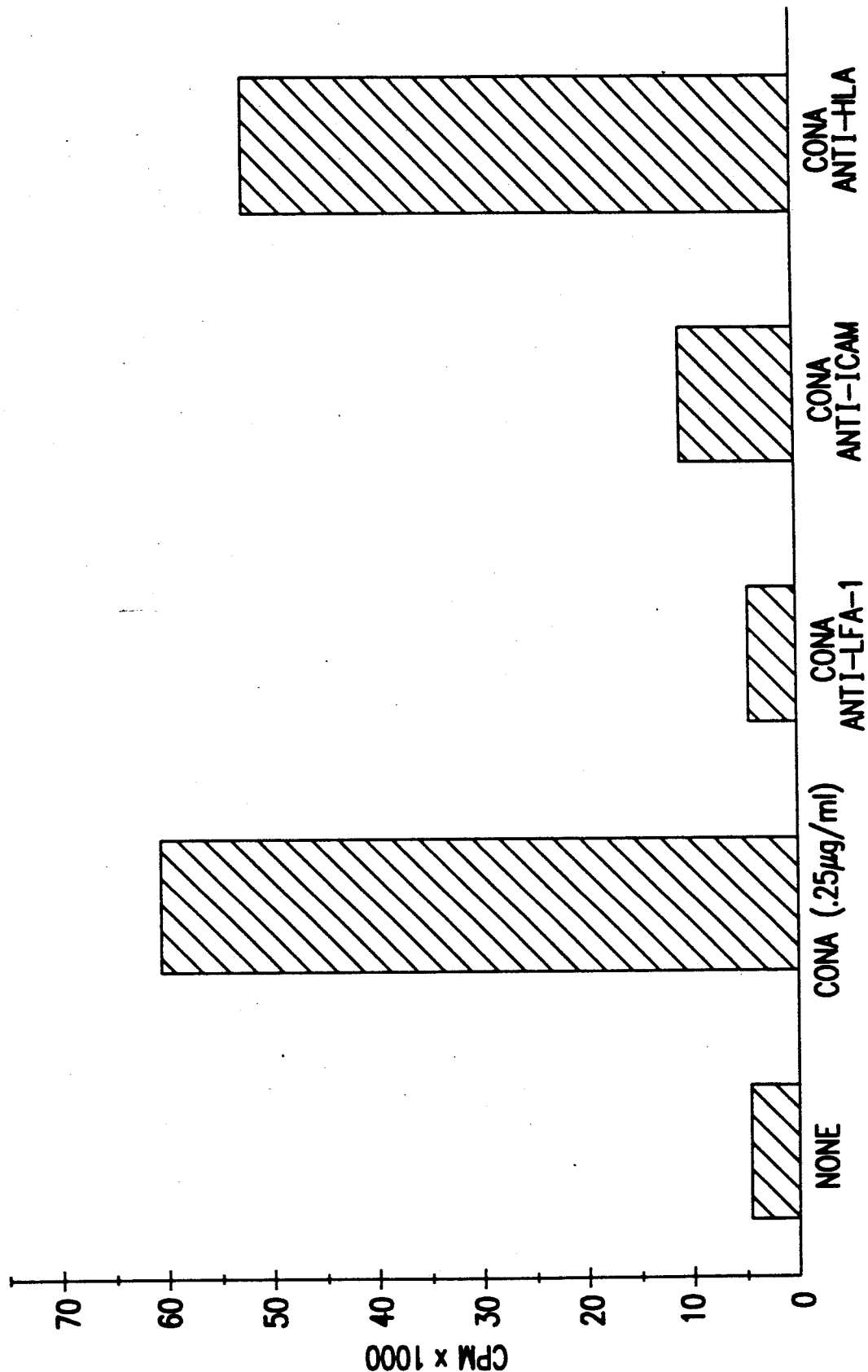
FIG. 17 shows the effect of anti-adhesion antibodies on the ability of peripheral blood mononuclear cells to proliferate in response to the recognition of the non-specific T-cell mitogen, concanavalin A. "CONA" indicates the addition of concanavalin A.
Figure 18:
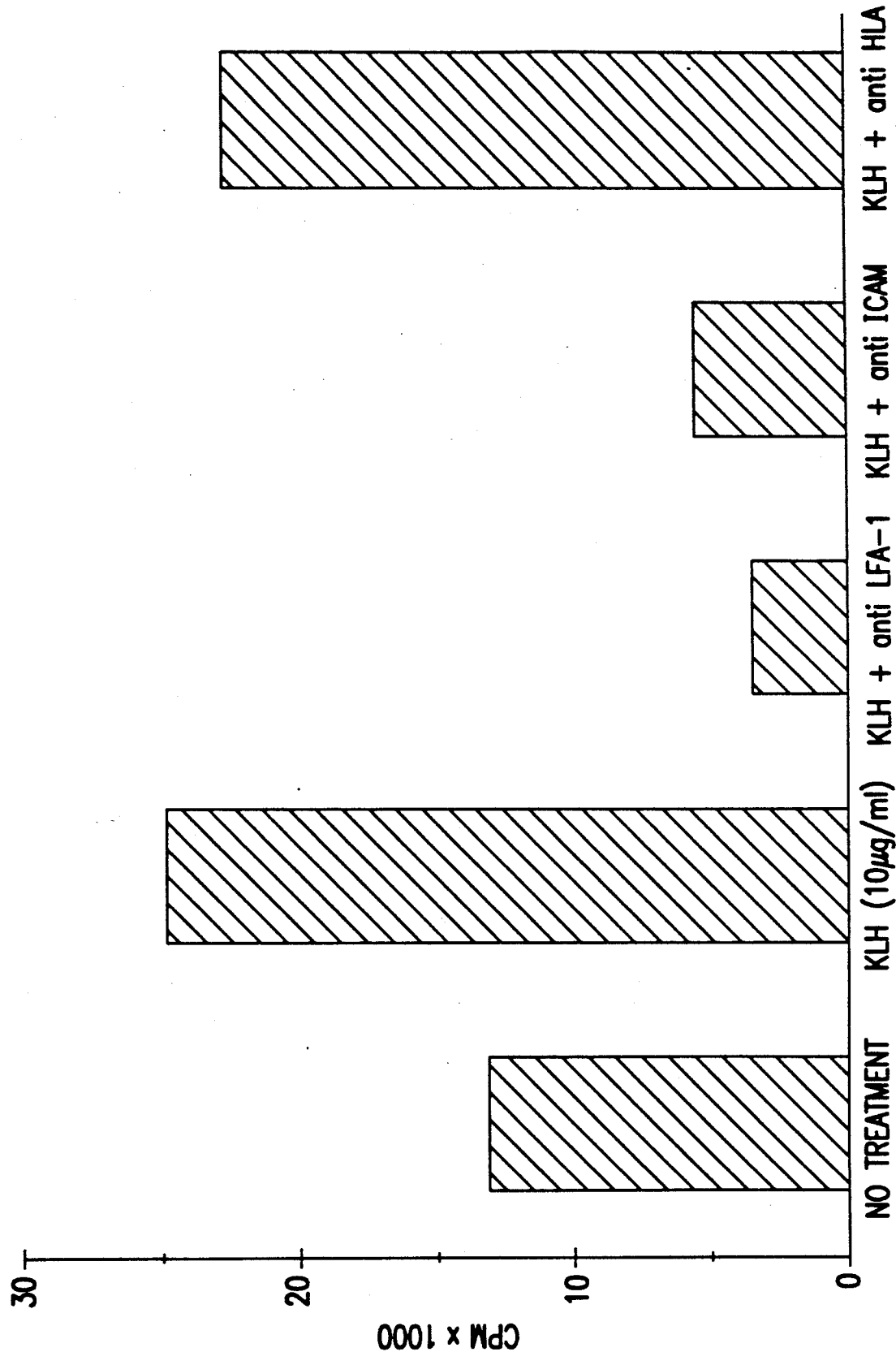
FIG. 18 shows the effect of anti-adhesion antibodies on the ability of peripheral blood mononuclear cells to proliferate in response to the recognition of the keyhole limpet hemocyanin antigen. The addition of keyhole limpet hemocyanin to the cells is indicated by "KLH."
Figure 19:
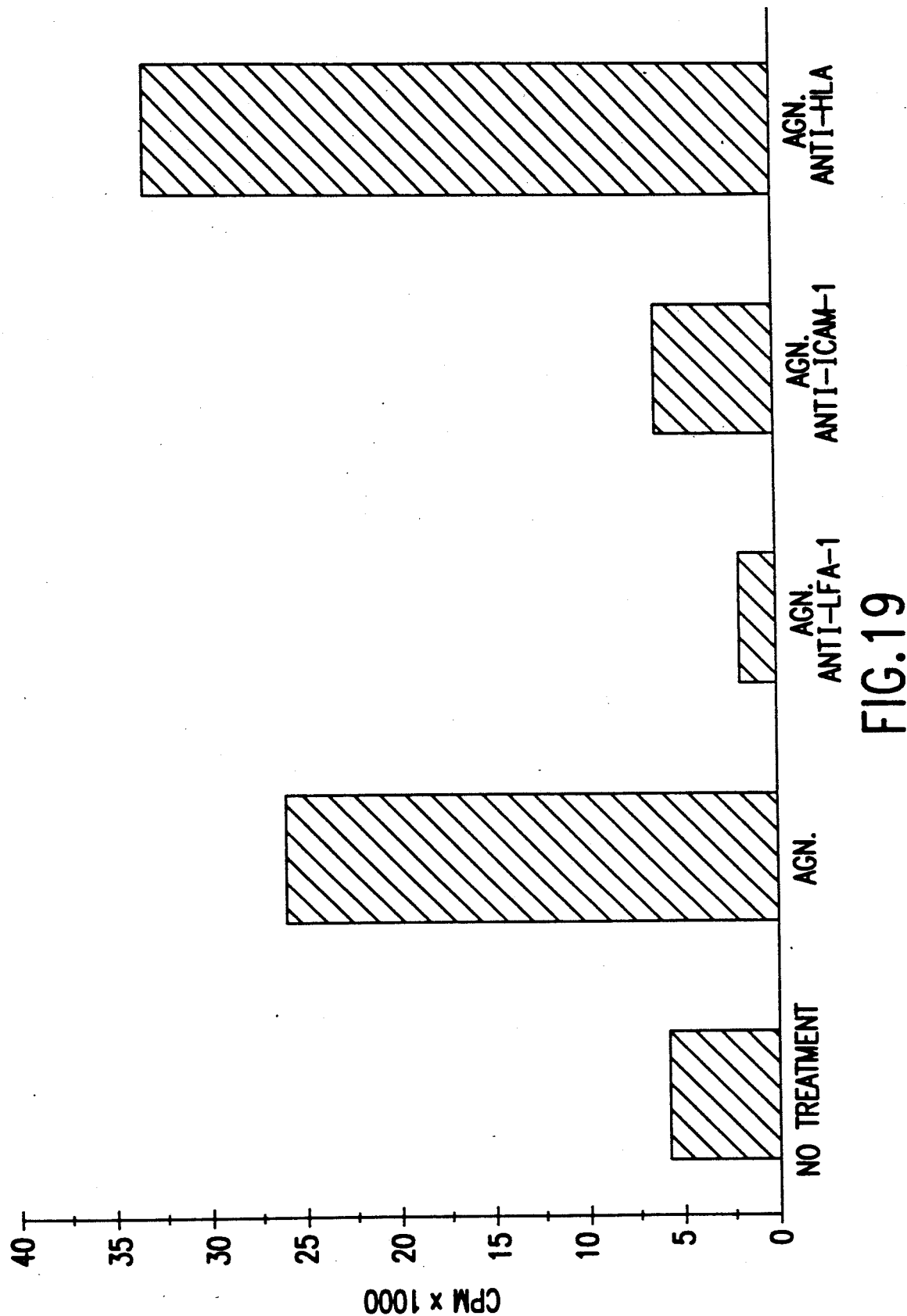
FIG. 19 shows the effect of anti-adhesion antibodies on the ability of peripheral blood mononuclear cells to proliferate in response to the recognition of the tetanus toxoid antigen. The addition of tetanus toxoid antigen to the cells is indicated by "AGN."

Eighteen hours prior to the termination of the assay, 2.5 μCi of $^3$H-thymidine was added to the cultures. Cellular proliferation was assayed by measuring the incorporation of thymidine into DNA by the peripheral blood mononuclear cells. Incorporated thymidine was collected and counted in a liquid scintillation counter (Merluzzi et al., *J. Immunol.* 139:166–168 (1987)). The results of these experiments are shown in FIG. 16 (concanavalin A experiment), FIG. 17 (OKT3 experiment), FIG. 18 (keyhole limpet hemocyanin experiment), and FIG. 19 (tetanus toxoid experiment).

It was found that anti-ICAM-1 antibody inhibits proliferative responses to the non-specific T-cell mitogen, ConA; the non-specific T-cell associated antigen, OKT-3; and the specific antigens, keyhole limpet hemocyanin and tetanus toxoid, in mononuclear cells. The inhibition by anti-ICAM-1 antibody was comparable to that of anti-LFA-1 antibody suggesting that ICAM-1 is a functional ligand of LFA-1 and that antagonism of ICAM-1 will inhibit specific defense system responses.

EXAMPLE 27

Effect of Anti-ICAM-1 Antibody on the Mixed Lymphocyte Reaction

As discussed above, ICAM-1 is necessary for effective cellular interactions during an immune response mediated through LFA-1-dependent cell adhesion. The induction of ICAM-1 during immune responses or inflammatory disease allows for the interaction of leukocytes with each other and with endothelial cells.

When lymphocytes from two unrelated individuals are cultured in each others presence, blast transformation and cell proliferation of the lymphocytes are observed. This response, of one population of lymphocytes to the presence of a second population of lymphocytes, is known as a mixed lymphocyte reaction (MLR), and is analogous to the response of lymphocytes to the addition of mitogens (*Immunology The Science of Self-Nonself Discrimination*, Klein, J., John Wiley & Sons, N.Y. (1982), pp 453–458).

Experiments were performed to determine the effect of anti-ICAM monoclonal antibodies on the human MLR. These experiments were conducted as follows. Peripheral blood was obtained from normal, healthy donors by venipuncture. The blood was collected in heparinized tubes and diluted 1:1 at room temperature with Puck's G (GIBCO) balanced salt solution (BSS). The blood mixture (20 ml) was layered over 15 ml of a Ficoll/Hypaque density gradient (Pharmacia, density = 1.078, room temperature) and centrifuged at 1000 ×g for 20 minutes. The interface was then collected and washed 3× in Puck's G. The cells were counted on a hemacytometer and resuspended in RPMI-1640 culture medium (GIBCO) containing 0.5% of gentamicin, 1 mM L-glutamine (GIBCO) and 5% heat inactivated (56° C., 30 min.) human AB sera (Flow Laboratories) (hereafter referred to as RPMI-culture medium).

Mouse anti-ICAM-1 (R6-5-D6) was used in these experiments. All monoclonal antibodies (prepared from ascites by Jackson ImmunoResearch Laboratories, Boston, Mass.) were used as purified IgG preparations.

Peripheral blood mononuclear cells (PBMC) were cultured in medium at $6.25 \times 10^5$ cells/ml in Linbro round-bottomed microliter plates (#76-013-05). Stimulator cells from a separate donor were irradiated at 1000 R and cultured with the responder cells at the same concentration. The total volume per culture was 0.2 ml. Controls included responder cells alone as well as stimulator cells alone. The culture plates were incubated at 37° C. in a 5% $CO_2$-humidified air atmosphere for 5 days. The wells were pulsed with 0.5 μCi of tritiated thymidine ($^3$HT) (New England Nuclear) for the last 18 hours of culture. In some cases a two-way MLR was performed. The protocol was the same except that the second donor's cells were not inactivated by irradiation.

The cells were harvested onto glass fiber filters using an automated multiple sample harvester (Skatron, Norway), rinsing with water and methanol. The filters were oven dried and counted in Aquasol in a Beckman (LS-3801) liquid scintillation counter. Results are reported as the Mean CPM± standard error of 6 individual cultures.

Table 16 shows that purified anti-ICAM-1 monoclonal antibodies inhibited the MLR in a dose dependent manner with significant suppression apparent at 20 ng/ml. Purified mouse IgG had little or no suppressive effect. Suppression of the MLR by the anti-ICAM-1 monoclonal antibody occurs when the antibody is added within the first 24 hours of cultures (Table 16).

TABLE 16

Effect of Anti-ICAM-1 Antibody on the One-Way Lymphocyte Reaction

| Responder Cells[a] | Stimulator Cells[b] | Antibody[c] | $^3$HT Incorporation (CPM) |
|---|---|---|---|
| − | − | − | 445[d] ± 143 |
| − | + | − | 148 ± 17 |
| + | − | − | 698 ± 72 |
| + | + | − | 42,626 ± 1,579 |
| + | + | mIgG (10.0 μg) | 36,882 ± 1,823 (14%) |
| + | + | mIgG (0.4 μg) | 35,500 ± 1,383 (17%) |
| + | + | mIgG (0.02 μg) | 42,815 ± 1.246 (0%) |

TABLE 16-continued

Effect of Anti-ICAM-1 Antibody on the One-Way Lymphocyte Reaction

| Responder Cells[a] | Stimulator Cells[b] | Antibody[c] | 3HT Incorporation (CPM) |
|---|---|---|---|
| + | + | R6-5-D6 (10.0 μg) | 8,250 ± 520 (81%) |
| + | + | R6-5-D6 (0.4 μg) | 16,142 ± 858 (62%) |
| + | + | R6-5-D6 (0.03 μg) | 28,844 ± 1,780 (32%) |

[a]Responder cells (6.25 × 10$^5$/ml)
[b]Stimulator Cells (6.25 × 10$^5$/ml, irradiated at 1000R)
[c]Purified Monoclonal Antibody to ICAM-1 (R6-5-D6) or purified mouse IgG (mIgG) at final concentration (ug/ml).
[d]Mean ± S.E. of 5-6 cultures, numbers in parentheses indicate percent inhibition of MLR

TABLE 17

Time of Addition of Anti-ICAM-1

3HT Incorporation (CPM)
Time of Addition of Medium or Antibody

| R[a] | S[b] | Additions[c] | Day 0 | Day 1 | Day 2 |
|---|---|---|---|---|---|
| − | − | medium | 205[d] ± 14 | 476 ± 132 | 247 ± 75 |
| − | + | medium | 189 ± 16 | nd[e] | nd |
| + | − | medium | 1,760 ± 615 | nd | nd |
| + | + | medium | 41,063 ± 2,940 | 45,955 ± 2,947 | 50,943 ± 3,072 |
| + | + | R-6-5-D6 | 17,781 ± 1,293 (57%)[f] | 38,409 ± 1,681 (16%) | 47,308 ± 2,089 (7%) |

[a]Responder cells (6.25 × 10$^5$/ml)
[b]Stimulator Cells (6.25 × 10$^5$/ml, irradiated at 1000R)
[c]Culture Medium or Purified Monoclonal Antibody to ICAM-1 (R6-5-D6) at 10 μg/ml were added on day 0 at 24 hour intervals
[d]Mean ± S.E. of 4-6 cultures
[e]nd = not done
[f]Percent Inhibition In summary, the ability of antibody against ICAM-1 to inhibit the MLR shows that ICAM-1 monoclonal antibodies have therapeutic utility in acute graft rejection. ICAM-1 monoclonal antibodies also have therapeutic utility in related immune mediated disorders dependent on LFA-1/ICAM-1 regulated cell to cell interactions.

The experiments described here show that the addition of monoclonal antibodies to ICAM-1 inhibit the mixed lymphocyte reaction (MLR) when added during the first 24 hours of the reaction. Furthermore, ICAM-1 becomes upregulated on human peripheral blood monocytes during in vitro culture.

Furthermore, it was found that ICAM-1 is not expressed on resting human peripheral blood lymphocytes or monocytes. ICAM-1 is up regulated on the monocytes of cultured cells alone or cells co-cultured with unrelated donor cells in a mixed lymphocyte reaction using conventional flow cytometric analyses. This up regulation of ICAM-1 on monocytes can be used as an indicator of inflammation, particularly if ICAM-1 is expressed on fresh monocytes of individuals with acute or chronic inflammation.

ICAM-1's specificity for activated monocytes and the ability of antibody against ICAM-1 to inhibit an MLR suggest that ICAM-1 monoclonal antibodies may have diagnostic and therapeutic potential in acute graft rejection and related immune mediated disorders requiring cell to cell interactions.

EXAMPLE 28

Synergistic Effects of the Combined Administration of Anti-ICAM-1 and Anti-LFA-1 Antibodies As shown in Example 27, the MLR is inhibited by anti-ICAM-1 antibody. The MLR can also be inhibited by the anti-LFA-1 antibody. In order to determine whether the combined administration of anti-ICAM-1 and anti-LFA-1 antibodies would have an enhanced, or synergistic effect, an MLR assay (performed as described in Example 27) was conducted in the presence of various concentrations of the two antibodies.

This MLR assay revealed that the combination of anti-ICAM-1 and anti-LFA-1, at concentrations where neither antibody alone dramatically inhibits the MLR, is significantly more potent in inhibiting the MLR response (Table 18). This result indicates that therapies which additionally involve the administration of anti-ICAM-1 antibody (or fragments thereof) and anti-LFA-1 antibody (of fragments thereof) have the capacity to provide an improved anti-inflammatory therapy. Such an improved therapy permits the administration of lower doses of antibody than would otherwise be therapeutically effective, and has importance in circumstances where high concentrations of individual antibodies induce an anti-idiotypic response.

TABLE 18

Effect of Various Doses of Anti-ICAM-1 and (R3.1) Anti-LFA-1 on Mixed Lymphocyte Reaction

| Concentration (ug/ml) | % Inhibition Anti-ICAM-1 (R6-5-D6) | | | | | |
|---|---|---|---|---|---|---|
| Anti-LFA-1 | 0 | .004 | .02 | .1 | .5 | 2.5 |
| 0.0 | 0 | 7 | 31 | 54 | 69 | 70 |
| 0.0008 | 1 | 7 | 28 | 48 | 62 | 71 |
| 0.004 | 0 | 13 | 30 | 50 | 64 | 72 |
| 0.02 | 29 | 38 | 64 | 75 | 84 | 86 |
| 0.1 | 92.5 | 90 | 91 | 92 | 92 | 92 |
| 0.5 | 93 | 90 | 90 | 92 | 93 | 91 |

EXAMPLE 29

Additive Effects of Combined Administration of Sub-optimal Doses Anti-ICAM-1 and Other Immunosuppressive Agents in the MLR As shown in Example 28, the MLR is inhibited by combinations of anti-ICAM-1 and anti-LFA-1 antibodies. In order to determine whether the combined administration of anti-ICAM-1 and other immunosuppressive agents (such as dexamethasone, azathioprine, cyclosporin A or steroids (such as, for example, preunisone, etc.) would also have enhanced effects, MLR assays were performed using sub-optimal concentrations (i.e concentrations which would be lower than the optimal concentration at which the agent alone would be provided to a subject) of R6-5-D6 in conjunction with other immunosuppressive agents as per the protocol in Example 27.

The data indicate that the inhibitory effects of R6-5-D6 are at least additive with the inhibitory effects of suboptimal doses of dexamethasone (Table 19), Azathioprine (Table 20) and cyclosporin A (Table 21). This implies that anti-ICAM-1 antibodies can be effective in lowering the necessary doses of known immunosuppressants, thus reducing their toxic side effects. In using an anti-ICAM-1 antibody (or a fragment thereof) to achieve such immunosuppression, it is possible to combine the administration of the antibody (or fragment thereof) with either a single additional immunosuppressive agent, or with a combination of more than one additional immunosuppressive agent.

TABLE 19

Effect of Anti-ICAM-1 and Dexamethasone on the Human MLR

| Group | Inhibitor (ng/ml) | $^3$HT Incorporation (CPM) | % Inhibition |
| --- | --- | --- | --- |
| Media | — | 156 | — |
| Stimulators (S) | — | 101 | — |
| Responders (R) | — | 4,461 | — |
| R × S | — | 34,199 | — |
| R × S | R6-5-D6 (8) | 26,224 | 23 |
| R × S | Dex (50) | 14,148 | 59 |
| R × S | R6-5-D6 (8) + Dex (50) | 7,759 | 77 |

Dex: Dexamethasone

TABLE 20

Effect of Anti-ICAM-1 and Azathioprine on the Human MLR

| Group | Inhibitor (ng/ml) | $^3$HT Incorporation (CPM) | % Inhibition |
| --- | --- | --- | --- |
| Media | — | 78 | — |
| Stimulators (S) | — | 174 | — |
| Responders (R) | — | 3,419 | — |
| R × S | — | 49,570 | — |
| R × S | R6-5-D6 (8) | 44,374 | 11 |
| R × S | Azathioprine (1) | 42,710 | 14 |
| R × S | R6-5-D6 (8) + Azathioprine (1) | 34,246 | 31 |

TABLE 21

Effect of Anti-ICAM-1 and Cyclosporin A on the Human MLR

| Group | Inhibitor (ng/ml) | $^3$HT Incorporation (CPM) | % Inhibition |
| --- | --- | --- | --- |
| Media | — | 87 | — |
| Stimulators (S) | — | 206 | — |
| Responders (R) | — | 987 | — |
| R × S | — | 31,640 | — |
| R × S | R6-5-D6 (8) | 26,282 | 17 |
| R × S | CyA (10) | 23,617 | 25 |
| R × S | R6-5-D6 (8) + CyA (10) | 19,204 | 39 |

CyA: Cyclosporin A

EXAMPLE 30

Effect of Anti-ICAM-1 Antibody in Suppressing the Rejection of Transplanted Allogeneic Organs In order to demonstrate the effect of anti-ICAM-1 antibody in suppressing the rejection of an allogeneic transplanted organ, Cynomolgus monkeys were transplanted with allogeneic kidneys according to the method described by Cosimi et al. (*Transplant. Proc.* 13:499-503 (1981)) with the modification that valium and ketamine were used as anesthesia.

Thus, the kidney transplantation was performed essentially as follows. Heterotropic renal allografts were performed in 3-5 kg Cynomolgus monkeys, essentially as described by Marquet (Marquet et al., *Medical Primatology*, Part II, Basel, Karger, p. 125 (1972)) after induction of anesthesia with valium and ketamine. End-to-side anastomoses of donor renal vessels on a patch of aorta or vena cava were constructed using 7-0 Prolene suture. The donor ureter was spatulated and implanted into the bladder by the extravesical approach (Taguchi, Y., al., in Dausset et al. (eds.), in: *Advances in Transplantation*, Baltimore, Williams & Wilkins, p. 393 (1968)). Renal function was evaluated by weekly or biweekly serum creatinine determinations. In addition, frequent allograft biopsies were obtained for histopathologic examination and complete autopsies were performed on all nonsurviving recipients. In most recipients, bilateral nephrectomy was performed at the time of transplantation and subsequent uremic death was considered the end point of allograft survival. In some recipients, unilateral native nephrectomy and contralateral ureteral ligation were performed at the time of transplantation. When allograft rejection occurred, the ligature on the autologous ureter was then removed resulting in restoration of normal renal function and the opportunity to continue immunologic monitoring of the recipient animal.

Monoclonal antibody R6-5-D6 was administered daily for 12 days starting two days prior to transplant at a dose of 1-2 mg/kg/day. Serum levels of creatinine were periodically tested to monitor rejection. The effect of anti-ICAM-1 antibody on the immune system's rejection of the allogeneic kidneys is shown in Table 22.

TABLE 22

R6-5-D6 Activity in Prolonging Renal Allograft Survival in Prophylactic Protocols in the Cynomolgus Monkey[a]

| Monkey | Dose of R6-5-D6 (mg/kg) | Days of Survival/Post-Treatment |
| --- | --- | --- |
| Control 1 | — | 8 |
| Control 2 | — | 11 |
| Control 3 | — | 11 |
| Control 4 | — | 10 |
| Control 5 | — | 9 |
| Control 6 | — | 10 |
| M15 | 1.0 | 20 |
| M19 | 1.0 | 7[b] |
| M17 | 1.0 | 30 |
| M25 | 1.5 | 29 |
| M23 | 1.0 | 11[c] |
| M27 | 2.0 | 34 |
| M7 | 0.5 | 22 |
| M11 | 0.5 | 26 |
| M10 | 0.5 | 22 |
| M8 | 0.5 | 26[d] |

[a]Monkeys were given R6-5-D6 for 12 consecutive days starting at 2 days prior to transplantation.
[b]Cause of death is unknown. There was evidence of latent malaria.
[c]Died of kidney infarct.
[d]Still living as of August 15, 1988.

The results show that R6-5-D6 was effective in prolonging the lives of monkeys receiving allogneic kidney transplants.

EXAMPLE 31

Effect of Anti-ICAM-1 Antibody in Suppressing Acute Rejection of Transplanted Organs In order to show that anti-ICAM-1 antibody is effective in an acute model of transplant rejection, R6-5-D6 was also tested in a therapeutic or acute kidney rejection model. In this model, monkey kidneys were transplanted (using the protocol described in Example 30) and given perioperatively 15 mg/kg cyclosporin A (CyA) i.m. until stable renal function was achieved. The dose of CYA was then reduced biweekly in 2.5 mg/kg increments until rejection occurred as indicated by a rise in blood creatinine levels. At this point, R6-5-D6 was administered for 10 days and the length of survival was monitored. It is important to note that in this protocol, the dose of CyA remains suboptimal since it does not change once the acute rejection episode occurs. In this model historical controls (N=5) with no antibody rescue survive 5-14 days from the onset of the rejection episode. To date, six animals were tested using R6-5-D6 in this protocol (Table 23). Two of these animals are still surviving (M12, 31 days and M5, 47 days following the administration of R6-5-D6). Two animals lived 38 and 55 days following initiations of R6-5-D6 therapy and two animals died from causes other than acute rejection (one animal died of CyA toxicity and the other died while being given R6-5-D6 under anesthesia). This model more closely approximates the clinical situation in which R6-5-D6 would be initially used.

TABLE 23

R6-5-D6 Activity in Prolonging Renal Allograft Survival in Therapeutic Protocols in the Cynomolgus Monkey[a]

| Monkey | Day of Rejection Episode[b] | Days of Survival/ Post-Treatment |
|---|---|---|
| Controls[c] | 14-98 | 5-14 |
| M24 | 41 | 38 |
| M21 | 34 | 4[d] |
| M3 | 41 | 55 |
| M9 | 12 | 11[e] |
| M12 | 37 | >31[f] |
| M5 | 26 | >47[f] |

[a]Monkeys were given 1-2 mg/kg of R6-5-D6 for 10 consecutive days following onset of rejection.
[b]Day at which creatinine levels increased as a result of reduction of CyA dosage and R6-5-D6 therapy started.
[c]Five animals were tested using the therapeutic protocol described above except that there was no rescue therapy. Days of survival/post treatment represents days of survival once creatinine levels started to rise.
[d]Died while under anesthesia. Creatinine levels were low.
[e]Died of CyA toxicity. Creatinine levels were low.
[f]Still living as of August 15, 1988.

EXAMPLE 32

Genetic Construction and Expression of Truncated Derivatives of ICAM-1

In its natural state, ICAM-1 is a cell membrane-bound protein containing an extracellular region of 5 immunoglobuline-like domains, a transmembrane domain, and a cytoplasmic domain. It was desirable to construct functional derivatives of ICAM-1 lacking the transmembrane domain and/or the cytoplasmic domain in that a soluble, secreted form of ICAM-1 could be generated. These functional derivatives were constructed by oligonucleotide-directed mutagenesis of the ICAM-1 gene, followed by expression in monkey cells after transfection with the mutant gene.

Mutations in the ICAM-1 gene resulting in amino acid substitutions and/or, truncated derivatives were generated by the method of Kunkel, T., (Proc. Natl. Acad. Sci. (U.S.A.) 82:488-492 (1985)). ICAM-1 cDNA prepared as described above was digested with restriction endonucleases Sal 1 and Kpn 1, and the resulting 1.8 kb DNA fragment was subcloned into the plasmid vector CDM8 (Seed, B. et al., Proc. Natl. Acad. Sci. (U.S.A.) 84:3365-3369 (1987)). A dut−, ung− strain of E. coli (BW313/P3) was then transformed with this construct, designated pCD1.8C. A single-strand uracil-containing template was rescued from the transformants by infection with the helper phage R408 (Stratagene ®). Mutant ICAM-1 cDNAs were then generated by priming a second strand synthesis with an oligonucleotide possessing mismatched bases, and subsequent transformation of a ung+ host (MC1061/P3) with the resulting heteroduplex. Mutants were isolated by screening for newly created endonuclease restriction sites introduced by the mutant oligonucleotide. The mutant ICAM-1 protein was expressed by transfection of Cos-7 cells with the mutant DNA in the eukaryotic expression vector CDM8 using standard DEAE-Dextran procedures (Selden, R. F. et al., In: Current Protocols in Molecular Biology (Ausubel, F. M. et al., eds.) pages 9.2.1-9.2.6 (1987)).

A truncated functional derivative of ICAM-1 lacking the transmembrane and cytoplasmic domains, but containing the extracellular region possessing all 5 immunoglobulin-like domains was prepared. A 30 bp mutant oligonucleotide (CTC TCC CCC CGG TTC TAG ATT GTC ATC ATC) was used to transform the codons for amino acids tyrosine (Y) and glutamic acid (E) at positions 452 and 453, respectively, to a phenylalanine (F) and a translational stop codon (TAG). The mutant was isolated by its unique Xba 1 restriction site, and was designated $Y^{452}E/F,TAG$.

To express the mutant protein, COS cells were transfected with three mutuant subclones (#2, #7, and #8). Three days after transfection with the three mutant subclones, culture supernates and cell lysate were analysed by immunoprecipitation with anti-ICAM-1 monoclonal antibody RR1/1 and SDS-PAGE. ICAM-1 was precipitated from the culture (j supernates of cells transfected with mutant subclones #2 and #8, but not from detergent lysates of those cells. The molecular weight of ICAM-1 found in the culture supernate was reduced approximately 6 kd relative to the membrane form of ICAM-1, which is consistent with the size predicted from the mutant DNA. Thus, this functional derivative of ICAM-1 is excreted as a soluble protein. In contrast, ICAM-1 was not immunoprecipitated from control culture supernates of cells transfected with native ICAM-1, demonstrating that the membrane form of ICAM-1 is not shed from Cos cells. Futhermore, no ICAM-1 was immunoprecipitated from either culture supernates or cell lysates from negative control mock-transfected cells.

The truncated ICAM-1 secreted from transfected cells was purified by immunoaffinity chromatography with an ICAM-1 specific antibody (R6-5-D6) and tested for functional activity in a cell binding assay. After purification in the presence of the detergent octylglucoside, preparations containing native ICAM-1 or the truncated, secreted form were diluted to a final concentration of 0.25% octylglucoside (a concentration below the critical micelle concentration of the detergent). These preparations of ICAM-1 were allowed to bind to the surfaces of plastic 96-well plates (Nunc), to produce ICAM-1 bound to a solid-phase. After washing out unbound material, approximately 75-80% and 83-88% of SKW-3 cells bearing LFA-1 on their surface bound specifically to the native and to the truncated forms of ICAM-1, respectively. These data demonstrate that the secreted, truncated soluble ICAM-1 functional derivative retained both the immunological reactivity and the ability to mediate ICAM-1 dependent adhesion which are characteristic of native ICAM-1.

A functional derivative of ICAM-1 lacking only the cytoplasmic domain was prepared by similar methods. A 25 bp oligonucleotide (TC AGC ACG TAC CTC TAG AAC CGC CA) was used to alter the codon for amino acid 476 (Y) to a TAG translational stop codon. The mutant was designated Y$^{476}$/TAG. Immunoprecipitation analysis and SDS-PAGE Of Cos cells transfected with the mutant detected a membrane bound form of ICAM-1 with a molecular weight approximately 3 kd less than native ICAM-1. Indirect immunofluorescence of the mutant-transfected Cos cells demonstrated a punctate staining pattern similar to naive ICAM-1 expressed on LPS-stimulated human endothelial cells. Finally, cells transfected with the mutant DNA specifically bound to purified LFA-1 on plastic surfaces in a manner similar to Cos cells transfected with native ICAM-1 DNA (Table 24).

TABLE 24

Ability of Cells Expressing ICAM-1 or a Functional Derivative of ICAM-1 to Bind LFA-1

| TRANSFECTION | % of Cells Expressing ICAM-1 that Bind LFA-1 in the Presence of: | |
| --- | --- | --- |
|  | No Antibody | RR1/1 |
| Mock | 0 | 0 |
| Native ICAM-1 | 20 | 0 |
| Y$^{476}$/TAG | 20 | 0 |

EXAMPLE 33

Mapping of ICAM-1 Functional Domains

Studies of ICAM-1 have revealed that the molecule possesses 7 domains. Five of these domains are extracellular (domain 5 being closest to the cell surface, domain I being furthest from the cell surface), one domain is a transmembrane domain, and one domain is cytoplasmic (i.e. lies within the cell). In order to determine which domains contribute to the ability of ICAM-1 to bind LFA-1, epitope mapping studies may be used. To conduct such studies, different deletion mutants are prepared and characterized for their capacity to bind to LFA-1. Alternatively, the studies may be accomplished using anti-ICAM antibody known to interfere with the capacity of ICAM-1 to bind LFA-1. Examples of such suitable antibody include RR1/1 (Rothlein, R. et al., *J. Immunol.* 137:1270-1274 (1986)), R6.5 (Springer, T. A. et al., U.S. patent application Ser. No. 07/250,446), LB-2 (Clark, E. A. et al., In: *Leukocyte Typing I* (A. Bernard, et al., Eds.), Springer-Verlag pp 339-346 (1984)), or CL203 (Staunton, D. E. et al., *Cell* 56:849-853 (1989)).

Deletion mutants of ICAM-1 can be created by any of a variety of means. It is, however, preferable to produce such mutants via site directed mutagenesis, or by other recombinant means (such as by constructing ICAM-1 expressing gene sequences in which sequences that encode particular protein regions have been deleted. Procedures which may be adapted to produce such mutants are well known in the art. Using such procedures, three ICAM-1 deletion mutants were prepared. The first mutant lacks amino acid residues F185 through P284 (i.e. deletion of domain 3). The second mutant lacks amino acid residues P284 through R451 (i.e. deletion of domains 4 and 5). The third mutant lacks amino acid residues after Y476 (i.e. deletion of cytoplasmic domain). The results of such studies indicate that domains 1, 2, and 3 are predominantly involved in ICAM-1 interactions with anti-ICAM-1 antibody and LFA-1.

EXAMPLE 34

Effect of Mutations In ICAM-1 On LFA-1 Binding

The ability of ICAM-1 to interact with and bind to LFA-1 is mediated by ICAM-1 amino acid residues which are present in domains 1 of the ICAM-1 molecule (FIGS. 8, 9 and 10). Such interactions are assisted, however, by contributions from amino acids present in domains 2 and 3 of ICAM-1. Thus, among the preferred functional derivatives of the present invention are soluble fragments of the ICAM-1 molecule which contain domains 1, 2, and 3 of ICAM-1. More preferred are soluble fragments of the ICAM-1 molecule which contain domains 1 and 2 of ICAM-1. Most preferred are soluble fragments of the ICAM-1 molecule which contain domain 1 of ICAM-1. Several amino acid residues within the first ICAM-1 domain are involved in the interaction of ICAM-1 and LFA-1. Substitutions of these amino acids with other amino acids alter the ability of ICAM-1 to bind LFA-1. These amino acid residues and the substitutions are shown in Table 25. Table 25 shows the effects of such mutations on the ability of the resulting mutant ICAM-1 molecule to bind to LFA-1. In Table 25, residues are described with reference to the one letter code for amino acids, followed by the position of the residue in the ICAM-1 molecule. Thus, for example, "E90" refers to the glutamic acid residue at position 90 of ICAM-1. Similarly, "E90V" refers to the dipeptide composed of the glutamic acid residue at position 90 and the valine residue at position 91. The substitution sequence is indicated to the right of the slash ("/") mark. The S3VS, V4, R13, D26QPK, Q27, E34, G46NN, K50V, Q58EDS, D60, D71GQS, Q73, Y83, E90, N103, A115N, and N175TSA residues of ICAM-1, for example, are involved in LFA-1 binding (Table 25).

Replacement of these amino acids altered the capacity of ICAM-1 to bind to LFA-1. For example, replacement of V4 with G results in the formation of a mutant ICAM-1 molecule which is less able to bind to LFA-1 (Table 25). Replacement of the R13 residue of ICAM-1 with E, or of the E34 residue with A, leads to the formation of a mutant molecule with substantially less capacity to bind LFA-1. (Table 25). Replacement of the D60S residues of ICAM-1 with KL leads to the formation of a mutant molecule having substantially less capacity to bind LFA-1 (Table 25). In contrast, replacement of the Q58 residue of ICAM-1 with H leads to the formation of a mutant molecule having a substantially normal capacity to bind LFA-1 (Table 25).

Glycosylation sites in the second domain are also involved in LFA-1 binding (Table 25). Replacement of N103 with K, or A115N with SV, results in the formation of a mutant ICAM-1 molecule which is substantially incapable of binding LFA-1. In contrast, replacement of the glycosylation site N175 with A did not appear to substantially effect the capacity of the mutant ICAM-1 to bind LFA-1.

Mutations in the third ICAM-1 domain did not appreciably alter ICAM-1 LFA-1 binding (Table 25).

EXAMPLE 35

Multimeric Forms of ICAM-1 With Increased Biological Half-Life, Affinity And Clearance Ability Chimeric molecules are constructed in which domains 1 and 2 of ICAM-1 are attached to the hinge region of the immunoglobulin heavy chain. Preferred constructs attach the C-terminus of ICAM-1 domain 2 to a segment of the immunoglobulin heavy chain gene just N-terminal to the hinge region, allowing the segmental flexibility conferred by the hinge region. The ICAM-1 domains 1 and 2 will thus replace the Fab fragment of an antibody. Attachment to heavy chains of the IgG class and expression in animal cells will result in the production of a chimeric molecule. Production of molecules containing heavy chains derived from IgA or IgM will result in expression of molecules containing from 2 to 12 ICAM-1 molecules. A chimeric immunoglobulin having an IgG heavy chain will contain 1-2 ICAM-1 molecules. Co-expression of J-chain gene in the animal cells producing the ICAM-1 heavy chain chimeric molecules will allow proper assembly of IgA and IgM multimers resulting predominantly in IgA molecules containing 4 to 6 ICAM-1 molecules and in the case of IgM containing approximately 10 ICAM-1 molecules.

These chimeric molecules may have several advantages. First, Ig molecules are designed to be long lasting in the circulation and this may improve biological half-life. Furthermore, the multimeric nature of these engineered molecules will allow them to interact with higher avidity with rhinovirus as well as with cell surface LFA-1, depending on the therapeutic context, and thus greatly decrease the amount of recombinant protein which needs to be administered to give an effective dose. IgA and IgM are highly glycosylated molecules normally present in secretions at mucosal sites as in the nose. Their highly hydrophilic nature helps to keep bacteria and viruses to which they bind out in the mucosa, preventing attachment to cells and preventing crossing of the epithelial cell membrane barrier. Thus, they may have increased therapeutic efficacy. IgM and in particularly IgA are stable in mucosal environments and they may increase the stability of the ICAM-1 constructs. If such an ICAM-1 functional derivative is administered in the blood stream, it may also increase biological half-life. IgA does not fix complement and thus would be ideal for applications in which this would be deleterious. If IgG H chain chimerics are desired, it would be possible to mutate regions involved in attachment to complement as well as in interactions with Fc receptors.

EXAMPLE 36

ICAM-1 Outline Structure And The LFA-1 And Rhinovirus Binding Sites: Viral Mimicry of a Cell Adhesion Receptor ICAM-1 and a second LFA-1 counter-receptor, ICAM-2, constitute a subfamily of the immunoglobulin (Ig) superfamily (Staunton, D. E., et al., Cell 52:925-933 (1988), which reference is incorporated herein by reference). ICAM-1 possesses five Ig-like C domains whereas ICAM-2 possesses two, which are most homologous to the amino terminal domains of ICAM-1. ICAM-1 and ICAM-2, expressed on a variety of cell types, support various leukocyte adhesion dependent functions including induction and effector functions in the immune response. ICAM-1 expression is highly inducible by cytokines and thus the LFA-1/ICAM-1 adhesion system is able to guide leukocyte migration and localization during inflammation (Rothlein, R. J. Immunol. 137:1270-1274 (1986); Marlin, S. D. et al., Cell 51:813-819 (1987); Kishimoto, T. K. et al., Adv. Immunol. 46:149-182 (1989); Dustin, M. L. et al., Immunol. Today 2:213-215 (1988), all of which references are incorporated herein by reference).

LFA-1 (CD11a/CD18) is a member of the integrin family most closely related to two other leukocyte integrins Mac-1 (CR3; CD11b/CD18) and p150/95 (CD11c/CD18) (Hynes, R. O., Cell 48:549,554 (1987)) Mac-1, in addition to supporting neutrophil adhesion, has been demonstrated to bind several ligands including iC3b, leishmania gp63 and fibrinogen (Ruoslahti, E., et al., Cell 44:517-518 (1986); Hynes, R. O., Cell 48:549-554 (1987)) Binding to these ligands can be competed with peptides containing either an RGD or KXXDS sequence (Marlin, S. D. et al., Cell 51:813-819 (1987)). Neither ICAM possesses an RGD or KXXDS sequence. It i; therefore consistent that interaction between ICAM-1 and LFA-1 is not competed with RGD peptides. Thus, the site of contact on ICAM-1 with LFA-1 is not apparent by analogy to many other integrin-ligand interactions.

ICAM-1 has recently been shown to be subverted as a receptor by the major group of rhinoviruses (Greve, J. M. et al., Cell 56:839-847 (1989); Staunton, D. E. et al., Cell 56:849-853 (1989); Tomassini, J. E. et al. Proc. Natl. Acad. Sci. (U.S.A.) 86:4907-4911 (1989), which references are incorporated herein by reference). Rhinoviruses, members of the small, RNA-containing, protein-encapsidated picornavirus family, cause 40-50% of common colds (Rueckert, R. R., In: Fields Virology Fields, B. N. et al. (eds.), Raven Press, N.Y., (1985) pp 705-738; Sperber, S.J. et al. Antimicr. Agents Chemo. 32: 409-419 (1988), which references are incorporated herein by reference). Over 100 immunologically non-crossreactive rhinoviruses have been defined, of which 90% bind to ICAM-1.

X-ray crystallography shows that rhinoviruses are 30 nm in diameter and have icosahedral symetry with 60 copies of each capsid protein (Rossmann, M. G. Nature 317:145-153 (1985)) and hence have 60 potential binding sites for ICAM-1. Based on amino acid substitution mutants, and conformational changes induced by the binding of anti-viral drugs, a deep region of depression or canyon in the capsid which runs about its 5-fold axes has been identified (Rossmann, M. G. Et al., Nature 317:145-153 (1985); Colonno, R. J. et al., Proc. Natl. Acad. Sci. (U.S.A.) 85:5449-5453 (1988); Rossmann, M. G. et al., Ann. Rev. Biochem. 58:533-573 (1989)). Residues at the floor of the canyon are implicated in ICAM-1 binding function.

A single ICAM-1 Ig-like domain is predicted to be of approximately the correct dimensions to associate with HRV residues at the canyon floor (Staunton, D. E. et al. Cell 56:849-853 (1989)); however, an antibody Fab fragment is predicted to be excluded (Rossmann, M. G. et al., Nature 317:145-153 (1985)). Because the antibody combining site of an Fab fragment is too large to come in contact with the canyon floor, receptor specificity may be maintained by relatively conserved residues at the canyon floor while mutations of residues at the canyon rim may allow for new serotypes and evasion of immune surveillance; the "canyon hypothesis" (Rossmann, M. G. et al., Nature 317:145-153 (1985); Colonno, R. J. et al., *Proc. Natl. Acad. Sci. (U.S.A.)* 85:5449–5453 (1988); Rossmann, M. G. et al., *Ann. Rev. Biochem.* 58:533–573 (1989)).

The overall size and shape of ICAM-1 is important to understanding how its Ig domains are arranged. Thus far X-ray crystal structures for Ig superfamily members are available only for immunoglobulins and HLA antigens, which have paired Ig domains; however, domains can also be unpaired as evidenced by Thy-1 which contains a single domain.

Three non-cross blocking ICAM-1 MAbs (RR1/1, R6.5, and LB-2) which block binding to LFA-1 also block HRV binding whereas another (CL203) blocks neither LFA-1 nor HRV binding (Makgoba, M. W., et al., In: *Immunobiology of HLA Volume II: Immunogenetics and Histocompatibility*, B. Dupont, ed., New York: Springer-Verlag, pp. 577–580 (1989); Maio, M., *J. Immunol.* 143:181–188 (1989); Staunton, D. E. et al., *Cell* 56:849–853 (1989), which references are incorporated herein by reference). This finding shows that LFA-1 and HRV may bind to an overlapping region on ICAM-1.

Besides ICAM-1, the cell adhesion molecule CD4 and the complement receptor CR2 have recently been found to be subverted as virus receptors by HIV and EBV viruses, respectively (Maddon, P. J., *Cell* 47:333–348 (1986); Fingeroth, J. D., et al., *Proc. Natl. Acad. Sci. USA* 81:4510–4514 (1984), which references are incorporated herein by reference). Further, a molecule with an Ig domain structure similar to ICAM-1 and which may function in cellular adhesion is a polio virus receptor (Mendelsohn, C. L., it al., *Cell* 56:855–865 (1989)). This may be more than coincidental, since cell adhesion and virus adhesion are in principle very similar. It, therefore, appears that the region of the cell adhesion molecule adopted for binding by the virus is similar to the region adapted for binding to the cell adhesion receptor.

Binding sites for LFA-1 and HRV were determined using site-directed mutagenesis. Regions on ICAM-1 were defined by deleting domains and making amino acid substitutions by site-directed mutagenesis. Characterization of the binding site on ICAM-1 for LFA-1 provides insight into the interaction between Ig and integrin superfamily members.

EXAMPLE 37

Generation of ICAM-1 Mutants

Oligonucleotide-directed mutagenesis

The coding region of an ICAM-1 cDNA in a 1.8 kb Sall-Kpnl fragment, was subcloned into the expression vector CDMB (Seed, B. et al., *Proc.. Natl. Acad. Sci. (U.S.A.)* 84:3365–3369 (1987)). Based on the method of Kunkel, T., (*Proc. Natl. Acad. Sci. (U.S.A.)* 82:488–492 (1985)) and modifications of Staunton D. et al. (Staunton, D. E. et al., *Cell* 52:925–933 (1988)), this construct (pCD1.8) was used to generate a single strand uracil containing template to be used in oligonucleotide-directed mutagenesis.

Briefly, *E. coli* strain XS127 was transformed with pCD1.8. Single colonies were grown in one ml of Luria Broth (LB) medium (Difco) with 13 $\mu g/ml$ ampicillin and 8 $\mu g/ml$ tetracycline until near saturation. 100 $\mu l$ of the culture was infected with R408 helper phage (Strategene) at a multiplicity of infection (MOI) of 10, and 10 ml of LB medium with ampicillin and tetracycline was added for a 16 hr culture at 37° C. Following centrifugation at 10,000 rpm for one minute, and 0.22 $\mu m$ filtration of the supernatant, the phage suspension was used to infect *E. coli* BW313/P3 which was then plated on LB agar (Difco) plates supplemented with ampicillin and tetracycline. Colonies were picked, grown in 1 ml LB medium with ampicillin and tetracycline to near saturation and infected with helper phage at MOI of 10. Culture volume was then increased to 250 ml and the cells cultured overnight. Single strand DNA was isolated by standard phage extraction.

Mutant oligonucleotides were phosphorylated and utilized with the pCD1.8, template in a second strand synthesis reaction (Staunton, D. E. et al., *Cell* 52:925–933 (1988)).

Transfection

COS cells were seeded into 10 cm tissue culture plates such that they would be 50% confluent by 16–24 hrs. COS cells were then washed once with TBS and incubated for 4 hrs with 4 ml RPMI containing 10% Nu sera (Collaborative) 5 $\mu g/ml$ chloroquine, 3 $\mu g$ of mutant plasmid and 200 $\mu g/ml$ DEAE-dextran sulfate. Cells were then washed wit 10% DMSO/PBS followed by PBS and cultured 16 hrs in culture media. Culture media was replaced with fresh media and at 48 hrs post transfection (OS cells were suspended by trypsin/EDTA (Gibco) treatment and divided into 2, 10 cm plates as well as 24 well tissue culture plates for HRV binding. At 72 hrs cells were harvested from 10 cm plates with 5 mM EDTA/HBSS and processed for adhesion to LFA-1 coated plastic and immunofluorescence.

LFA-1 and HRV binding

LFA-1 was purified from SKW-3 lysates by immunoaffinity chromatography on TS2/4 LFA-1 mAb Sepharose and eluted at pH 11.5 in the presence of 2 mM $MgCl_2$ and 1% octylgucoside. LFA-1 (10 $\mu g$ per 200 $\mu l$ per 6-cm plate) was bound to bacteriological Petri dishes by diluting octylglucoside to 0.1% in PBS (phosphate buffered saline) with 2 Mm $MgCl_2$ and overnight incubation at 4° C. Plates were blocked with 1% BSA (bovine serum albumin) and stored in PBS containing 2mM $MgCl_2$, 0.2% BSA, 0.025% azide, and 50 $\mu g/ml$ gentamycin.

$^5Cr$-labelled COS cells in PBS containing 5% FCS (fetal calf serum), 2 mM $MgCl_2$, 0.025% azide (buffer) were incubated with or without 5 $\mu g/ml$ RR1/1 and R6.5 in LFA-1 coated microtiter plates at 25° C. for 1 hour. Non-adherent cells were removed by 3 washed with buffer. Adherent cells were eluted by the addition of EDTA to 10 mM and $\gamma$- counted.

For HRV binding studies, COS cells were reseeded in a 24 well plate. One day later, the confluent monolayer was washed twice with 1 ml of RPMI 1640 / 10 mM $MgCl_2$ / 25 mM Hepes pH 7.3 (rhinovirus-14 buffer). Transfected COS cells were labeled with 51Cr for binding to LFA-1 coated plastic as previously described (Staunton, D. E., et al., *Nature* 339:61–64 (1989). Immunoprecipitation and indirect immunofluorescence was performed using ICAM-1 MAb RR1/1 (Rothlein, R., et al., *J. Immunol.* 137:1270–1274 (1986)), R6.5 (Rothlein, R., et al., *J. Immunol.* 141:1665–1669 (1988)), LB-1 (Clark, E. A., et al., *Hum. Immunol.* 16:100–113 (1986)) and CL203 (Maio, M., *J. Immunol.* 143:181–188 (1989), all of which references are incorporated herein by reference).

[35S]-Met labeled HRV14 (Sherry, B. et al., *J. Virol.* 57:246–257 (1986) which reference is incorporated herein by reference)), 15–25,000 cpm (approximately 107 PFU) in 100 μl of HRV-buffer was added to each well. Binding occurred in 1 hr at 35° C. in a 5% $CO_2$ atmosphere with horizontal rotation (100 rpm). Unbound [35S] HRV14 was aspirated, COS cells were gently washed with 150 ml of HRV buffer and then solubilized with 1% SDS in PBS for scintillation counting.

LFA-1 and HRV-14 binding to ICAM-1 mutants was corrected for binding to mock transfected cells and was normalized for the percent of COS cells staining with CL203 mAb and for percent of binding obtained with wild type:

% binding =

$$\frac{\left(\frac{(\% \text{ mut binding} - \% \text{ mock binding})/}{\% \text{ mut CL203 stain}}\right) \times 100}{(\% \text{ wt binding} - \% \text{ mock binding})/\% \text{ wt CL203 staining}}$$

Binding of RR1, R6.5, and LB-2 mAb was normalized to binding of CL203 mAb using Specific Linear Fluorescence Intensity (SLFI):

% CL203 = (mAb SLFI) × 100) / CL203 mAB SLFI

Percent of wild-type ICAM-1 expressing COS cells that bound to LFA-1 varied from 11–63% (mean=33%); percent of mock-transfected COS cells bindig varied from 0–1%. Percent of [35S] methionine-labeled HRV-14 which bound to COS cells expressing wild-type ICAM-1 varied from 6–43% (mean=21%); percent of mock-transfected COS cell binding varied from 0–4%.

[35S] HRV14 binding to ICAM-1 coated plastic was performed as described by Staunton, D. E. et al., *Cell* 56:849–853 (1989), which reference is incorporated herein by reference) but with modification of the HRV buffer as indicated. Incubation conditions were 35° C., 5% $CO_2$ for 1 hour with rotation.

Anti-ICAM-1 antibodies such as RR1/1 (Rothlein, R. et al., *J. Immunol.* 137:1270–1274 (1986)), R6.5 (Springer, T. A. et al., U.S. patent application Ser. No. 07/250,446), LB-2 (Clark, E. A. et al., In: *Leukocyte Typing I* (A. Bernard, et al., Eds.), Springer-Verlag pp 339–346 (1984)), and CL203 (Staunton, D. E. et al., *Cell* 56:849–853 (1989), all of which references are incorporated herein by reference) have been identified. If these antibodies are capable of inhibiting ICAM-1 function, they must be capable of binding to a particular site in the ICAM-1 molecule which is also important to the ICAM-1 function. Thus, by preparing the above-described deletion mutants of ICAM-1, and determining the extent to which the anti-ICAM-1 antibodies can bind to the deletion, it is possible to determine whether the deleted domains are important for function.

EXAMPLE 38

VISUALIZATION OF ICAM-1 BY ELECTRON MICROSCOPY

The ICAM-1 molecule was examined using electron microscopy. In order to visualize the ICAM-1 molecule for electron microscopy, a soluble fragment of ICAM-1 possessing all five extracellular Ig-like domains (FIG. 4) was purified from the culture media of COS cells transfected with an ICAM-1 mutant construct pCDsD1-5.

ICAM-1 was prepared from COS cells in the following manner. COS cells at 50% confluency were transfected by DEAE-dextran method (Kingston, R. E., In *Current Protocols in Molecular Biology*, Greene Publishing Associates, pp. 9.0.1–9.9.6 (1987)) which reference is incorporated herein by reference) using approximately 0 (mock) or 4 mg of plasmid/10 cm plate.

Secreted ICAM-1 was purified from the supernatants of COS cells transfected with pCDsD1-5 as described by Marlin and Springer (Marlin, S. D. et al., *Cell* 51:813–819 (1987)) with minor modifications as discussed below. Supernatants were harvested between day 4 and 12 post-transfection (200 ng/ml sICAM-1 0.22 μ filtered and passed over RR1/1-sepharose (5 ml, 5 mg/ml) at 0.5 ml/min. The column was washed and eluted with 50 mM triethanolamine HCl, 0.15M NaCl at pH 10 and pH 12.5, respectively, and fractions were neutralized immediately.

Soluble ICAM was dialized into 0.2 M ammonium bicarbonate, 30% glycerol and prepared for electron microscopy by rotary shadowing (Fowler, W. E. et al., *J. Molec. Biol.* 134:241–249 (1979)). Alternatively, the soluble ICAM was sedimented through a 15–40% glycerol gradient, in 0.2 M ammonium bicarbonate, and the ICAM fractions were used directly for rotary shadowing. The sedimentation coefficient was estimated by comparison to standard proteins in another gradient (curve extrapolated from catalase at 11.3 S, and bovine serum albumin at 4.6 S). The 3.5 S estimated for ICAM should be accurate to within ±0.5 S. Length measurements were made from prints magnified to 250,000 ×, subtracting 1 nm from each end for the estimated thickness of the shell of metal (Fowler, W. E. et al., *J. Molec. Biol.* 134:241–249 (1979)).

ICAM molecules were analyzed by sedimenting them through a glycerol gradient, in 0.2 M ammonium bicarbonate. The ICAM molecules remained near the top of the gradient, at a sedimentation coefficient estimated to be about 3.5 S. For a molecular mass of 92 kD, this indicates a value of $f/f_{min}=2.0$, indicative of a highly elongated molecule (Erickson, H. P., *Biophys. J.* 37:96a (1982)).

Rotary shadowed ICAM molecules appeared as thin rods, which were either straight, or with a single bend. Molecules with a uniform curvature or with two bends were rarely seen, suggesting a rigid rod structure with a single hinge point. Although the angle of the bend was somewhat variable, in most of the obviously bent molecules the angle was close to 90 degrees.

Length measurements gave a value of 16.6±0.24 nm (av.±s.d., n=25) for the straight molecules. For the bent molecules the long arm was 11.8±0.12 nm, and the short arm was 6.9±0.15 nm (n=21). The total length of the bent molecules, 18.7 nm, was somewhat longer than that measured for the straight molecules. It was possible that the population of straight molecules contained some in which the short art was bent toward the viewer, eclipsing the full profile. Thus, the bent molecules provided a more reliable population for length measurements. The rod appeared to have a uniform diameter, on the order of 2–3 nm.

The ICAM molecule was found to contain five repeats of IgG-like domains, which have dimension 4×2.5×2 nm. The total length of the ICAM molecule, 18.7 nm, indicates 3.7 nm per IgG repeat, and suggests that the domains are aligned with their long axes at a small angle to the axis of the rod. Models in which two or four of the IgG-like domains are paired with one another are too short. The bend was thus at a point about two-fifths along the rod, suggesting that it occurs between domains 2 and 3 or between domains 3 and 4, and dividing it into a short and a long arm.

EXAMPLE 39

Binding of ICAM-1 Deletion Mutants to LFA-1 and HRV

Figure 21:
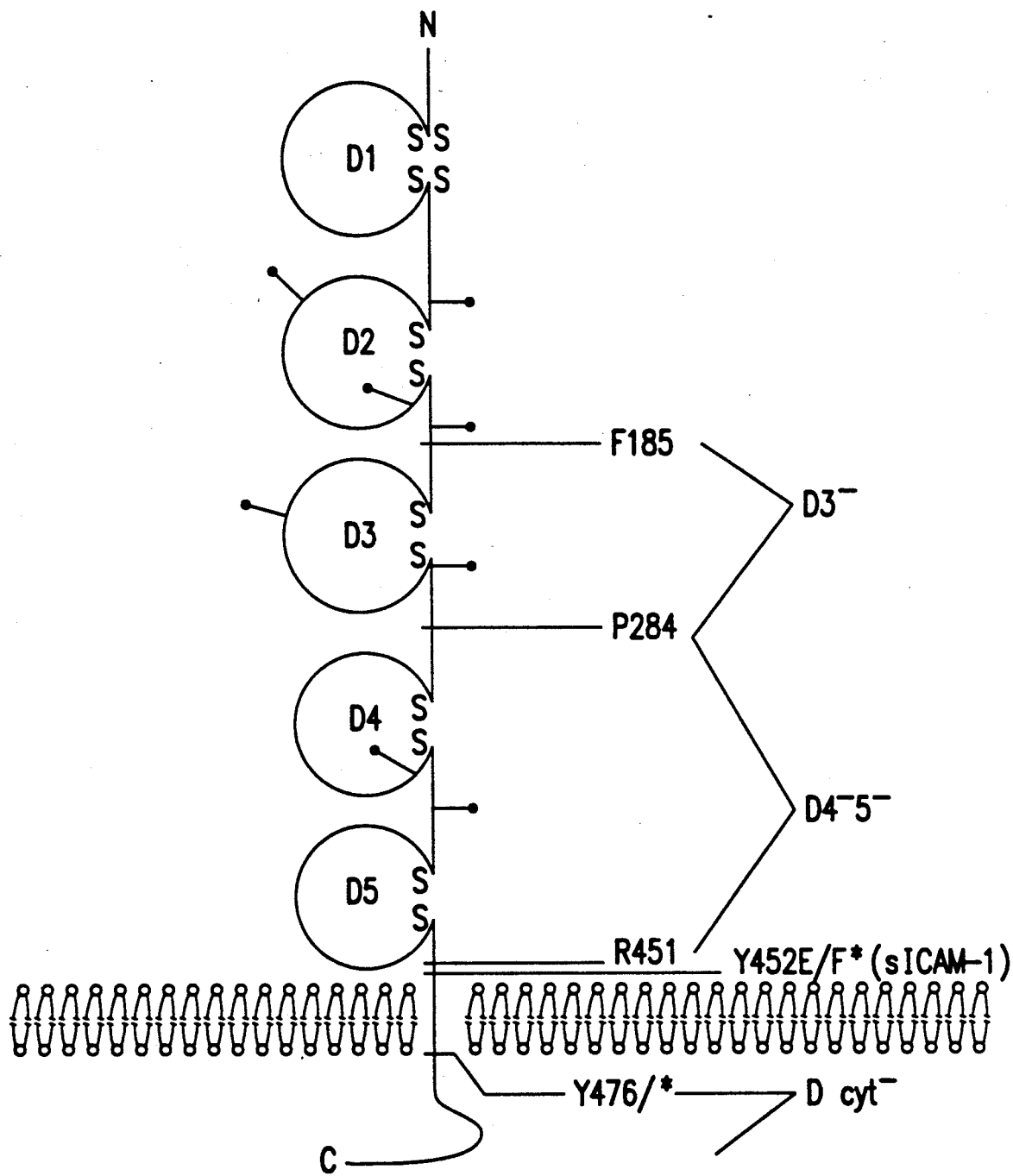
FIG. 21 shows an ICAM-1 schematic with position of domain deletions.
Figure 22A:
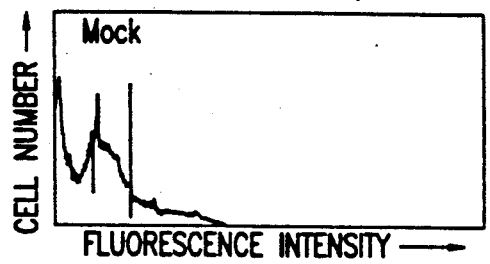
FIG. 22 (Panels A-E) shows the expression of ICAM-1 deletion mutants in COS cells. COS cells were analyzed by flow cytofluorometry following indirect immunofluorescence with RR1/1.
Figure 22B:
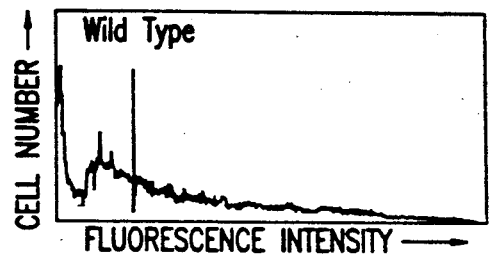
Figure 22C:
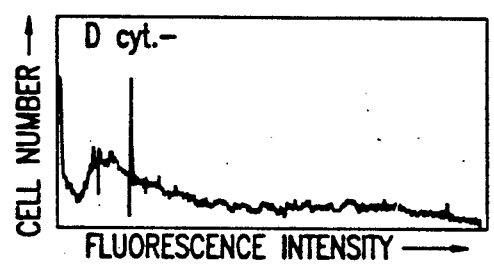
Figure 22D:
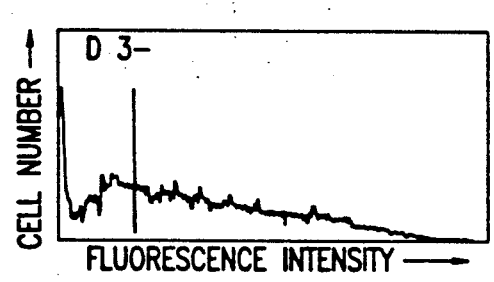
Figure 22E:
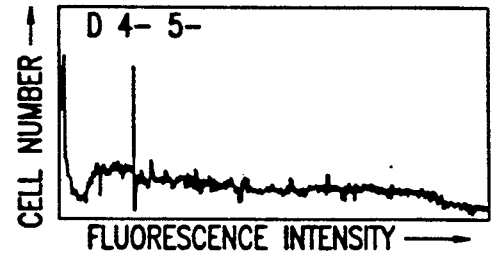

ICAM-1 is an integral membrane protein, of which the extracellular domain is predicted to be composed of 5 Ig-like C-domains. To localize the site(s) of LFA-1 and HRV contact to a particular ICAM-1 Ig-like domain(s), entire domains were deleted by oligonucleotide directed mutagenesis and tested functionally following expression in COS cells (FIG. 21). In addition, the cytoplasmic domain was deleted to determine its potential contribution to adhesion.

A secreted form of ICAM-1 including domains 1 through 5 was produced by mutation of the two most carboxyl extracellular residues Y452 and E453 to F and a translational stop codon respectively (pCDsD1-5). The entire cytoplasmic domain of ICAM-1 was deleted (DCyt.−) by transforming the codon for the carboxyl terminal transmembrane residue Y476 to a translational stop codon. D3 and D4 and 5 were deleted using long (48 bp) mutant oligonucleotides to span distal ICAM-1 sequence such that codons for F185 and P284 (D3−) and P284 and R451 (D4−5−) would be joined (FIG. 21). The desired deletion mutations were confirmed by DNA sequencing.

Following transfection, ICAM-1 mutants possessing deletions of the cytoplasmic (Y476/* or Dcyt.−), third (D3−) and fourth and fifth (D4−5−) domains were expressed in 50-60% of COS cells at similar characteristic broad levels (FIG. 22). Immunoprecipitation and SDS-PAGE of Dcyt−, D3−, and D4−5− ICAM-1 from COS cells, relative to wild-type, demonstrated a 3, 24 and 23 kD decrease, respectively. Wild-type ICAM-1, approximately 92 kD when expressed in COS cells, has a 55 kD core protein and thus each of the eight linked glycosylation sites may possess an average 4 kD oligosaccharide. Based on the predicted glycosylation of each domain (FIG. 21), the observed decreases in mass are reasonably consistent with the expected decreases of 3, 19 and 27 kD, respectively.

Figure 23:
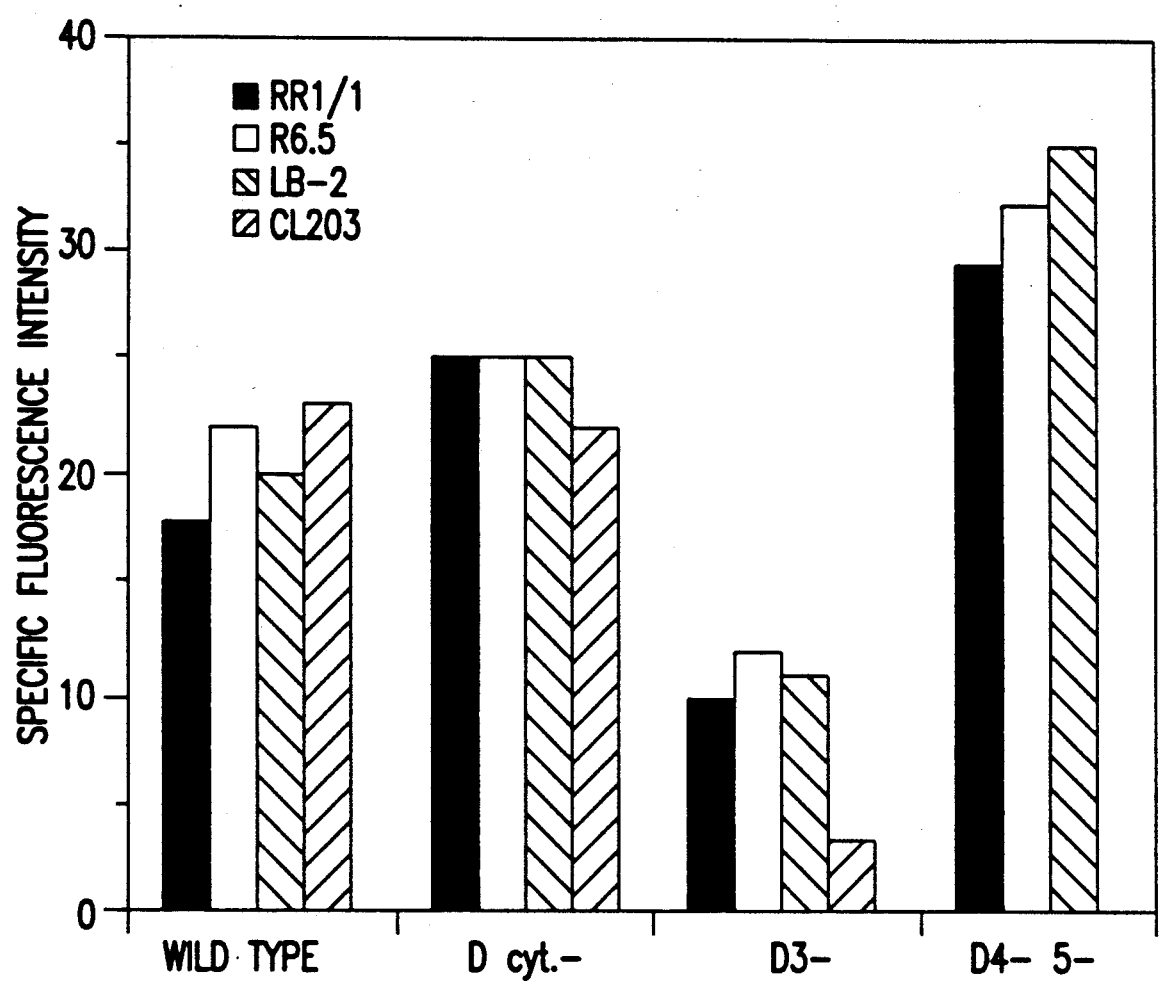
FIG. 23 shows the expression of ICAM-1 deletion mutants in COS cells by flow cytofluorometry following indirect immunofluorescence with MAbs RR1/1 (solid bar), R6.5 (open bar), LB-2 (stippled bar) or CL203 (hatched bar). Specific fluorescence intensity was determined with background binding to mock transfected cells subtracted.

Efficiency of expression of mutant ICAM-1 in these studies has been examined with a panel of 4 ICAM-1 MAb. These 4 MAb, RR1/1, R6.5, LB-2 and CL203 do not inhibit binding of one another to cell surface ICAM-1 as shown with biotinylated MAb, confirming previous results (Marlin, S. D., et al., *Cell* 51:813-819 (1987), which reference is incorporated herein by reference). They thus bind to four distinct epitopes. Following transfection ICAM-1 deletion mutants were expressed in COS cells at characteristic broad levels (FIG. 22). All MAb bound to the Dot mutant at levels equivalent to that of wild type (FIG. 23). Binding of CL203 was decreased upon removal of D3 and eliminated upon removal of D4 and D5. Binding of the other three MAb was unaffected for the D45 mutant and was decreased, although less so than for CL203, for the D3 mutant. Thus the epitopes for RR1/1, R6.5 and LB-2 are located within D1 or 2 and that of CL203 within D4 or 5. The Dcyt and D45 mutants are efficiently expressed while the D3 mutant appears expressed at about one-half the level of wild type.

Figure 24:
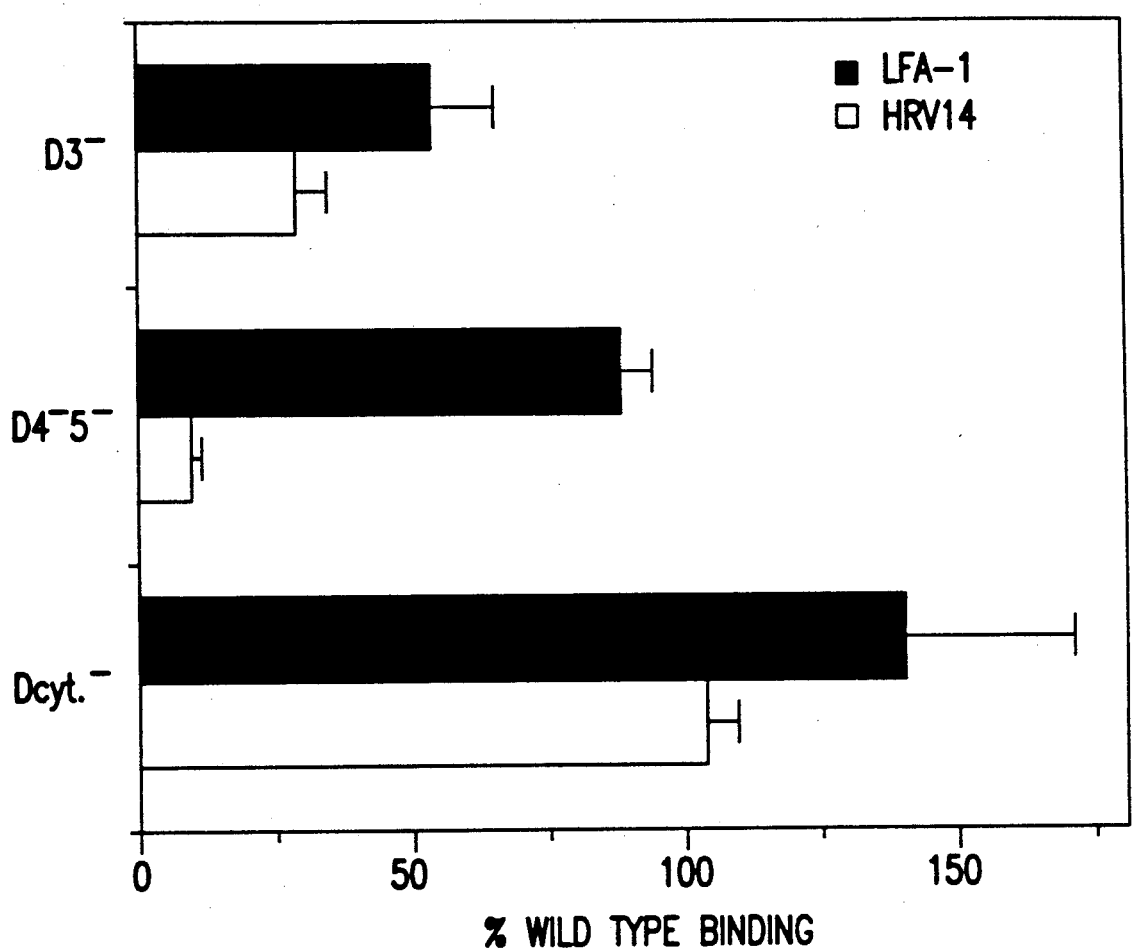
FIG. 24 shows binding of ICAM-1 deletion mutants to LFA-1 and HRV14. COS cells expressing ICAM-1 deletion mutants were tested for adherence to plastic bound LFA-1 and for binding 35S met-labeled HRV14. Standard error for multiple experiments (2-4) are indicated.

COS cells expressing all three deletion mutants adhere specifically to plastic-bound LFA-1 (FIG. 24, closed bars). Deletion of D4 and 5 had no significant effect on LFA-1 binding while deletion of D3 decreased LFA-1 binding to an extent comparable to its decreased expression. Thus D1 and 2 are sufficient for binding to LFA-1.

Amino acid substitutions in predicted β-turns in domains 1, 2 and 3 were also generated and functionally tested following expression in COS cells. The R6.5 epitope was thus localized to the sequence E111GGA in domain 2 and may also involve E39 in domain 1 whereas RR1/1 and LB-2 are both dependent on R13 in domain 1 (Table 25). In addition, RR1/1 binding is decreased by mutations in the sequence D71GQS. Mutations eliminating N-linked glycosylation sites at N103 and N165 result in decreased RR1/1, R6.5 and LB-2, LFA-1 HRV binding. These mutations appear to effect processing such that ICAM-1 dimers are generated.

Other mutations in domain 2 or 3 did not result in altered LFA-1 adhesion (FIGS. 21 and 22). The amino acids in domain 1, R13 and D60 are important in antibody binding (Table 25).

Binding of HRV14 to ICAM-1 domain deletion mutants demonstrates that D1 and 2 is also sufficient for this interaction (FIG. 24, open bars). The decreased binding to the D3− mutant may be for the same reason mentioned above for LFA-1 binding. However, deletion of D4 and 5 results in a consistent decrease in binding HRV14 which is not found for LFA-1. Thus as the binding site on ICAM-1 becomes immersed into the cellular glycocalyx by the predicted 8 nm shortening when D4 and 5 are deleted, or alternatively as it becomes less flexible, it becomes less accessible to HRV.

The binding of LFA-1 and HRV14 to D1 and 2 and the above-reported mAb epitope localization data correlate with previous mAb blocking data. Thus the ICAM-1 sites which interacts with RR1/1, R6.5 and LB-2 are localized to domains 1 and 2 block both LFA-1 and HRV binding, whereas the ICAM-1 sites which interact with CL203 are localized to domains 4 and 5. CL203 blocks neither cell adhesion nor virus adhesion (Maio, M. et al., *J. Immunol.* 143:181-188 (1989); Staunton, D. E., et al., *Cell* 52:925-933 (1988)), which references are incorporated herein by reference).

Thus, LFA-1 and HRV binding appears to be a function of the amino terminal Ig-like domain of ICAM-1. FIG. 20 shows an alignment of ICAM amino terminal domains.

EXAMPLE 40

ICAM-1 Amino Acid Substitution Mutants

Features of the hypothetical Ig-like domains of ICAM-1 were used to guide not only the deletion experiments described above but also amino acid substitutions. The three amino-terminal Ig-like domains of ICAM-1 are predicted to possess 7 b strands each. These strands are predicted to be arranged in two sheets, which are connected by the intradomain disulfide bond to form a "sandwich." The loops connecting the b strands in immunoglobulins form the antigen-binding site, and are hypothesized to be utilized in intermolecular contacts in other Ig superfamily members (Williams, A. F. et al., *Ann. Rev. Immunol.* 6:381-405 (1988), which reference is incorporated herein by reference).

The strategy followed was to first introduce two to four amino acid substitutions per loop in domains 1-3. If effects were found, single substitutions were then made. Finally, in some areas of interest substitutions were introduced into b stands.

Mutants of ICAM-1 were generated in the following manner. Oligonucleotide-directed mutagenesis based on the method of Kunkel (Kunkel, T. A., *Proc. Natl. Acad. Sci. USA* 82:488-492 (1985), with modifications by Peterson A. and Seed B. (*Nature* 329:842-846 (1987)), both of which references are incorporated herein by reference) was utilized to generate ICAM-1 deletions and amino acid substitutions. Mutations were made using a single strand uracil-containing template of ICAM-1 cDNA subcloned into the expression vector CDM8 (pCD1.8), which was previously described (Staunton, D. E. et al., *Cell* 56:849-853 (1989)). Mutant ICAM-1 oligonucleotides which confer a unique restriction site were used to prime a second strand synthesis reaction. Following a transformation into *E. coli*, mutants were isolated by screening for the unique restriction sites. In general, two or more isolates of each mutant were tested in binding studies following COS cell transfection.

The results of this experiment are summarized in Table 25. In Table 25, the notation for the mutations uses the one-letter code for the wild-type sequence followed by a slash and the one-letter code for the corresponding mutant sequence. The position of the first amino acid within the sequence is indicated. Wild type residues precede the slash followed by the residues they were substituted for in the mutant. COS cells expressing ICAM-1 mutants were tested for adherence to LFA-1 coated plastic and for binding 35S met-labeled HRV14. LFA-1 and HRV14 binding is normalized for percent of cells expressing mutant ICAM-1 and for binding of wild type expressing cells. Binding is presented as mean and standard error (SE) for multiple experiments (n). Effects of two-fold or greater were reproducible in LFA-1, HRV and mAb binding assays and thus considered significant (bold and underlined). The specific linear fluorescence intensity (SLFI) of CL203 for each mutant is normalized to that of wild type CL203 SLFI (% WT) as discussed above. The SLFI of RR1/1, R6.5 and LB-2 SLFI is normalized to the CL203 SLFI of the mutant (% CL203) as described above.

TABLE 25

| | Binding of ICAM-1 Amino Acid Substitution Mutants to LFA-1 and HRV14 | | | | | | | | |
|---|---|---|---|---|---|---|---|---|---|
| | LFA-1 Binding | | HRV Binding | | CL203 | | SLFI (% CL203) | | |
| Mutation | % | ±SE | % | ±SE | % WT | ±SE | RR/1 | R6.5 | LB-2 |
| D1 | | | | | | | | | |
| Q1T/KA | 119 | 23(2) | 11 | 4(2) | 230 | 61(2) | 94 | 115 | 113 |
| Q1/E | 175 | 53(3) | 149 | 57(3) | 135 | 21(3) | 154 | 145 | 136 |
| Q1/K | 97 | 20(2) | 78 | 29(2) | 168 | 17(3) | 109 | 121 | 106 |
| S3VS/AGL | 18 | 5(3) | 61 | 32(2) | 121 | 21(2) | 5 | 31 | 9 |
| S3/T | 149 | 38(3) | 196 | 72(3) | 224 | 32(3) | 111 | 114 | 117 |
| V4/G | 64 | 17(3) | 30 | 13(4) | 111 | 39(3) | 47 | 73 | 58 |
| S5/T | 104 | 12(2) | 125 | 38(3) | 251 | 24(3) | 107 | 107 | 120 |
| K8/E | 84 | 6(2) | 132 | 18(2) | 111 | 11(2) | 104 | 121 | 110 |
| R13G/EA | 2 | 2(4) | 3 | 1(2) | 132 | 4(2) | 0 | 31 | 0 |
| R13/E | 1 | 1(3) | 10 | 5(3) | 202 | 34(3) | 4 | 48 | 4 |
| R13/K | 98 | 16(3) | 123 | 13(2) | 189 | 45(4) | 133 | 117 | 121 |
| R13/Q | 78 | 23(3) | 60 | 0(2) | 161 | 36(3) | 73 | 73 | 47 |
| G15/SA | 120 | 17(3) | 164 | 23(2) | 172 | 44(2) | 89 | 88 | 89 |
| T20CS/ACT | 91 | 22(3) | 130 | 36(3) | 148 | 24(3) | 86 | 95 | 86 |
| S24/A | 80 | 8(2) | 99 | 7(2) | 158 | 4(2) | 125 | 115 | 125 |
| D26QPK/ALPE | 30 | 13(3) | 13 | 7(3) | 126 | 10(3) | 52 | 89 | 80 |
| Q27/L | 37 | 6(3) | 57 | 26(4) | 33 | 5(4) | 75 | 75 | 125 |
| E34/A | 0 | 0(3) | 66 | 22(4) | 132 | 23(4) | 142 | 150 | 142 |
| K39KE/ERQ | 99 | 25(4) | 61 | 4(3) | 84 | 6(3) | 47 | 93 | 87 |
| K40/A | 124 | 4(2) | 89 | 20(2) | 146 | 4(2) | 123 | 106 | 106 |
| G46NN/ASI | 49 | 15(4) | 9 | 5(2) | 151 | 24(4) | 140 | 107 | 113 |
| N48/H | 88 | — | 81 | 2(2) | 164 | 21(2) | 123 | 94 | 100 |
| R49KV/EKL | 123 | 20(2) | 49 | 22(2) | 233 | 21(2) | 103 | 97 | 52 |
| K50V/EL | 29 | 8(2) | 10 | 8(2) | 103 | 22(2) | 23 | 69 | 23 |
| Y52/F | 72 | 0(2) | 174 | 46(3) | 152 | 10(2) | 90 | 95 | 119 |
| Y52/FA | 138 | 35(2) | 125 | 33(2) | 100 | 0(2) | 141 | 133 | 117 |
| N56V/HM | 121 | 13(2) | 101 | 42(2) | 121 | 21(2) | 106 | 125 | 125 |
| Q58EDS/AKDI | 3 | 3(3) | 0 | 0(2) | 98 | 10(3) | 10 | 22 | 7 |
| Q58/H | 109 | 13(2) | 1 | 1(2) | 135 | 35(2) | 93 | 107 | 93 |
| E59/K | 134 | 50(2) | 105 | 20(2) | 130 | 1(2) | 127 | 109 | 136 |
| E59/Q | 84 | 38(2) | 92 | — | 195 | 25 | 112 | 106 | 125 |
| D60S/KL | 1 | 1(3) | 1 | 0(2) | 105 | 17(2) | 0 | 21 | 0 |
| D60/K | 14 | — | 4 | 0(2) | 89 | 8(2) | 0 | 31 | 0 |
| D60/N | 92 | 33(4) | 89 | 14(3) | 127 | 14(3) | 100 | 138 | 108 |
| D60/Q | 18 | 6(2) | 20 | 8(2) | 80 | 1(2) | 30 | 54 | 31 |
| S61/I | 59 | 18(3) | 111 | 4(2) | 140 | 18(5) | 82 | 100 | 100 |
| Q62PM/API | 104 | 48(3) | 182 | 61(2) | 200 | 29(4) | 59 | 81 | 73 |
| M64/I | 111 | 13(2) | 107 | 3(2) | 183 | 40(2) | 83 | 111 | 116 |
| Y66/T | 135 | — | 204 | — | 144 | — | 109 | 104 | 113 |
| N68/K | 101 | 1(2) | 137 | 23(2) | 153 | 8(2) | 97 | 96 | 102 |
| D71GQS/NGEL | 1 | 1(4) | 21 | 12(3) | 161 | 54(3) | 0 | 48 | 26 |
| D71/E | 118 | 28(2) | 140 | 7(2) | 124 | 6(2) | 89 | 100 | 82 |
| D71/N | 79 | 3(3) | 62 | 1(2) | 109 | 26(4) | 44 | 94 | 83 |

TABLE 25-continued

Binding of ICAM-1 Amino Acid Substitution Mutants to LFA-1 and HRV14

| Mutation | LFA-1 Binding % | ±SE | HRV Binding % | ±SE | CL203 % WT | ±SE | SLFI (% CL203) RR/1 | R6.5 | LB-2 |
|---|---|---|---|---|---|---|---|---|---|
| Q73/H | 12 | 10(4) | 117 | 31(5) | 139 | 27(5) | 21 | 80 | 80 |
| Q73/T | 40 | 12(4) | 133 | 46(2) | 218 | 48(2) | 71 | 86 | 114 |
| S74/A | 70 | 6(2) | 156 | 35(2) | 129 | 29(2) | 119 | 119 | 113 |
| T75/A | 59 | 28(2) | 119 | 8(2) | 153 | 10(2) | 94 | 94 | 115 |
| K77T/ES | 87 | 22(4) | 42 | 14(4) | 151 | 38(3) | 88 | 80 | 84 |
| Y83/S | 42 | 9(2) | 86 | 64(2) | 125 | — | 60 | 70 | 50 |
| E87/K | 65 | 10(5) | 27 | 10(3) | 94 | 12(3) | 64 | 64 | 79 |
| R88V/EA | 95 | 1(2) | 152 | 1(2) | 113 | 14(3) | 74 | 100 | 121 |
| E90/Q | 122 | 45(3) | 157 | 57(2) | 152 | 17(2) | 90 | 92 | 112 |
| E90/K | 34 | 11(2) | 50 | 22(4) | 29 | 5(4) | 100 | 123 | 108 |
| D2 | | | | | | | | | |
| L91/A | 87 | 7(2) | 105 | — | 15 | — | 79 | 142 | 133 |
| G101K/AN | 97 | 55(3) | 140 | 60(2) | 142 | 21(3) | 85 | 85 | 85 |
| N103/K | 12 | 6(2) | 13 | — | 91 | 9(2) | 17 | 60 | 22 |
| E111GGA/KAGS | 103 | 35(3) | 162 | 73(2) | 122 | — | 81 | 0 | 89 |
| N118/Q | 54 | 22(3) | 110 | — | 139 | 9(3) | 93 | 85 | 93 |
| R125/E | 81 | 27(3) | 157 | 15(2) | 145 | 37(2) | 181 | 133 | 104 |
| E127/R | 82 | 29(2) | 131 | 4(2) | 191 | 22(2) | 100 | 119 | 106 |
| K128/R | 109 | 52(3) | 137 | 37(2) | 190 | 35(2) | 100 | 118 | 109 |
| V136GE/GVK | 92 | 53(3) | 117 | 1(2) | 171 | 42(2) | 220 | 172 | 138 |
| R149RD/EEG | 81 | 40(2) | 139 | 56(2) | 159 | 47(2) | 166 | 189 | 166 |
| H152HGA/EEGS | 85 | 52(2) | 82 | 20(2) | 94 | — | 103 | 94 | 112 |
| A115N/SV | 0 | 0(3) | 12 | 8(2) | 60 | 6(2) | 0 | 0 | 0 |
| N156/E | 60 | 4(2) | 107 | — | 182 | 57(2) | 84 | 95 | 95 |
| R166PQ/EPA | 75 | 8(2) | 25 | 8(3) | 94 | 10(3) | 100 | 109 | 64 |
| N175TSA/QTLG | 26 | 10(4) | 40 | 8(3) | 75 | 16(3) | 19 | 50 | 44 |
| N175/A | 67 | 3(3) | 129 | 46(2) | 80 | 9(2) | 162 | 175 | 150 |
| S177/G | 59 | 1(2) | 66 | 6(2) | 87 | 6(3) | 136 | 118 | 90 |
| A178/G | 59 | 3(2) | 102 | — | 304 | — | 63 | 69 | 74 |
| D3 | | | | | | | | | |
| A189/SI | 91 | 3(2) | 168 | — | 138 | 38(2) | 175 | 166 | 166 |
| D203TQ/TAD | 91 | 53(2) | 111 | 8(2) | 125 | — | 178 | 116 | 86 |
| D213GL/HGV | 90 | 52(3) | 99 | 13(2) | 128 | 28(2) | 231 | 175 | 107 |
| D229QR/HLE | 90 | 37(3) | 106 | 11(2) | 210 | 59(2) | 94 | 92 | 100 |
| N240DS/KNA | 147 | 29(3) | 82 | 32(2) | 142 | — | 113 | 125 | 132 |
| E254DE/KEK | 122 | 33(2) | 99 | 23(2) | 180 | 63(2) | 178 | 129 | 81 |
| N269QSQI/IQAEQ | 101 | 9(2) | 108 | 45(2) | 95 | 15(3) | 162 | 150 | 150 |

Since the epitope of mAb CL203 localizes to D4 or 5, whereas D1–D3 were subjected to amino acid substitutions, CL203 was used to determine the level of expression of ICAM-1 amino acid substitution mutants in transfected COS cells. Binding of ICAM-1 mutants to LFA-1 and HRV was normalized with respect to mAb CL203 binding and to binding obtained with wild-type ICAM-1. Furthermore, since mAb RR1/1, R6.5, and LB-2 bind to distinct epitopes, a loss of two or more of these epitopes indicates a gross disruption of structure and thus corresponding effects on LFA-1 and HRV binding were discounted. Two mutations, Q27/L and E90/K, which demonstrate a specifically reduced level of expression as measured with CL203, were also discounted as lower expression may reflect decreased efficiency of folding of D1 where these mutations occur.

Amino acid substitution mutants which demonstrate a decrease in the binding of only one ICAM-1 mAb suggests that the corresponding wild-type residues contribute to the mAb epitope (Table 25). Decreased binding of mAb to amino acid substitution mutants demonstrates that the epitope for RR1/1 involve the residues D71 and Q73 and sequences at D26, K39 and Q62. The epitope for R6.5 is completely and specifically disrupted by a mutation in the sequence at E111 in D2. LB-2 binding is specifically affected by mutations in sequence at R49 in D1 and R166 in D2.

Domains 1 and 2 appear to be conformationally linked. Twelve of 53 mutations in D1, and a similar proportion in D2, 4 of 18, disrupt binding of RR1/1, R 6.5, and LB.2 mAb, LFA-1, and HRV. Since these ligands bind to different sites (the mAb) or only partially overlapping regions (LFA-1 and HRV, see below), the ability of mutations widely spread throughout both D1 and D2 to have common effects suggests that the conformation of D1 is dependent on the conformation of D2 and vice versa. In contrast, none of the mutations in D3 affect binding of these ligands, and none of these mutations affects binding of CL203 which localizes to D4 or D5. This indicates that there is substantial contact between D1 and D2, but that D1 and D2 are conformationally independent of D3; i.e., there may be a hinge between D2 and D3. The most disruptive mutations involve residues R13 and D60 which would be predicted in an Ig-model (see below) to come into close proximity to residues in D2. Deletion of residues in D2 (residues P95-A189) has resulted in a lack of cell surface expression, further indicating that proper folding of ICAM-1 depends on D1 and D2 interactions.

Conformational disruption in two mutations is reflected in abberent disulfide bond formation. Immunoprecipitation and non-reducing SDS-PAGE of 12 D1 and D2 mutants revealed that two of them, N103/K and A155N/SV, to be ICAM-1 disulfide linked dimers. Residues N103 and N156 occur close to C108 and C159 which are predicted to form the intradomain disulfide bridge of D2.

Mutations with the strongest effect on LFA-1 binding localized to D1. The most dramatic mutations are E34/A which completely eliminates LFA-1 binding and Q73/H, which decreases it 10-fold (Table 25). A different substitution at Q73, Q73/T, demonstrated a two-fold decrease. The mutations D26QPK/ALPE and G46NN/ASI decrease LFA-1 binding 2-3 fold. In the second domain the mutants N118/Q, N156/E, N175/A and S177/G specifically decreased LFA-1 binding approximately two-fold. These four mutants were found to affect three of the four N-linked glycosylation sites in D2; there are no N-linked glycosylation sites in D1 (FIG. 21). Thus, N-linked carbohydrate may have a small but not critical role in LFA-1 binding. The effect of these mutations may be more indirect. One indirect effect D2 N-linked glycosylation may have is a change in the flexibility of the hinge. None of the mutations in D3 affected LFA-1 binding, in agreement with the lack of effect of deleting D3.

A number of mutations demonstrate that D1 is more important than D2 in HRV binding and that HRV and LFA-1 binding sites partially overlap. Seven mutants decrease HRV14 binding but have no effect on LFA-1 binding. The two which demonstrated the greatest effect involved amino acid substitutions in D1. Q58/H virtually eliminated HRV14 binding and QLT/KA resulted in a ten-fold decrease. Four other mutations in D1 demonstrated a specific two-fold effect on HRV binding, K39KE/ERQ, R49KV/EKL, D71/N and K77T/ES. One mutation in D2, R155PQ/EPA, resulted in a four-fold decrease in HRV14 binding. D3 mutations did not affect HRV binding.

Of the 4 D1 mutations discussed above which affect LFA-1 binding, 3 affect HRV binding as well. The mutants, D26QPK/ALPE and G46NN/ASI, affected HRV14 binding ten-fold and LFA-1 binding two- to three-fold. The E34/A that totally eliminates LFA-1 binding decreases HRV binding 2-fold. Four mutations in D2 that decreased LFA-1 binding had little or no effect on HRV binding.

Thus residues which were identified as critical (ten-fold or greater affect) to LFA-1 or HRV binding demonstrated a separation in function. The mutations E34/A and Q73/H which markedly decrease LFA-1 binding have a weak or a non-detectable affect on HRV binding. Conversely, mutations have been described above that have a profound affect on HRV binding yet do not affect LFA-1 binding. An overlap in binding sites is, however, demonstrated by two mutations which affect both LFA-1 and HRV binding. In addition, proximity of binding sites is suggested by mutations which are adjacent in sequence position yet affect binding of either LFA-1 or HRV (discussed further below).

Ten sequences/residues important to LFA-1 and HRV14 binding were defined in D1 in contrast to one sequence and potentially three N-linked glycosylations in D2. Residues or sequences critical to binding were identified in D1, not in D2. Further, none of the substitutions in D3 altered binding to LFA-1 or HRV14 confirming the results of deleting D3. Thus the primary site of LFA-1 and HRV14 contact is located in D1.

Figure 25:
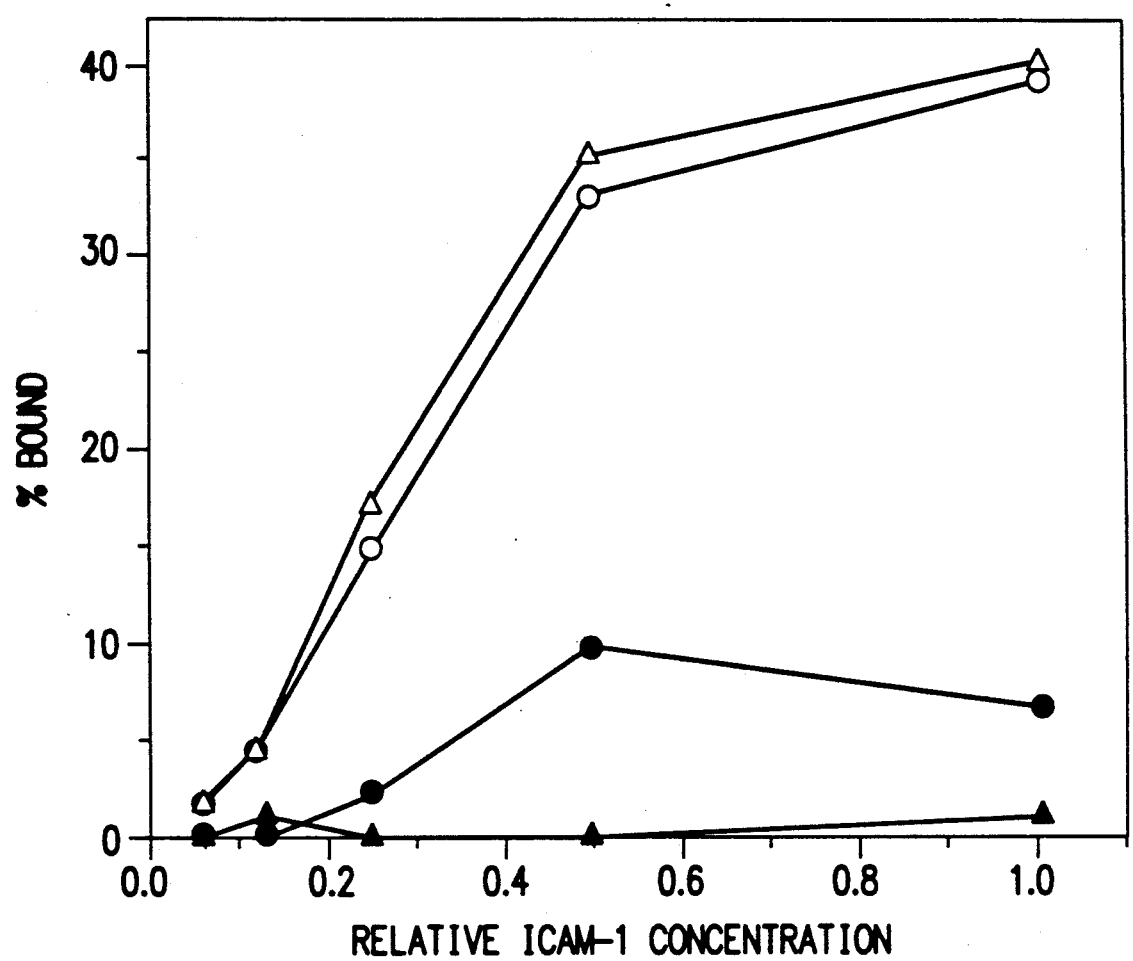
FIG. 25 shows binding of HRV14 to ICAM-1 in the absence of divalent cations. Binding of 35SHRV14 to increasing concentrations of plastic bound ICAM-1 occurred in HRV-buffer with 10 mM Mg++ (open circles) or HRV-buffer minus added Mg++ but with 5 mMEDTA (open triangles). SKW3 binding was in HRV buffer with 0.5 mMMg++ (solid circles) or 5 mM EDTA (solid triangles).

The interaction of LFA-1 and HRV14 was further compared with regard to the requirement for divalent cations. It had previously been demonstrated that ICAM-1 on the cell surface or bound to plastic binds cell surface or purified LFA-1 in a $Mg^{2+}$ dependent manner (Marlin, S. D., et al., Cell 51:813-819 (1987); Staunton, D. E., et al., Nature 339:61-64 (1989)). The binding of the LFA-1 expressing T lymphoma line SKW3 and HRV to purified ICAM-1 was compared on a plastic substrate. Purified ICAM-1 bound to plastic was utilized and the LFA-1 expressing T-cell line was found to bind ICAM-1 only in the presence of $Mg^{2+}$ (FIG. 25). In contrast, the binding of HRV14 to ICAM-1 did not significantly differ in the presence of 10 Mm $Mg^{2+}$ or 5 Mm EDTA. This was confirmed over a range of ICAM-1 densities on the substrate. The LFA-1:ICAM-1 and HRV:ICAM-1 interaction are thus distinctly different in divalent cation requirements.

The above experiments demonstrate that the extracellular region of ICAM-1 exists as a 20 nm hinged rod. This indicates that the five predicted Ig-like domains are extended and unpaired, and are aligned end-to-end rather than side-by-side. ICAM-1 is thus similar in overall structure to NCAM (Beckers, A., et al., *Immunochem.* 11:605-609 (1974)). The total length of extracellular ICAM-1 is 18.7 nm and therefore 3.7 nm per Ig domain. The long arm of NCAM, which comprises five IgG-like domains, had a length of 17.6-18.7 nm, essentially identical to the total length of the ICAM molecule (Beckers, A., et al., *Immunochem.* 11:605-609 (1974)).

Another striking similarity in the structure of ICAM and NCAM is that both molecules have a bend, typically at 90 degrees but with variation indicating flexibility. In ICAM this bend is probably between two IgG-like domains, giving a long arm with three domains and a short arm with two. The finding that the conformation of D1 and D2 are dependent upon one another indicates that the hinge is located between D2 and D3. The sequence at the D2-D3 border demonstrates the most proline rich region in ICAM-1 (4 prolines within 10 residues). This is consistent with Ig hinge sequences which are characteristically proline rich. Indeed, all 4 prolines in this region are spaced identically to 4 prolines in the hinge region of mouse IgG3.

In NCAM there is no bend within the five IgG-like domains (these form the apparently rigid long arm equal to the total length of ICAM); rather, the bend immediately follows the sequence of IgG-like domains. The short arm of NCAM contains two fibronectin-like domains, the membrane spanning segment and cytoplasmic domain (Beckers, A., et al., *Immunochem.* 11:605-609 (1974)).

Remarkably, the cell adhesion molecule LCAM, which has no IgG-like domains and is unrelated to ICAM or NCAM, also has a 90 degree bend (Becker, J. W., et al., *Proc. Natl. Acad. Sci. (U.S.A.)* 86:1088-1092 (1989)).

This common feature of cell adhesion molecules would thus appear to be functionally important to permit an extended segment of the molecule, rather than just the tip, to face and form an interface with its receptor. It would allow binding sites located on the distal, flexible segment to bind to receptors oriented at different angles and located at varying distances with respect tot the membrane of the cell bearing the ICAM-1 molecule. Furthermore, segmental flexibility provided by the hinge should increase the rate of diffusion of the binding site within the volume of solvent above the cell surface to which it is limited by its membrane tether, thereby enhancing the kinetics of binding to adhesion receptors or viruses and increasing the efficiency of these interactions.

The rod-shaped unpaired domain organization of ICAM-1 thus facilitates adhesion by elevating binding sites to a critical distance above the cell surface. Rhinovirus binding was more sensitive than LFA-1 binding to deleting domains 4 and 5, which is predicted to shorten ICAM-1 by 7.4 nm and affect its flexibility. This may be related to 2 differences between rhinovirus and LFA-1. First, the binding site on HRV is proposed to be submerged in a 2.5 nm deep cleft within a canyon which forms a moat around the five-fold axis of the virion (Rossmann, M. G., et al., *Nature* 317:145–153 (1985)), while electron microscopic studies of integrins suggest a 10×8 nm globular binding domain supported on 18 nm-long stalks above the cell surface (Carrell, N. A. et al., *J. Biol. Chem.* 260:1743–1749 (1985); Nermut, M. V. *EMBO J.* 7:4093–4099 (1988)). The cellular glycoclyx (Williams, A. F. et al., *Ann. Rev. Immunol.* 6:381–405 (1988)) into which ICAM-1 is submerged by its shortening may repel the bulkier rhinovirus more than LFA-1. Second, binding of multiple ICAM-1 molecules to rhinovirus (Colonno, R. J. et al., *Proc. Natl. Acad. Sci. (U.S.A.)* 85:5449–5453 (1988)) would require close proximity of the ICAM-1 molecules one to another, and this packing may be hindered by shortening or loss in flexibility. LFA-1 interaction with ICAM-1 also requires multivalent interactions, but the LFA-1 molecules may well be separated from one another, and, based on content of one alpha and beta subunit each, are predicted to have one binding site each.

Figure 26:
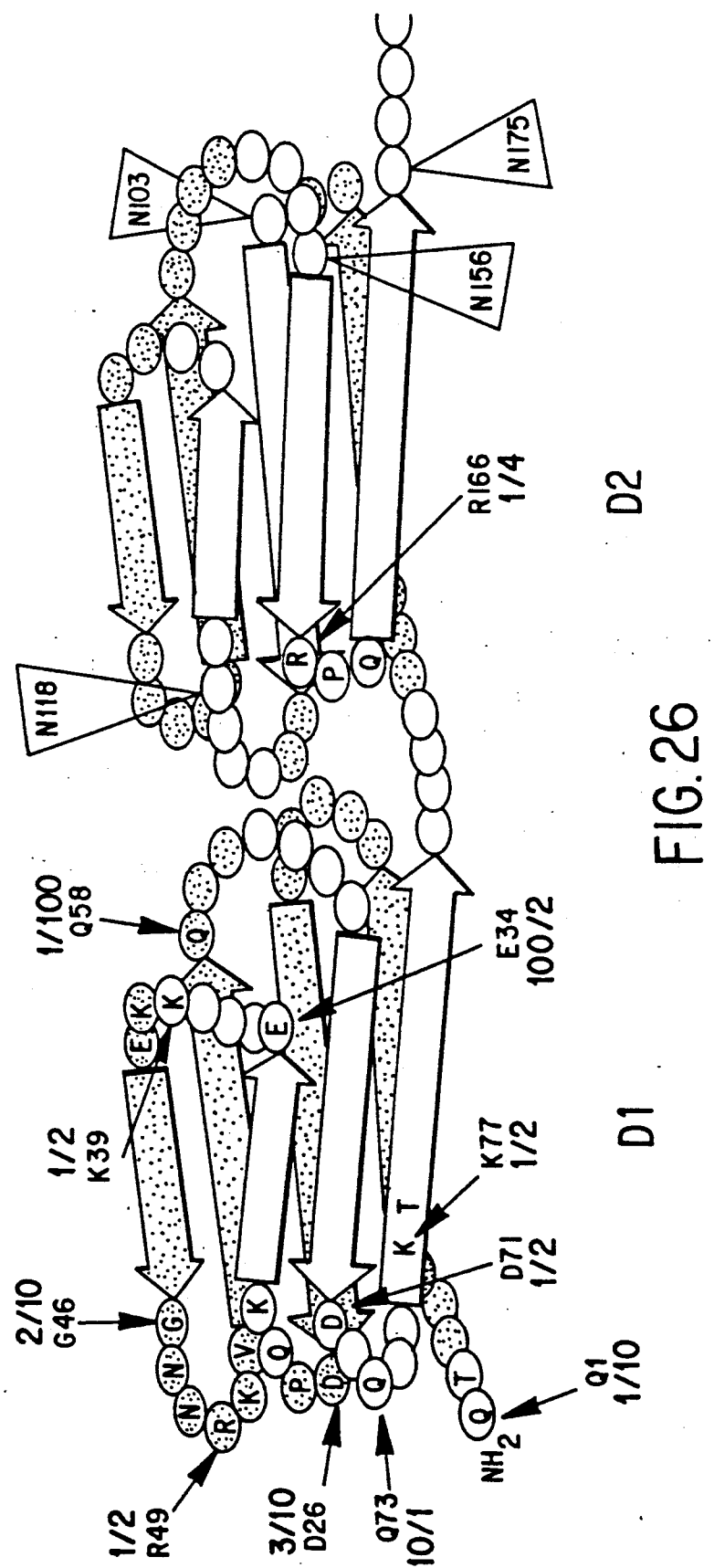
FIG. 26 shows a model of ICAM-1 D1 and D2 tertiary structure: Localization of LFA-1 and HRV binding sites. The basic tertiary structure of an Ig constant domain (Wright, S. D., et al., *Proc. Natl. Acad. Sci. USA* 85:7734-7738 (1988)) was modified to accommodate the predicted b strands (wide arrows) and b turns of ICAM-1 D1 and D2 (Staunton, D. E., et al., *Nature* 339:61-64 (1989a)). Residues involved in LFA-1 or HRV14 binding are indicated. The effect of their corresponding mutations on LFA-1/HRV14 binding (X-fold decrease) is indicated, respectively (outline print). The position of D2 N-linked oligosaccharides (open triangle) are indicated.

The unpaired domain nature of ICAM-1 and the location of sequences/residues involved in binding to D1 is consistent with ICAM-1 D1 binding within the deep cleft of the proposed HRV canyon binding site. The interface of ICAM-1 and HRV may be envisioned in at least two different models. Based upon predicted secondary structure, ICAM-1 sequences were positioned in an Ig fold model (FIG. 26). Four of the six D1 sequences which were implicated in HRV contact QIT, D26QP, G46NN, and R49KV, locate in this model to the distal half of D1. The dimension of the deep cleft (3–1.2 nm wide and 2.5 nm deep) is such that slightly more than half an Ig-like domain (4 nm long and 2.5–2 nm wide) could be inserted. The distal half of ICAM-1 D1 may therefore bind to residues within the cleft such that the long axis of D1 is approximately perpendicular to the surrounding surface of the virion. The distance between the boundary of each deep cleft, approximately 4 nm, is great enough to allow an ICAM-1 to occupy all five clefts around the five-fold axis of the virion. Other sequences implicated in HRV contact, K39KE, Q58 and R166906PQ, may interact with HRV residues in the rim of the canyon. Alternatively, these residues in D1 and 2 may not form bonds with HRV residues but contribute inter or intra domain bonds important to binding conformation. A second model of ICAM-1: HRV interaction would be ICAM-1 D1 contacting residues of the cleft such that the long axis of D1 would form an acute angle with the surrounding virion surface. Thus D1 would be more parallel and horizontal with the canyon. This may result in blocking by steric hindrance of some sites around the five-fold axis.

Because 3 non-crossblocking ICAM-1 mAb block both LFA-1 and rhinovirus-14 binding it was suggested previously that LFA-1 and rhinovirus-14 contact sites on ICAM-1 are in close proximity (Staunton, D. E. t al., *Cell* 56:849–853 (1989)). Our present studies show the binding site for rhinovirus-14. We have modeled these sequence positions on ICAM-1 domains 1 and 2 (FIG. 26) assuming an Ig domain structure (Williams, A. F. et al., *Ann. rev. Immunol.* 6:381–405 (1988)) although the Ig fold may differ in some important way for Ig family members with unpaired domains. Characterization of the mutants G46NN/ftSI, D26QPK/ALPE and E34/A reveals common use of ICAM-1 sequences in LFA-1 and rhinovirus-14 binding. The predicted location of contact sequences in the Ig domain model is consistent with close proximity or overlap of LFA-1 and rhinovirus-14 binding sites. Residues implicated in LFA-1 binding, such as Q73 and G46, are proximal to residues implicated in rhinovirus-14 binding, D71 and R49. Thus rhinovirus-14 appears to have evolved to bind to a site on ICAM-1 which overlaps with the LFA-1 binding site. The two binding sites are clearly distinguished, however, by mutations at E34 and Q58 which dramatically and selectively abolish LFA-1 and rhinovirus binding, respectively. Three of the four D1 sequences implicated in LFA-1 contact and 6 of the 9 sequences implicated in rhinovirus-14 contact locate to the membrane-distal half of D1 in this model; however, some of the sites where mutations have the most dramatic effect localize to the proximal half. The overlap of rhinovirus and LFA-1 binding sites in domain 1 appears to be a consequence of the favorability of this domain as an adhesive interaction site as outlines above. Alternatively, ICAM-1 might be a receptor with a triggering function in antigen-presenting cells. In this scenario, binding to domain 1 would trigger through ICAM-1 a response that would be advantageous to rhinovirus, for example by stimulating nasal secretions that would help spread the virus to other people. This would be an example of evolutionary mimicry.

The contact site on ICAM-1 differs from that of many other integrin ligands in sequence and structure. Many integrins which bind extracellular matrix proteins bind to an RGD or an RGD-like sequence in their ligands (Ruoslahti, E., t al., *Cell* 44:517–518 (1986); Hynes, R. O., *Cell* 48:549–554 (1987)). Human ICAM-1 has no RGD sequences but several RGD-like sequences (Simmons, D. t al., *Nature* 331:624–627 (1988); Staunton, D. E. et al. *Cell* 52:925–933 (1988)); murine ICAM-1 contains an RGD sequence. However, none of these sites correspond to residues defined by our mutagenesis studies as important in LFA-1 binding to ICAM-1. Instead of a contiguous sequence like RGD, a number of discontiguous sequences in ICAM-1 appear to be recognized. This is similar to Ig binding to protein antigens in which residues in three noncontiguous complementary-determining regions confer recognition specificity (Alzari, P. M. et al., *Ann. Rev. Immunol.* SS:555–580 (1988)).

ICAM-1 is able to bind another leukocyte integrin, MAC-1, which also binds ligands such as iC3b and fibrinogen in an RGD dependent manner. The site on ICAM-1 which binds MAC-1, however, appears to differ from that which binds LFA-1. Thus MAC-1 binds to an RGD-like sequence on ICAM-1 which would be more consistent with its other binding specificities.

ICAM-1 residues which have been defined above as being important to LFA-1 binding are conserved in other ICAMS. Human ICAM-1 is 50% identical to murine ICAM-1 and 35% identical to human ICAM-2 (Staunton, D. E., et al. *Nature* 339:61–64 (1989)). The residues that are most critical to LFA-1 binding, E34 and Q73, are conserved both in mouse ICAM-1 and in human ICAM-2. This is consistent with the ability of both mouse ICAM-1 and human ICAM-2 (Staunton, D. E., et al. *Nature*, 339:61-64 (1989)) to bind to human LFA-1. One D2 N-linked glycosylation site at N156, which influences LFA-1 binding, is also conserved in ICAM-2. Several residues that are important to rhinovirus-14 binding, Q58, G46, D71, K77 and R166, are not conserved in mouse ICAM-1 or human ICAM-2 which is consistent with the apparent inability of mouse cells (Colonno, R. J. et al., *J. Virol.* 57:7-12 (1986)) and ICAM-2 to bind rhinovirus-14.

Sequences important to LFA-1 and HRV contact also correspond to blocking mAb epitopes of RR1/1 and LB-2 whereas the R6.5 epitope does not appear to, and thus may block, binding by steric hindrance.

Binding of LFA-1 to ICAM-1 is dependent on divalent cations. All integrin α subunits have 3 or 4 tandem repeats of "EF hand"-like divalent cation binding sites (Kishimoto, T. K. et al., *Adv. Immunol.* 46:149-182 (1989)). However, these sites differ from the classical EF-hand motif in that they lack one conserved glutamic acid which coordinates with divalent cations (Corbi, A. L. et al. *EMBO J.* 6:4023-4028 (1987)). It has been hypothesized that this residue missing from the integrin maybe replaced by a residue in the ligand, and thus that the metal may coordinate with both the receptor and the ligand (Corbi, A. L. et al. *EMBO J.* 6:4023-4028 (1987)). The ICAM-1 residue most critical to binding LFA-1, glutamic acid 34 (E34), might provide the hypothesized coordination with the divalent cation. A similar mechanism does not appear to be present in rhinovirus-14 binding to IcAM-1, which has been found to be divalent cation independent. Previous suggestions of a divalent cation requirement for rhinovirus binding (Rueckert, R. R., in: *Fields Virology*, Fields, B. N. et al. (eds.), Raven Press, N.Y., (1985) pp 705-738) appear to be based on work with minor group serotypes, which bind to a distinct receptor. Stability as opposed to binding may be influenced by cations that coordinate asparagine 141 at the 5-fold axis of rhinovirus (Rossmann, M. G., et al., *Nature* 117:145-153 (1985)).

ICAM-1 and CD4 are members of the Ig superfamily which demonstrate striking parallels in their function in both cellular and viral adhesion. CD4 is an adhesion receptor on T cells that binds to MHC class II molecules, and is also utilized as a receptor by HIV virus. CD4 has 4 extracellular domains. Recent studies on CD4 have found that mutations in the amino-terminal Ig-like domain have the strongest effect on binding of MHC class II and HIV, with a lesser effect of mutations in the second domain. The binding sites for MHC class II and HIV are overlapping but distinct (Peterson, A. et al., *Cell* 54:65-72 (1988)); Clayton, L. K. t al., *Nature* 239:548-551 (1989); Lamarre, D. et al. *Science* 245:743,-746 (1989); Landau, N. R. et al., *Nature* 334:159-167 (1988), all of which references are incorporated herein by reference). Some CD4 mAb epitopes appear to involve residues from both D1 and 2 demonstrating close physical association of these domains (Landau, N. R. et al., *Nature* 334:159-167 (1988)). In all these respects, findings on the cell adhesion and virus binding sites of ICAM-1 and CD4 are similar.

At least two different models may be envisioned for binding of ICAM-1 domain I to the putative receptor site in the rhinovirus canyon. As mentioned above, the majority (6 out of 9) of D1 sequences implicated in rhinovirus-14 contact may locate to the distal half of D1 (FIG. 26). The receptor binding site in the rhinovirus canyon has been implicated to be in a deep cleft, 3 nm wide at the top, 1.2 nm wide at the bottom, and 2.5 nm deep (Rossmann, M. G., et al. *Nature* 317:145-153 (1985); Colonno, R. J. et al., *Proc. Natl. Acad. Sci.* 85:5449-5453 (1988); Rossmann, M. G. et al., *Ann. Rev. Biochem.* 58:533-573 (1989)). The dimensions of this cleft are such that slightly more than half of an Ig-like domain (4 nm long and 2-2.5 nm wide) could be inserted. Thus the contact sequences in the distal half of ICAM-1 D1 may form bonds with residues within the cleft such that the long axis of D1 is approximately perpendicular to the floor of the canyon. The distance between the center of each deep cleft around the 5-fold axis, approximately 5 nm, is great enough to allow an ICAM-1 molecule to occupy all 5 clefts. The remaining sequences implicated in rhinovirus-14 contact, K39DE, Q58 and R166PQ, that may not locate to the distal half of D1 might interact with rhinovirus-14 residues in the rim of the canyon.

A second model of ICAM-1 / rhinovirus-14 interaction would be that ICAM-1 D1 contacts residues of the cleft such that the long axis of D1 would form a more acute angle with the floor of the canyon, allowing D1 and D2 to lie more lengthwise in the canyon. This may result in blocking by steric hindrance of some neighboring rhinovirus-14 binding sites.

Thus, the present invention resolves major points of contact between ICAM-1 and LFA-1 or HRV. Identification of ICAM-1 contact sequences provides additional information for the design of ICAM-1 fragments and synthetic peptides which inhibit LFA-1 and/or HRV binding. For example, the data shows that an ICAM-1 fragment consisting of D1 alone will be sufficient to inhibit both LFA-1 and HRV interaction; however, results presented here suggest that an even more efficient binding conformation will contain both D1 and D2. Since discontinuous ICAM-1 sequences appear to be involved in contact, a long peptide fragment or several shorter peptides which span multiple contact sequences may be used to compete LFA-1 and HRV interactions.

Thus, the identification here of the important binding sites within the first 2 domains of ICAM-1 demonstrates that soluble fragments of ICAM-1 possess potential therapeutic utility in preventing rhinovirus infection and in the treatment of inflammatory disorders and conditions (such as reperfusion injury, transplantation, etc.). Such agents may be effective in therapeutic treatment of 50% of cases with common cold symptoms which are caused by the major group of rhinoviruses (Sperber, S. J. et al. *Antimicr. Agents Chemo.* 32: 409-419 (1988)). In reperfusion injury, leukocytes migrate into and damage tissues temporarily deprived of blood flow. Significant damage due to reperfusion injury in myocardial infarct and ischemic shock has been shown to be blocked by mAb to LFA-1 and other leukocyte integrins (Vedder, N. B. et al., *J. Clin. Invest.* 81:939-944 (1988); Simpson, P. J. et al., *J. Clin. Invest.* 81:624-629 (1988); which references are incorporated herein by reference).

Thus, in summary, LFA-1 (CD11a/CD18) on lymphocytes binds to ICAM-1 (CD54) on other cells to promote critical cell-cell adhesion during immune and inflammatory responses; furthermore, the major group of human rhinoviruses (HRV) utilized ICAM-1 as its cellular receptor. Electron micrographs show the ICAM molecule to be a rod, about 19 nm long. The rod frequently has a 90 degree bend, giving a 12 nm long arm and a 7 nm short arm. These dimensions suggest a model in which the 5 Ig-like domains are oriented at a small angle to the rod axis, with three domains in the long arm and two in the short arm. ICAM-1 sequences important to binding LFA-1, HRV, and 4 monoclonal antibodies (mAb) were identified through the characterization of ICAM-1 mutants possessing deletions of its Ig-like domains and amino acid substitutions in predicted b turns. The amino-terminal 2 Ig-like domains (D1 and D2) of ICAM-1 appear to conformationally interact, and N-linked glycosylation sites in D2 appear to be important to the structural integrity and may have a minor effect in LFA-1 binding. The amino-terminal Ig-like domain of ICAM-1 (D1) contains the primary site of contact for both LFA-1 and HRV. The binding sites appear overlapping but distinct; HRV binding also differs from LFA-1 in the lack of divalent cation dependence. Although LFA-1 is an integrin, it does not recognize a RGD or RGD-like sequence in ICAM-1. Overall, the analysis suggests that rhinoviruses mimic LFA-1 in the choice of binding site ICAM-1, raising the possibility that this is an evolutionary adaptive site.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A pharmaceutical composition comprising a pharmaceutically acceptable excipient, at least one immunosuppressive agent, and an anti-ICAM-1 antibody, or a fragment of said anti-ICAM-1 antibody, which is capable of binding to ICAM-1 and blocking the interaction of ICAM-1 with leukocytes in vivo.

2. The pharmaceutical composition of claim 1 wherein said immunosuppressive agent is selected form the group consisting of dexamethasone, azathioprine and cyclosporin A.

3. A method of decreasing the severity of inflammation associated with the leukocyte/ICAM-1 interaction comprising administration of a pharmaceutical composition comprising a pharmaceutically acceptable excipient and an anti-ICAm-1 antibody, or a fragment of said anti-ICAM-1 antibody, which is capable of binding to ICAM-1 and blocking the interaction of ICAM-1 with leukocytes.

4. The method of claim 3 wherein said inflammation is associated with organ rejection.

5. The method of claim 4, wherein said inflammation is in response to a kidney allograft.

6. The method of claim 3, wherein said inflammation is associated with rheumatoid arthritis.

7. The method of claim 3, wherein said pharmaceutical composition is provided prophylactically to said subject.

8. The method of claim 3, wherein said pharmaceutical compositions is provided therapeutically to said subject.

9. The method of claim 3, wherein said antibody is a monoclonal antibody.

10. The method of claim 3, wherein the monoclonal antibody is R6-5-D6 produced by the hybridoma ATCC 9580.

11. The method of claim 10, wherein said pharmaceutical composition is administered in a single treatment regimen.

* * * * *